(12) United States Patent
Osterloh et al.

(10) Patent No.: US 8,680,144 B2
(45) Date of Patent: *Mar. 25, 2014

(54) METHODS OF TREATING MIXED DYSLIPIDEMIA

(71) Applicant: Amarin Pharmaceuticals Ireland Limited, Dublin (IE)

(72) Inventors: Ian Osterloh, Kent (GB); Pierre Wicker, Mystic, CT (US); Rene Braeckman, Richboro, PA (US); Paresh Soni, Mystic, CT (US); Mehar Manku, Birmingham (GB)

(73) Assignee: Amarin Pharmaceuticals Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/898,457

(22) Filed: May 20, 2013

(65) Prior Publication Data

US 2013/0253031 A1    Sep. 26, 2013

Related U.S. Application Data

(63) Continuation of application No. 13/540,319, filed on Jul. 2, 2012, which is a continuation of application No. 13/417,899, filed on Mar. 12, 2012, which is a continuation of application No. 13/266,085, filed as application No. PCT/US2010/032948 on Apr. 29, 2010.

(60) Provisional application No. 61/173,759, filed on Apr. 29, 2009.

(51) Int. Cl.
*A01N 37/06* (2006.01)
*A61K 31/22* (2006.01)
*A61K 9/48* (2006.01)

(52) U.S. Cl.
USPC .......................................... 514/549; 424/451

(58) Field of Classification Search
None
See application file for complete search history.

(56) References Cited

U.S. PATENT DOCUMENTS

| | | |
|---|---|---|
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,618,558 A | 4/1997 | Horrobin et al. |
| 5,656,667 A | 8/1997 | Breivik et al. |
| 5,698,594 A | 12/1997 | Breivik et al. |
| 5,760,081 A | 6/1998 | Leaf et al. |
| 5,776,978 A | 7/1998 | Bruzzese |
| 5,837,731 A | 11/1998 | Vaddadi |
| 5,840,944 A | 11/1998 | Furihata et al. |
| 5,888,541 A | 3/1999 | Horrobin et al. |
| 6,069,168 A | 5/2000 | Horrobin et al. |
| 6,193,999 B1 | 2/2001 | Gennadios |
| 6,326,031 B1 | 12/2001 | Hsia et al. |
| 6,331,568 B1 | 12/2001 | Horrobin |
| 6,368,621 B1 | 4/2002 | Engel et al. |
| 6,384,077 B1 | 5/2002 | Peet |
| 6,479,544 B1 | 11/2002 | Horrobin |
| 6,531,150 B1 | 3/2003 | Sunohara et al. |
| 6,555,700 B1 | 4/2003 | Horrobin et al. |
| 6,689,812 B2 | 2/2004 | Peet |
| 7,022,713 B2 | 4/2006 | Aoki et al. |
| 7,119,118 B2 | 10/2006 | Peet |
| 7,498,359 B2 | 3/2009 | Yokoyama et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 2002/0016312 A1 | 2/2002 | Seed et al. |
| 2002/0035125 A1 | 3/2002 | Shear |
| 2002/0055529 A1 | 5/2002 | Bisgaier et al. |

(Continued)

FOREIGN PATENT DOCUMENTS

| | | |
|---|---|---|
| CA | 2628305 | 5/2007 |
| CA | 2653787 | 12/2007 |

(Continued)

OTHER PUBLICATIONS

Aarsland, et al., "On the Effect of Peroximsomal β-Oxidation and Carnitine Palmitoyltransferase Activity by Eicosapentaenoic Aid in Live and Heart of Rats." Lipids, 25:546-548, (1990).

(Continued)

*Primary Examiner* — Jeffrey S. Lundgren
*Assistant Examiner* — Michael Schmitt
(74) *Attorney, Agent, or Firm* — Perkins Coie LLP

(57) ABSTRACT

The present disclosure relates to, inter alia, methods of treating mixed dyslipidemia with ethyl eicosapentaenoate.

14 Claims, 2 Drawing Sheets

(56) References Cited

U.S. PATENT DOCUMENTS

| | | |
|---|---|---|
| 2002/0055539 A1 | 5/2002 | Bockow et al. |
| 2002/0077361 A1 | 6/2002 | Peet |
| 2002/0183389 A1 | 12/2002 | Peet |
| 2002/0193439 A1 | 12/2002 | Peet |
| 2002/0198177 A1 | 12/2002 | Horrobin et al. |
| 2003/0100610 A1 | 5/2003 | Shibuya et al. |
| 2003/0104048 A1 | 6/2003 | Patel et al. |
| 2003/0166614 A1 | 9/2003 | Harrison, Jr. |
| 2004/0077723 A1 | 4/2004 | Granata |
| 2004/0162348 A1 | 8/2004 | Peet |
| 2005/0187292 A1 | 8/2005 | Aoki et al. |
| 2006/0034815 A1 | 2/2006 | Guzman et al. |
| 2006/0134178 A1 | 6/2006 | Doisaki et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0252833 A1 | 11/2006 | Peet |
| 2007/0104779 A1 | 5/2007 | Rongen et al. |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0191467 A1 | 8/2007 | Rongen et al. |
| 2008/0020018 A1 | 1/2008 | Moodley et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0200547 A1 | 8/2008 | Peet et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0182049 A1 | 7/2009 | Opheim |
| 2009/0227602 A1 | 9/2009 | Griffin et al. |
| 2009/0304784 A1 | 12/2009 | Mane et al. |
| 2010/0021555 A1 | 1/2010 | Geiringer et al. |
| 2010/0119598 A1 | 5/2010 | Yoshinari et al. |
| 2010/0311834 A1 | 12/2010 | Manku et al. |
| 2011/0034555 A1 | 2/2011 | Osterloh et al. |
| 2011/0288171 A1 | 11/2011 | Manku et al. |
| 2012/0100208 A1 | 4/2012 | Manku |

FOREIGN PATENT DOCUMENTS

| | | |
|---|---|---|
| CA | 2675836 | 7/2008 |
| CA | 2724983 | 11/2009 |
| CN | 101252837 A | 8/2008 |
| EP | 0302482 | 2/1989 |
| EP | 0460917 | 12/1991 |
| EP | 0606012 | 7/1994 |
| EP | 0610506 | 8/1994 |
| EP | 1157692 | 11/2001 |
| EP | 1296670 | 4/2003 |
| EP | 1743644 | 1/2007 |
| EP | 2022495 | 2/2009 |
| FR | 2635263 | 2/2009 |
| GB | 2148713 | 6/1985 |
| GB | 2221843 | 2/1990 |
| GB | 2229363 | 9/1990 |
| GB | 9901809.5 | 1/1999 |
| HU | P0200686 | 8/1990 |
| JP | 04182426 | 6/1992 |
| KR | 10-2006-0109988 | 10/2006 |
| WO | WO 90/04391 | 5/1990 |
| WO | WO 92/21335 | 12/1992 |
| WO | WO 94/28891 | 12/1994 |
| WO | WO 97/39759 | 10/1997 |
| WO | WO 98/16216 | 4/1998 |
| WO | WO 99/29316 | 6/1999 |
| WO | WO 00/44361 | 8/2000 |
| WO | WO 00/51573 | 9/2000 |
| WO | WO 01/15552 | 3/2001 |
| WO | WO 02/02105 | 1/2002 |
| WO | WO 02/058793 | 8/2002 |
| WO | WO 02/089787 | 11/2002 |
| WO | WO 02/096408 | 12/2002 |
| WO | WO 03/068216 | 8/2003 |
| WO | WO 2004/050913 | 6/2004 |
| WO | WO 2004/078166 | 9/2004 |
| WO | WO 2004/082402 | 9/2004 |
| WO | WO 2007/016256 | 2/2007 |
| WO | WO 2007/017240 | 2/2007 |
| WO | WO 2007/073176 | 6/2007 |
| WO | WO 2007/075841 | 7/2007 |
| WO | WO 2007/128801 | 11/2007 |
| WO | WO 2007/142118 | 12/2007 |
| WO | WO 2008/004900 | 1/2008 |
| WO | WO 2008/045465 | 4/2008 |
| WO | WO 2008/106787 | 9/2008 |
| WO | WO 2009/004999 | 1/2009 |

OTHER PUBLICATIONS

Aas, V., et al., "Eicosapentaenoic acid (20:5 n-3) increases fatty acid and glucose uptake in cultured human skeletal muscle cells." Journal of Lipid Research, 47:366-374 (2006).

Abbey, M., et al., "Effect of fish oil on lipoproteins, lecithin:cholesterol acyltransferase, and lipidtransfer protein activity in humans" Arterioscler. Thromb. Vasc. Biol. 10:85-94 (1990).

Ackman et al., The "Basic" Fatty Acid Composition of Atlantic Fish Oils: Potential Similarties Useful for Enrichment of Polyunsaturated Fatty Acids by Urea Complexation, JAOCS, vol. 65, 1:136-138 (Jan. 1988).

Adan, Y., et al., "Effects of docosahexaenoic and eicosapentaenoic acid on lipid metabolism, eicosanoid production, platelet aggregation and atherosclerosis." Biosci. Biotechnol. Biochem. 63(1), 111-119 (1999).

Adan, Y., et al., "Concentration of serum lipids and aortic lesion size in female and male apo E-deficient mice fed docosahexaenoic acid." Biosci. Biotechnol. Biochem. 63(2):309-313 (1999).

Agren, J.J., et al., "Fatty acid composition of erythrocyte, platelet, and serum lipids in strict vegans." Lipids 30:365-369 (1995).

Agren, J.J., et al., "Fish diet, fish oil and docosahexaenoic acid rich oil lower fasting and postprandial plasma lipid levels." Eur J Clin Nutr. 1996;50:765-771.

Ando, M., et al., "Eicosapentanoic acid reduces plasma levels of remnant lipoproteins and prevents in vivo peroxidation of LDL in dialysis patients." J. Am. Soc. Nephrol., 10:2177-2184 (1999).

Ando, Y., et al., "Positional distribution of highly unsaturated fatty acids in triacyl-sn-glycerols of *Artemia nauplii* enriched with docosahexaenoic acid ethyl ester." Lipids 36:733-740 (2001).

Andrade, S.E., et al., (1995) Discontinuation of antihyperlipidaemic drugs_do rates reported in clinical trials reflect rates in primary care settings? New Eng. J. Med. 332: 1125-1131.

Angerer, P., et al., "n-3 Polyunsaturated Fatty Acids and the Cardiovascular System", Current Opinion in Lipidology, 11(1):57-63, 2000.

Anil, E., "The Impact of EPA and DHA on Blood Lipids and Lipoprotein Metabolism: Influence of ApoE Genotyle", Proceedings of the Nutrition Society, 66:60-68, 2007.

Aoki T et al. "Experience of the use of ethyl eicosapentaenoic acid preparation (Epadel) in patients with arteriosclerosis complicated with diabetes mellitus. A study of the long-term effects on glycemic control and blood lipids," Rinsho to Kenkyu 1993; 70:625-631.

Appelton, K.M., et al., "Effects of n-3 long-chain polyunsaturated fatty acids on depressed mood: systematic review of published trials," Am. J. Clin. Nutr. 84(6):1308-1316 (Dec. 2006).

Arrol, S. et al., "The effects of fatty acids on apolipoprotein B secretion by human hepatoma cells (HEP G2)," Atherosclerosis 150 (2000) 255-264.

Arshad, A., et al., "Sudden cardiac death and the role of medical therapy." Progress in Cardiovascular Diseases, vol. 50, No. 6, 420-438, (2008).

Arterburn, L., et al., "Distribution, interconversion, and dose response of n-3 fatty acids in humans." Am J Clin Nutr., 83:1467S-76S (2006).

(56) References Cited

OTHER PUBLICATIONS

Asano, M., et al., "Eicosapentaenoic acid inhibits vasopressin-activated Ca2q influx and cell proliferation in rat aortic smooth muscle cell lines." European Journal of Pharmacology 379:199-209 (1999).
Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (1997).
ATP III guidelines, NIH publication No. 01-3305 (2001).
Ayton, et al., "A pilot open case series of Ethyl-EPA supplementation in the treatment of anorexia nervosa," Prostaglandins, Leukotrienes and Essential Fatty Acids 71 (2004) pp. 205-209.
Ayton, et al., "Rapid improvement of severe anorexia nervosa during treatment with ethyl-eicosapentaenoate and micronutrients," European Psychiatry 19 (2004) pp. 317-319.
Baigent, C., et al., "Efficacy and safety of cholesterol-lowering treatment: prospective meta-analysis of data from 90,056 participants in 14 randomised trials of statins." Lancet. 2005;366:1267-1278.
Balk, E.M., et al., "Effects of omega-3 fatty acids on serum markers of cardiovascular disease risk: a systematic review. Atherosclerosis." 2006;189:19-30.
Ballantyne et al., Influence of low-high density lipoprotein cholesterol and elevated triglyceride on coronary heart disease events and response to simvastatin therapy in 4S, Circulation 2001, 104:3046-3051.
Bang HO, Dyerberg J. "Plasma lipids and Lipoproteins in Greenlandic west coast Eskimos" Acta Med Scand 1972; 192:85-94.
Banga, A., et al., "Adiponectin translation is increased by the PPARγ agonists pioglitazone and ω-3 fatty acids." Am J Physiol Endocrinol Metab 296:480-489 (2009).
Bansal S, Buring JE, Rifai N, Mora S, Sacks FM, Ridker PM, "Fasting Compared With Nonfasting Triglycerides and Risk of Cardiovascular Events in Women," JAMA 2007; 298:309-316.
Basu, A., et al., "Dietary Factors That Promote or Retard Inflammation." Arterioscler. Thromb. Vasc. Biol. 26:995-1001 (2006).
Bays HE et al. "Prescription omega-3 fatty acids and their lipid effects: physiologic mechanisms of action and clinical implications," Expert Rev Cardiovasc Ther 2008; 6:391-409.
Bays, H., Clinical Overview of Omacor: A Concentrated Formulation of Omega-3 Polyunsaturated Fatty Acids, Am J cardiol 2006;98[suppl]:71i-76i.
Bays, H., "Rationale for Prescription Omega-3-Acid Ethyl Ester Therapy for Hypertriglyceridemia: A Primer for Clinicians," Drugs of Today 2008,44(3); 205-246.
Bays, H.E., et al., "Long-term up to 24-month efficacy and safety of concomitant prescription omega-3-acid ethyl esters and simvastatin in hypertriglyceridemic patients." Curr Med Res Opin. 2010;26:907-915.
Bays, H.E., Eicosapentaenoic Acid Ethyl Ester (AMR101) Therapy in Patients With Very High Triglyceride Levels (from the Multicenter, plAcebo-controlled, Randomized, double-blINd, 12-week study with an open-label Extension [MARINE] Trial) Am J Cardiol 2011;108:682-690.
Beal, M.F., Annals of Neurology, vol. 38, No. 3, "Aging, Energy, and Oxidative Stress in Neurodegenerative Diseases", pp. 357-366, Sep. 1995.
Belmaker, et al., "Addition of Omega-3 Fatty Acid to Maintenance Medication Treatment for Recurrent Unipolar Depressive Disorder," Am J Psychiatry 2002; 159:477-479.
Belmaker, et al., "Omega-3 Eicosapentaenoic Acid in Bipolar Depression: Report of a Small Open-Label Study," J Clin Psychiatry 2005 66:726-729.
Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (1996).
Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J. 1999; 343(Pt 1):191-197.
Betteridge, D.J., "Diabetic dyslipidaemia: past, present and future." Practical Diabetes Int, 21(2): 78-85. (2004).
Black, K.L., et al., "Effect of intravenous eicosapentaenoic acid on cerebral blood flow, edema, and brain prostaglandins in ischemic gerbils", Prostaglandins (1984), 28(4), pp. 545-546.
Blankenhorn, D.H., et al., (1987) Beneficial effects of combined colestipol-naicin therapy on coronary atheroscherosis and coronary venous bypass grafts. JAMA 257: 3233-3240.
Block, R. C., et al., "EPA and DHA in blood cell membranes from acute coronary syndrome patients and controls." Atherosclerosis, 197(2):821-828 (2007).
Blumenthal (Advanced Studies in Medicine (2002) 2:148-157).
Bonaa, KH et al., Docosahexaenoic and Eicosapentaenoic acids in plasma phospholipids are divergently associated with high density lipoprotein in humans, Arterioscler. Thromb. Vasc. Biol. 1992;12;675-681.
Bousserouel, S., et al., "Different effects of n-6 and n-3 polyunsaturated fatty acids on the activation of rat smooth muscle cells by interleukin-1β." J. Lipid Res. 44:601-611 (2003).
Bousserouel, S., et al., "Modulation of cyclin D1 and early growth response factor-1 gene expression in interleukin-1β-treated rat smooth muscle cells by n-6 and n-3 polyunsaturated fatty acids." Eur. J. Biochem. 271:4462-4473 (2004).
Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91(2004).
Breslow, J., "n-3 Fatty acids and cardiovascular disease." Am J Clin Nutr., 83:1477S-82S (2006).
Brossard, N., et al., "Retroconversion and metabolism of [13C]22:6n-3 in humans and rats after intake of a single dose of [13C]22:6n-3-3-triacyylglycerols." Am. J. Clin. Nutr. 64:577-86 (1996).
Brouwer, I.A., et al., "Effect of fish oil on ventricular tachyarrhythmia and death in patients with implantable cardioverter defibrillators." JAMA. 295(22):2613-2619 (2006).
Brown et al., Simvastatin and Niacin, Antioxidant Vitamins, or the Combination for the Prevention of Coronary Disease, N Engl J Med, vol. 345, No. 22, Nov. 29, 2001.
Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (1999).
Brown, A. J., et al., "Persistent changes in the fatty acid composition of erythrocyte membranes after moderate intake of n-3 polyunsaturated fatty acids: study design and implications." Am.J. Clin. Nutri. 54:668-73(1991).
Brown, G., et al., (1990) Regression of coronary artery-disease as a result of intensive lipid-lowering therapy in men with high levels of apolipoprotein B., N. Engl. J. Med. 323: 1289-1298.
Bryhn, M., et al., "The bioavailability and pharmacodynamics of different concentrations of omega-3 acid ethyl esters." Prostaglandins, Leukotrienes and Essential Fatty Acids 75:19-24 (2006).
Budavari, S., Editor, The Merck Index, 1989, Merck & Co., Inc., Rahway, N.J., entry 2417 on p. 379 and 4511 on p. 725.
Bunting, et al., "Depression in Parkinson's Disease", J. Neurosci Nurs. Jun. 1991; 23(3):158-164, (Abstract Only).
Burdge, G.C., et al., "Eicosapentaenoic and docosapentaenoic acids are the principal products of a-linolenic acid metabolism in young men." British Journal of Nutrition 88:355-363 (2002).
Burdge, G.C., et al., "Lack of effect of meal fatty acid composition on postprandial lipid, glucose and insulin responses in men and women aged 50-65 years consuming their habitual diets." British Journal of Nutrition, 96:489-500 (2006).
Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (2007).

(56) References Cited

OTHER PUBLICATIONS

Burr, M. L., et al., "Effects of changes in fat, fish and fibre intakes on death and myocardial reinfarction: Diet and reinfarction trial." The Lancet, Sep. 30, 1989; 2(8666):757-61.
Calabresi, L., et al., "Omacor in familial combined hyperlipidemia: effects on lipids and low density lipoprotein subclasses." Atherosclerosis 148:387 396 (2000).
Campos, H., et al., "Lowdensity lipoprotein size, pravastatin treatment, and coronary events." JAMA. 2001;286:1468-1474.
Canner, P.L., et al., (1986) Fifteen year mortality in Coronary Drug Project patients: long-term benefit with niacin, J. Am. Coll. Cardiol. 8.1245-1255.
Cao, J., et al., "Incorporation and Clearance of Omega-3 Fatty Acids in Erythrocyte Membranes and Plasma Phospholipids." Clinical Chemistry 52(12):2265-2272 (2006).
Cao, Y., et al., Genomics, vol. 49, "Cloning, Expression, and Chromosomal Localization of Human Long-Chain Fatty Acid CoA Ligase 4 (FACL4)," pp. 327-330, 1998.
Capuzzi, et al. "Efficacy and Safety of an Extended-Release Niacin (Niaspan): A Long-Term Study," Am J Cardiol 1998;82:74U-81U.
Carlson, L.A. & Rosenhamer G. (1988). Reduction of mortality in the Stockholm Ischaemic Heart Disease Secondary Prevention Study by combined treatment with clofibrate and nicotinic acid. Acta Med. Scand. 223,405-418.
Carlson, L.A., Nicotinic acid: the broad-spectrum lipid drug. A $50^{th}$ anniversary review, Journal of Internal Medicine, 2005: 258: 94-114.
Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390, 2007.
Carroll, D. N., et al., "Evidence for the Cardioprotective Effects of Omega-3 Fatty Acids." Ann Pharmacother., 36:1950-6 (2002).
Cazzola, R., et al., "Age- and dose-dependent effects of an eicosapentaenoic acid-rich oil on cardiovascular risk factors in healthy male subjects." Atherosclerosis 193:159-167 (2007).
Cefali, E.A, et al., "Aspirin reduces cutaneous flushing after administration of an optimized extended-release niacin formulation." International Journal of Clinical Pharmacology and Therapeutics, vol. 45—No. 2/2007 (78-88).
Center for Drug Evaluation and Research. Omacor (Lovaza) Medical Reviews 2004 (last accessed May 29, 2008 at http://www.fda.gov/cder/foi/nda/2004/21-654_Omacor_Medr.pdf).
Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. Accessed Jan. 26, 2012.
Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012.
Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002).
Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003).
Chapman, M.J., et al., "Cholesteryl ester transfer protein: at the heart of the action of lipid-modulating therapy with statins, fibrates, niacin, and cholesteryl ester transfer protein inhibitors." Eur Heart J. 2010;31:149-164.
Chemical Book, Eicosapentaenoic acid ethyl ester, copyright 2010, printed Jun. 16, 2011 from www.chemicalbook.com.
Chen, H., et al., "Eicosapentanoic acid inhibits hypoxia-reoxygenation-induced injury by attenuating upregulation of MMP-1 in adult rat myocytes." Cardiovascular Research 59:7-13 (2003).
Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (2003).
Chen, I.S., et al., "In vitro clearance of chylomicron triglycerides containing (ω-3) eicosapentaenoate." Atherosclerosis, 65:193-198 (1987).
Childs, M.T., et al., "Divergent lipoprotein Responses to Fish Oils With Various Ratios of Eicosapentaenoic Acid and Docasahexaenoic Acid", American Society for Clinical Nutrition, 52:632-9, 1990.
Christensen, J. H., et al., "Effect of fish oil on heart rate variability in survivors of myocardial infarction: a double blind randomised controlled trial." BMJ, 312:677-678 (1996).
Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (1995).
Cleland, L.G., et al., "A Biomarker of n-3 compliance in patients taking fish oil for rheumatoid arthritis." Lipids 38:419-424 (2003).
Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from the Internet: <http://clinicaltrials.gov/ct2/show/NCT01047501>.
Cohen, J.D., et al., "30-year trends in serum lipids among United States adults: results from the National Health and Nutrition Examination Surveys II, III, and 1999-2006." Am J Cardiol. 2010;106:969-975.
Cole et al., "Challenges and opportunities in the encapsulation of liquid and semi-solid formulations into capsules for oral administration," Advanced Drug Delivery Reviews, vol. 60, No. 6, Dec. 21, 2007, pp. 747-756.
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (2004).
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (2008).
Conklin, S. M., et al., "Serum ω-3 fatty acids are associated with variation in mood, personality and behavior in hypercholesterolemic community volunteers." Psychiatry Research 152: 1-10 (2007).
Connor et al., "Seminars in thrombosis and hemostasis" (1988) 14:271-284.
Connor, W.E., "Importance of n-3 Fatty Acids in Health and Disease", Am. J. Clin. Nutr., 71(1(S)):171S-175S, 2000.
Conquer, J.A., et al., "Effect of supplementation with different doses of DHA on the levels of circulating DHA as non-esterified fatty acid in subjects of Asian Indian background. J Lipid Res." 1998;39:286-292.
Conquer, J.A., et al., "Supplementation with an algae source of docosahexaenoic acid increases (n-3) fatty acid status and alters selected risk factors for heart disease in vegetarian subjects." J Nutr. 1996;126: 3032-3039.
Contacos et al. Effect of pravastatin and omega-3 fatty acids on plasma lipids and lipoproteins in patients with combined hyperlipidemia, pp. 1755-1762, 1993.
Criqui, M., "Triglycerides and Coronary Heart Disease Revisited (Again)," Sep. 18, 2007, vol. 147 No. 6, pp. 425-427.
Crowe, F. L., et al., "Serum phospholipid n-3 long-chain polyunsaturated fatty acids and physical and mental health in a population-based survey of New Zealand adolescents and adults." Am J Clin Nutr 86:1278-85 (2007).
Daggy, B., et al., Dietary fish oil decreases VLDL production rates. Biochimica et Biophysics Acta 920: 293-300 (1987).
Das, U.N., Essential fatty acids as possible mediators of the actions of statins. Prostaglandins, Leukotrienes and Essential FattyAcids 65(1):37-40, (2001).
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther 2007; 29:1354-1367.

(56) References Cited

OTHER PUBLICATIONS

Davidson MH. (2006). "Mechanisms for the hypotriglyceridemic effect of marine omega-3 fatty acids." Am J Cardiol 98(4A):27i-33i.
Davidson, M.H., et al., "Effects of docosahexaenoic acid on serum lipoproteins in patients with combined hyperlipidemia: a randomized, doubleblind, placebo-controlled trial." J Am Coll Nutr. 1997;16:236-243.
De Caterina, R, et al., "Control of Endothelial Leukocyte Adhesion Molecules by Fatty Acids." Lipids, vol. 31:S57-S63 (1996).
De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994).
Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008).
Dewailly, E., et al., "n-3 Fatty acids and cardiovascular disease risk factors among the Inuit of Nunavik." Am J Clin Nutr 74:464-73 (2001).
Diagnostic and Statistical Manual of Mental Disorders, 4th. Ed, published by the American Psychiatric Assoc., pp. 285-286, 1994.
Diagnostic and Statistical Manual of Mental Disorders, 4th. Ed. text revision, published by the American Psychiatric Assoc., pp. 154-163, and 369-381, 2000.
Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, Jan. 1996.
Dijk, J. M., et al., "Carotid intima—media thickness and the risk of new vascular events in patients with manifest atherosclerotic disease: the SMART study." European Heart Journal 27:1971-1978 (2006).
Dodin, S., et al., "Flaxseed on cardiovascular disease markers in healthy menopausal women: a randomized, double-blind, placebo-controlled trial." Nutrition 24:23-30 (2008).
Dolecek, D.A., "Epidemiological Evidence of Relationships Between Dietary Polysunsaturated Fatty Acids and Morality in the Multiple Risk Factor Intervention Trial", Society of Experimental Biology and Medicine, 200(2):177-182, 1991.
Dullenmeijer, C., et al., "n-3 Fatty acid proportions in plasma and cognitive performance in older adults." Am J Clin Nutr 86:1479-85 (2007).
Duncan, R. E., et al., "Regulation of HMG-CoA reductase in MCF-7 cells by genistein, EPA, and DHA, alone and in combination with mevastatin." Cancer Letters 224:221-228 (2005).
Durrington PN et al. "An omega-3 poly unsaturated fatty acid concentrate administered for one year decreased triglycerides in simvastatin treated patients with coronary heart disease and persistent Hypertriglyceridemia," Heart 2001; 85:544-48.
Dwyer, J. H., et al., "Arachidonate 5-Lipoxygenase Promoter Genotype, Dietary Arachidonic Acid, and Atherosclerosis." N. Engl. J. Med., 350:1 (2004).
Dyerberg, J., et al., "Marine Oils and Thrombogenesis." Prog. Lipid Res. 21:255-269 (1982).
Egert, S., et al., "Dietary alpha-linolenic acid, EPA, and DHA have differential effects on LDL fatty acid composition but similar effects on serum lipid profiles in normolipidemic humans." J Nutr. 2009;139:861-868.
Eisenberg S, Bilheimer DW, Levy RI, Lindgren FT. "On the metabolic conversion of human plasma very low density lipoprotein to low density lipoprotein," Biochim Biophys Acta 1973; 326:361-77.
Eisenberg S, Rachmilewitz D. "Metabolism of rat plasma very low density lipoprotein. I. Fate in circulation of the whole lipoprotein," Biochim Biophys Acta 1973; 326:378-90.
Elam et al., Effect of Niacin on Lipid and Pipoprotein Levels and Glycemic Control in Patients With Diabetes and Peripheral Arterial Disease: The ADMIT Study: A Randomized Trial, JAMA, 2000;284(10); 1263-1270.

El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10): 1037-43 (1999).
Engler, et al., "Docosahexaenoic acid restores endothelial function in children with hyperlipidemia: results from the EARLY Study." International Journal of Clinical Pharmacology and Therapeutics, vol. 42—No. 12—2004 (672-679).
Engler, M.B., et al., "Mechanisms of vasorelaxation induced by eicosapentaenoic acid (20:5n-3) in WKY rat aorta." British Journal of Pharmacology 131:1793-1799 (2000).
Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999).
Epadel® [Complete prescribing information]. Update (Version 5). Tokyo, Japan: Mochida Pharmaceutical; Jan. 2007. (English translation).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000).
Fer, M., et al., "Metabolism of eicosapentaenoic and docosahexaenoic acids by recombinant human cytochromes P450." Archives of Biochemistry and Biophysics 471:116-125 (2008).
Ferns, G., et al., "Investigation and management of hypertriglyceridaemia." J. Clin. Pathol. 61:1174-1183 (2008).
Finnen, M.J., et al., Biochemical Society Trans., "Purification and characterization . . . ", p. 19, 1991.
Fisher et al., Journal of Biological Chemistry (2001) 276(3) 27855-27863.
Fischer, R., et al., "Dietary n-3 polyunsaturated fatty acids and direct renin inhibition improve electrical remodeling in a model of high human renin hypertension." Hypertension 51:540-546 (2008).
Flaten, H., et al., "Fish-oil concentrate: effects on variables related to cardiovascular disease." Am. J. Clin. Nutr. 52:300-306 (1990).
Ford, E.S. et al., "Hypertriglyceridemia and Its Pharmacologic Treatment Among US Adults." Arch, Intern. Med., 169(6): 572-78 (2009).
Frick, M.H., et al., (1987) Helsinki Heart Study Primary prevention trial with gemfibrozil in middle-aged men and dyslipidaemia, afety of treatment, changes in risk factors and incidence of coronary heat disease. N. Eng. J. Med. 317: 1237-1245.
Friedewald, W.T., et al., "Estimation of the concentration of low-density lipoprotein cholesterol in plasma, without use of the preparative ultracentrifuge." Clin Chem. 1972;18:499-502.
Friedman, A. N., et al., "Fish Consumption and Omega-3 Fatty Acid Status and Determinants in Long-Term Hemodialysis." Amer. J. Kidney Diseases, 47(6):1064-1071 (2006).
Frøyland, L., et al., "Hypotriacylglycerolemic component of fish oil." Prostaglandins, Leukotrienes and Essential Fatty Acids 57 (4 & 5):387-388 (1997).
Garg et al., "Niacin treatment increases plasma homocyst(e)ine levels," Am Heart J 1999;138:1082-7.
Garnett, WR, Am J Health-Sys Pharm vol. 52 (1995); 1639-1645.
Genest, J.J., et al., (1992) Familial lipoprotein disorders in patients with premature coronary artery disease, Circulation. 85: 2025-2033.
Geppert, et al. "Microalgal docosahexaenoic acid decreases plasma triacylglycerol in normolipidaemic vegetarians: a randomized trial." British Journal of Nutrition (2006), 95,779-786.
Gillies, et al. "Effect of a Novel Eicosapentaenoic Acid-Rich Oil on Serum Cholesterol in Man," DuPont 2010.
Ginsberg HN. "Hypertriglyceridemia: new insights and new approaches to pharmacologic therapy," Am J Cardiol 2001; 87:1174-1180.
GISSI-Prevenzione Investigators, "Dietary Supplementation with n-3 Polyunsaturated Fatty Acids and Vitamin E after Myocardial Infarction: Results of the GISSI-Prevenzione Trial", The Lancet, 354:447-455, Aug. 7, 1999.
Glod, "Recent Advances in the Pharmacacotherapy of Major Depression", Arch. Psychiatr. Nurs. Dec. 1996: 10(6):355-364. (Abstract Only).
Goldberg, A C: "Combination therapy of dyslipidemia," Current Treatment Options in Cardiovascular Medicine Aug. 2007 GB, vol, 9, No. 4, pp. 249-258.

(56) References Cited

OTHER PUBLICATIONS

Gordon, D.J., et al., (1989) High density lipoprotein cholesterol and cardiovascular disease: four prospective American studies. Circulation, 79: 8-15.

Gorriz JL et al. (1996) "Rhabdomyolysis and Acute Renal Failure Associated with Gemfibrozil Therapy," Nephron 74(2): 437-438.

Gorriz, JL (1995) "Rhabdomyolysis and Acute Renal Failure Associated with Bezafibrate Treatment," Nephrol Dial Transplant 10(12):2371-2372.

Goto, Y., et al., "Clinical Pharmacological Trial of Ethyl Icosapentate (MND-21)-Dose Finding Study." Journal of Clinical Therapeutic & Medicines 8:1293-309 (1992).

Gould, A.L., et al., "Cholesterol reduction yields clinical benefit: impact of statin trials." Circulation. 1998;97:946-952.

Grenyer, Brin F.S., et al., "Fish Oil Supplementation in the Treatment of Major Depression: A Randomised Double-Blind Placebo-Controlled Trial" Progress in Neuro-Psychopharmacology & Biological Psychiatry 31:1393-1396 (2007).

Griffin, M.D., et al., "Effects of altering the ratio of dietary n-6 to n-3 fatty acids on insulin sensitivity, lipoprotein size, and postprandial lipemia in men and postmenopausal women aged 45-70 y: The OPTILIP Study." Am J Clin Nutr 84:1290-8 (2006).

Grimsgaard, S., et al., "Effects of Highly Purified Eicosapentaenoic Acid and Docosahexaenoic Acid on Hemodynamics in Humans" American Society for Clinical Nutrition, 68:52-9, 1998.

Grimsgaard, S., et al., "Highly purified eicosapentaenoic acid and docosahexaenoic acid in humans have similar triacylglycerol-lowering effects but divergent effects on serum fatty acids" Am. J. Clin. Nutr., 66:649-59, 1997.

Grundy et al., Efficacy, Safety, and Tolerability of Once-Daily Niacin for the Treatment of Dyslipidemia Associated with Type 2 Diabetes, Arch Intern Med. 2002;162:1568-1572.

Guallar, E., et al., "Omega-3 fatty acids in adipose tissue and risk of myocardial infarction—The EURAMIC study." Arterioscler. Thromb. Vasc. Biol., 19:1111-1118 (1999).

Guillot, et al., "Increasing intakes of the long-chain ω-3 docosahexaenoic acid: effects on platelet functions and redox status in healthy men," The FASEV Journal, vol. 23, Sep. 2009, pp. 2909-2916.

Guizy, M., et al., "ω-3 and ω-6 Polyunsaturated fatty acids block HERG channels." Am J Physiol Cell Physiol 289:C1251-C1260 (2005).

Gyarmathy, M., "Selection from the industrial manufacturing. $5^{th}$ part: Gelatine capsules. 5/2 part: Soft gelatine capsules," Gyogyszereszet, vol. 38, No. 2, Feb. 1, 1994, pp. 105-109.

Hall, W. L., et al., "A high-fat meal enriched with eicosapentaenoic acid reduces postprandial arterial stiffness measured by digital volume pulse analysis in healthy men." J. Nutr. 138: 287-291 (2008).

Hamazaki et al., "Effects of Orally Administered Ethyl Ester of Eicosapentaenoic Acid (EPA: C20:5, omega-3) On PG12-Like Substance Production by Rat Aorta" Prostaglandins, Apr. 1982, vol. 23 No. 4, pp. 557-567.

Hamazaki T. et al., "Reduction of microalbuminuria in diabetics by Eicosapentaenoic acid ethyl ester" Lipids. 25 (9):542-5 (Sep. 1990).

Hamazaki, T., et al., "Docosahexaenoic Acid-Rich Fish Oil Does Not Affect Serum Lipid Concentrations of Normolipidemic Young Adults", American Institute of Nutrition, 126(11):2784-2789, Nov. 1996.

Han, J. J., et al., "Enhancement of both reaction yield and rate of synthesis of structured triacylglycerol containing eicosapentaenoic acid under vacuum with water activity control." Lipids 34:989-995 (1999).

Hanasaki, K., et al., "Potent modification of low density lipoprotein by group X secretory phospholipase A2 is linked to macrophage foam cell formation." J. Biol. Chem. 277(32):29116-24 (2002).

Haney, E.M., et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce. org/uspstf07/chlipid/chlipidsyn.pdf. Accessed Mar. 23, 2011.

Hannah, J., et al., "Effect of dietary fatty acids on LDL binding." Ann N Y Acad Sci. 1993; 683:178-182.

Hansen, J.B., et al., "Effects of highly purified eicosapentaenoic acid and docosahexaenoic acid on fatty acid absorption, incorporation into serum phospholipids and postprandial triglyeridemia." Lipids 33:131-38 (1998).

Harkonarson, H., et al., "Effects of a 5-lipoxygenase-activating protein inhibitor on biomarkers associated with risk of myocardial infarction—a randomized trial." JAMA, 293(8):2245-56 (2005).

Harris, W. S. et al. "Safety and efficacy of Omacor in severe hypertriglyceridemia," Journal of Cardiovascular Risk 1997, 4:385-391.

Harris, W. S., "Fish oils and plasma lipid and lipoprotein metabolism in humans: a critical review." J Lipid Res. 30:785-807 (1989).

Harris, W. S., "The omega-3 index as a risk factor for coronary heart disease." Am J Clin Nutr 87:1997S-2002S (2008).

Harris, W. S., et al., "Influence of n-3 fatty acid supplementation on the endogenous activities of plasma lipases." Am. J. Clin. Nutr. 66:254-60 (1997).

Harris, W. S., et al., "n-3 Fatty acids and urinary excretion of nitric oxide metabolites in humans." Am. J. Clin. Nutr., 65:459-64 (1997).

Harris, W.S., "Expert opinion: omega-3 fatty acids and bleeding—cause for concern?" The American Journal of Cardiology 99(6A): 45C-46C (2007).

Harris, W.S., "n-3 Fatty acids and human lipoprotein metabolism: an update." Lipids 34:S257-S258 (1999).

Harris, W.S., "n-3 Fatty acids and serum lipoproteins: human studies." Am J Clin Nutr 65:1645S-54S (1997).

Harris, W.S., "Omega-3 fatty acids in cardiac biopsies from heart transplantation patients." Circulation 110;1645-1649 (2004).

Harris, W.S., et al., "Comparison of the effects of fish and fish-oil capsules on the n-3 fatty acid content of blood cells and plasma phospholipids." Am J Clin Nutr 86:1621-5 (2007).

Harris, W.S., et al., "Omega-3 fatty acids and coronary heart disease risk: Clinical and mechanistic perspectives." Atherosclerosis 197:12-24 (2008).

Harris, W.S., et al., "Stearidonic acid increases the red blood cell and heart eicosapentaenoic acid content in dogs." Lipids 42:325-333 (2007).

Harris, W.S., et al., "Tissue n-3 and n-6 fatty acids and risk for coronary heart disease events." Atherosclerosis 193:1-10 (2007).

Hartweg, J., et al., "Potential impact of omega-3 treatment on cardiovascular disease in type 2 diabetes." Curr Opin Lipidol. 2009; 20:30-38.

Hawthorne, et al., "High dose eicosapentaenoic acid ethyl ester: effects on lipids and neutrophil leukotriene production in normal volunteers." Br. J. Clin. Pharmac. (1990), 30,187-194.

Hayashi et al., Decreases in Plasma Lipid Content and Thrombotic Activity by Ethyl Icosapentate Purified from Fish Oiles, Current Therapeutic Research, vol. 56, No. 1, Jan. 1995, pp. 24-31.

Hibbeln, J. R., et al., "Healthy intakes of n-3 and n-6 fatty acids: estimations considering worldwide diversity." Am J Clin Nutr. 83:1483S-93S (2006).

Hilpert, K.F., et al., "Postprandial effect of n-3 polyunsaturated fatty acids on apolipoprotein B-containing lipoproteins and vascular reactivity in type 2 diabetes." Am J Clin Nutr 85:369-76 (2007).

Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (2002).

Hirai, A., et al., (1982). The effects of the oral administration of fish oil concentrate on the release and the metabolism of [$^{14}$C] arachidonic acid and [$^{14}$C] eicosapentaenoic acid by human platelets. Thromb. Res. 28: 285-298.

Hirano, R., et al., "Regulation by long-chain fatty acids of the expression of cholesteryl ester transfer protein in HepG2 cells." Lipids. 2001; 36:401-406.

Holmeide, A. K., et al., "Oxidative degradation of eicosapentaenoic acid into polyunsaturated aldehydes." Tetrahedron 59:7157-7162 (2003).

(56) References Cited

OTHER PUBLICATIONS

Holub, B.J., PhD, "Fish Oils and Cardiovascular Disease", Canadian Medical Association Journal, 141(10):1063, Nov. 15, 1989.
Hombeck, M., et al., "Biosynthesis of the algal pheromone fucoserratene by the freshwater diatom *Asterionella formosa* (Bacillariophyceae)." Tetrahedron 54:11033-11042 (1998).
Hoskins et al., Combination use of statins and omega-3 fatty acids: an emerging therapy for combined hyperlipidemia, pp. 579-591—Abstract only.
Howe, P.R.C., et al., "Equal antithrombotic and triglyceride-lowering effectiveness of eicosapentaenoic acid-rich and docosahexaenoic acid-rich fish oil supplements." Lipids 34:S307-S308 (1999).
Huntingdon's Disease Drug Works, The DHA Dilemma, available at http://hddrugworks.org/index.php?option=com_content &task=view&id=185&Itemid=26, printed on Aug. 22, 2008.
Illingworth et al., "Comparative Effects of Lovastatin and Niacin in Primary Hypercholesterolemia. A Prospective Trial," Arch Intern med. 1994;154:1586-1595.
Inoue, I., et al., "Expression of peroxisome proliferator-activated receptor α (PPARα) in primary cultures of human vascular endothelial cells." Biochem. Biophys. Res. Comm., 246, 370-374 (1998).
Ishida, Y., et al., "α-Lipoic Acid and Insulin Autoimmune Syndrome." Diabetes Care, 30(9): 2240-41 (2007).
Isley, et al., "Pilot study of combined therapy with ω-3 fatty acids and niacin in atherogenic dyslipidemia," Journal of Clinical Lipidology (2007) 1, 211-217.
Jacobson et al. "Hypertriglyceridemia and Cardiovascular Risk Reduction", Clinical Therapeutics, vol. 29 pp. 763-777 (2007).
Jacobson, T. Secondary Prevention of Coronary Artery Disease with Omega-3 Fatty Acids. Am J Cardiol 2006; 98 [suppl]: 61i-70i.
Jacobson, T.A., "Role of n-3 fatty acids in the treatment of hypertriglyceridemia and cardiovascular disease." Am J Clin Nutr 87:1981S-90S (2008).
Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (2012).
Jenner, "Presymptomatic Detection of Parkinson's Disease". J Neural Transm Suppl, 1993; 40:23-36. (Abstract only).
Jialal, I., "Editorial: Remnant lipoproteins: measurement and clinical significance." Clinical Chemistry 48(2):217-219 (2002).
Jung, U.J., et al., "n-3 Fatty acids and cardiovascular disease: mechanisms underlying beneficial effects." Am J Clin Nutr 87: 2003S-9S (2008).
Kanayasu, T., et al., "Eicosapentaenoic acid inhibits tube formation of vascular endothelial cells in vitro." Lipids 26:271-276 (1991).
Katan, M. B., et al., "Kinetics of the incorporation of dietary fatty acids into serum cholesteryl esters, erythrocyte membranes, and adipose tissue: an 18-month controlled study." J. Lipid Res. 38: 2012-2022 (1997).
Katayama et al. Prog. Med.(2001) 21:457-467, translated from Japanese.
Kato, T., et al., "Palmitate impairs and eicosapentaenoate restores insulin secretion through regulation of SREBP-1c in pancreatic islets." Diabetes, 57(9):2382-2392 (2008) (published online May 5, 2008.).
Kawano, H., et al., (2002). Changes in aspects such as the collagenous fiber density and foam cell size of atherosclerotic lesions composed of foam cells, smooth muscle cells and fibrous components in rabbits caused by all-cis-5,8,11,14,17-icosapentaenoic acid. J. Atheroscler. Thromb. 9: 170-177.
Kawashima, H., et al., "Oral Administration of Dihomo-γ-Linolenic Acid Prevents Development of Atopic Dermatitis in NC/Nga Mice." Lipids 43:37-43 (2008).
Kelley, D. S., et al., "Docosahexaenoic Acid Supplementation Decreases Remnant-Like Particle-Cholesterol and Increases the (n-3) Index in Hypertriglyceridemic Men." J. Nutr. 138: 30-35 (2008).
Kelley, et al., "Docosahexaenoic acid supplementation improves fasting and postprandial lip profiles in hypertriglyceridemic men." The American Journal of Clinical Nutrition, 2007; 86: 324-333.
Kew, S., et al., "Effects of oils rich in eicosapentaenoic and docosahexaenoic acids on immune cell composition and function in healthy humans." Am J Clin Nutr 79:674-81 (2004).
Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (2008).
Kinsella, J.E., et al., "Dietary n-3 polyunsaturated fatty acids and amelioration of cardiovascular disease: possible mechanisms." Am J Clin Nutr 52:1-28 (1990).
Knopp et al., "Contrasting Effects of Unmodified and Time-Release Forms of Niacin on Lipoproteins in Hyperlipidemic Subjects: Clues to Mechanism of Action of Niacin," Northwest Lipid Research Clinic, Department of Medicine, School of Medicine, University of Washington, Seattle, 1985, pp. 642-650.
Kohno, M., et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (2001).
Kojima, T,. et al., "Long-term administration of highly purified eicosapentaenoic acid provides improvement of psoriasis." Dermatologica, 182:225-230 (1991).
Kosonen, O., et al., "Inhibition by nitric oxide-releasing compounds of E-selectin expression in and neutrophil adhesion to human endothelial cells." European Journal of Pharmacology 394:149-156 (2000).
Kris-Ehterton, P. M., et al., "Omega-3 Fatty Acids and Cardiovascular Disease—New Recommendations From the American Heart Association." Arterioscler Thromb Vasc Biol. 23:151-152 (2003).
Kris-Etherton, P.M., et al., "American Heart Association Nutrition Committee. Fish consumption, fish oil, omega-3 fatty acids, and cardiovascular disease." Circulation. 2002;106:2747-2757.
Ku, K., et al., "Beneficial Effects of to-3 Fatty Acid Treatment on the Recovery of Cardiac Function After Cold Storage of Hyperlipidemic Rats." Metabolism, 48(10):123-1209 (1999).
Kurabayashi, T., et al., "Eicosapentaenoic acid effect on hyperlipidemia in menopausal Japanese women." Obstet Gynecol 96:521-8 (2000).
Lai et al., "Suppression of Niacin-induced Vasodilation with an Antagonist to Prostaglandin D2 Receptor Subtype 1, clinical Pharmacology & Therapeutics, vol. 81, No. 6, Jun. 2007, pp. 849-857.
Laidlaw, M., et al., "Effects of supplementation with fish oil-derived n-3 fatty acids and γ-linolenic acid on circulating plasma lipids and fatty acid profiles in women." Am J Clin Nutr 77:37-42 (2003).
Larsen, L.N., et al., "Heneicosapentaenoate (21:5n-3): Its incorporation into lipids and its effects on arachidonic acid and eicosanoid Synthesis." Lipids 32:707-714 (1997).
Law, M.R., et al., "Quantifying effect of statins on low density lipoprotein cholesterol, ischaemic heart disease, and stroke: systematic review and meta-analysis." Br Med J. 2003;326:1423-1427.
Leaf, A., "Historical overview of n3 fatty acids and coronary heart disease." Am J Clin Nutr 87:1978S-80S. (2008).
Lee, J.H., et al., "Omega-3 fatty acids for cardioprotection." Mayo Clin Proc., 83(3):324-332 (2008).
Lee, K.W., et al., "The Role of Omega-3 Fatty Acids in the Secondary Prevention of Cardiovascular Disease", Q J Med, 96:465-480, 2003.
Lemaitre, R.N., et al., "n-3 Polyunsaturated fatty acids, fatal ischemic heart disease, and nonfatal myocardial infarction in older adults: the Cardiovascular Health Study." Am J Clin Nutr 77:319-25 (2003).
Leonard, B.E., Fundamentals of Psychopharmacology, pp. 186-187, 1997.
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials", pp. 51-68. 1999.
Li, D., et al., "Effect of dietary a-linolenic acid on thrombotic risk factors in vegetarian men." Am J Clin Nutr 69:872-82 (1999).

(56) References Cited

OTHER PUBLICATIONS

Li, H., et al., "EPA and DHA reduce LPS-induced inflammation responses in HK-2 cells: Evidence for a PPAR-γ-dependent mechanism." Kidney Int'l 67:867-74 (2005).
Lien, E.L., "Toxicology and safety of DHA." Prostaglandins Leukot Essent Fatty Acids. 2009;81:125-132.
Lin, Pao-Yen, M.D., et al. "A Meta-Analytic Review of Double-Blind, Placebo-Controlled Trials of Antidepressant Efficacy of Omega-3 Fatty Acids", Psychiatry, 1056-1061 (Jul. 2007).
Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (1995).
Lindsey, S., et al., "Low density lipoprotein from humans supplemented with n-3 fatty acids depresses both LDL receptor activity and LDLr mRNA abundance in HepG2 cells." J Lipid Res. 1992;33:647-658.
Lipitor (Pfizer, 2007).
Lohmussaar, E., et al., "ALOX5AP Gene and the PDE4D Gene in a Central European Population of Stroke Patients." Stroke, 36:731-736 (2005).
Lovaza® (omega-3-acid ethyl esters) Capsules, Prescribing information, 12 pgs., Jun. 2008, GlaxoSmithKline.
Lovaza (Smith Kline Beechum, Jul. 2009).
Lu, G., et al., "Omega-3 fatty acids alter lipoprotein subfraction distributions and the in vitro conversion of very low density lipoproteins to lowdensity lipoproteins." J Nutr Biochem. 1999;10:151-158.
Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (2009).
Luria, M. "Effect of Low-Dose Niacin on High-Density Lipoprotein Cholesterol and Total Cholesterol/High-Density Lipoprotein Cholesterol Ratio," Arch Intern Med 1988;148:2493-2495.
Madhavi, N., et al., "Effect of n-6 and n-3 fatty acids on the survival of vincristine sensitive and resistant human cervical carcinoma cells in vitro", Cancer Letters, vol. 84, No. 1, 1994, pp. 31-41.
Madsen, L., et al., "Eicosapentaenoic and Docosahexaenoic Acid Affect Mitochondrial and Peroxisomal Fatty Acid Oxidation in Relation to Substrate Preference." Lipids 34:951-963 (1999).
Maki, K.C., et al., "Baseline lipoprotein lipids and low-density lipoprotein cholesterol response to prescription omega-3 acid ethyl ester added to simvastatin therapy." Am J Cardiol. 2010;105:1409-1412.
Maki, PhD, et al., "Lipid Responses to a Dietary Docosahexaenoic Acid Supplement in Men and Women With Below Average Levels of High Density Lipoprotein Cholesterol." Journal of the American College of Nutrition, vol. 24, No. 3,189-199 (2005).
Mallat, Z., et al., "Apoptosis in the vasculature: mechanisms and functional importance." British Journal of Pharmacology 130:947-962 (2000).
Mallat, Z., et al., "Protective role of interleukin-10 in atherosclerosis." Circ. Res. 85:e17-e24 (1999).
Marangell, L. B., et al., "A Double-Blind, Placebo-Controlled Study of the Omega-3 Fatty Acid Docosahexaenoic Acid in the Treatment of Major Depression" Am J Psychiatry, 160(5):996-998, (May 2003).
Marckmann, P., "Fishing for heart protection." Am J Clin Nutr, 78:1-2 (2003).
Martin-Jadraque, R., et al., "Effectiveness of Low-Dose Crystalline Nicotinic Acid in Men With Low High-Density Lipoprotein Cholesterol Levels." Arch. Intern. Med., vol. 156, pp. 1081-1088 (May 27, 1996).
Mater, M.K., et al., "Arachidonic acid inhibits lipogenic gene expression in 3T3-L1 adipocytes through a prostanoid pathway." J. Lipid Res. 39:1327-1334 (1998).
Matsumoto, M., et al., "Orally administered eicosapentaenoic acid reduces and stabilizes atherosclerotic lesions in ApoE-deficient mice." Atherosclerosis, 197(2):524-533 (2008).

Matsuzawa, Y., et al., "Effect of Long-Term Administration of Ethyl Icosapentate (MND-21) In Myperlipaemic Patients," J. Clin Therapeutic & Medicines 1991; 7: 1801-16.
Mayatepek, E., et al., The Lancet, vol. 352, "Leukotriene C4-synthesis deficiency: a new inborn error of metabolism linked to a fatal developmental syndrome" pp. 1514-1517, Nov. 7, 1998.
McElroy, S.L., et al., "Clozapine in the Treatment of Psychotic Mood Disorders, Schizoaffective Disorder, and Schizophrenia", Journal of Clinical Psychiatry, vol. 52, No. 10, Oct. 1991, pp. 411-414.
McKenney, James et al., "Role of prescription omega-3 fatty acids in the treatment of Hypertriglyceridemia," Pharmacotherapy, May 2007 LNKD-Pubmed: 17461707, vol. 27, No. 5, pp. 715-728.
McMurchie, E.J., et al., "Incorporation and effects of dietary eicosapentaenoate (20 : 5( n-3)) on plasma and erythrocyte lipids of the marmoset following dietary supplementation with differing levels of linoleic acid." Biochimica et Biophysics Acta, 1045:164-173 (1990).
Menuet, R. et al., "Importance and management of dyslipidemia in the metabolic syndrome," American Journal of the Medical Sciences Dec. 2005 US, vol. 33, No. 6, pp. 295-302.
Merched, A.J., et al., "Atherosclerosis: evidence for impairment of resolution of vascular inflammation governed by specific lipid mediators." FASEB J. 22:3595-3606 (2008).
Mesa, M., "Effects of oils rich in Eicosapentaenoic and docosahexaenoic acids on the oxidizability and thrombogenicity of low-density lipoprotein," Artherosclerosis 175 (2004) 333-343.
Metcalf, R.G. et al., "Effect of dietary n-3 polyunsaturated fatty acids on the inducibility of ventricular tachycardia in patients with ischemic cardiomyopathy." Am J Cardiol 101:758-761 (2008).
Metcalf, R.G., et al., "Effects of fish-oil supplementation on myocardial fatty acids in humans." Am J Clin Nutr 85:1222-28 (2007).
Meyer, et al., "Dose-Dependent Effects of Docosahexaenoic Acid Supplementation on Blood Lipids in Statin-Treated Hyperlipidaemic Subjects." Lipids (2007) 42:109-115.
Meyers et al., Nicotinic acid induces secretion of prostaglandin D2 in human macrophages: An in vitro model of the niacin flush, Artherosclerosis 192 (2007) 253-258.
Mii, S., et al., "Perioperative use of eicosapentaenoic acid and patency of infrainguinal vein bypass: a retrospective chart review." Curr Ther Res Clin Exp. 68:161-174 (2007).
Miles, et al., "Effect of orlistat in overweight and obese patients with type 2 diabetes treated with metformin," Diabetes Care, Jul. 2002; 25(7):1123-1128.
Miller, M., et al., "Impact of lowering triglycerides on raising HDL-C in hypertriglyceridemic and non-hypertriglyceridemic subjects." International Journal of Cardiology 119:192-195 (2007).
Minihane, A.M., et al., "ApoE polymorphism and fish oil supplementation in subjects with an atherogenic lipoprotein phenotype." Arterioscler. Thromb. Vasc. Biol. 20:1990-1997 (2000).
Mishra, A., et al., "Oxidized omega-3 fatty acids inhibit NF-κB activation via a PPARα-Dependent Pathway." Arterioscler Thromb Vasc Biol. 24:1621-1627 (2004).
Mita, T. et al., Eicosapentaenoic acid reduces the progression of carotid intima-media thickness in patients with type 2 diabetes, Atherosclerosis 191 (2007) 162-167.
Mizota M, Katsuki Y, Mizuguchi K, Endo S, Miyata H, Kojima M, Kanehiro H et al. "Pharmacological studies of eicosapentaenoic acid ethylester (EPA-E) on high cholesterol diet-fed rabbits," Nippon Yakurigaku Zasshi 1988; 91:255-66.
Mizota M, Katsuki Y, Mizuguchi K, Endo S, Miyata H, Kojima M, Kanehiro H et al. "The effects of eicosapentaenoic acid ethylester (EPA-E) on arterial thrombosis in rabbits and vascular lesions in rats," Nippon Yakurigaku Zasshi 1988; 91:81-9.
Mizuguchi K, Yano T, Kojima M, Tanaka Y, Ishibashi M, Masada A, Sato M et al. "Hypolipidemic effect of ethyl all-cis-5,8,11,14,17-eicosapentaenoate (EPA-E) in rats," Jpn J Pharmacol 1992; 59:3307-12.
Mizuguchi, K., et al., "Ethyl all-cis-5,8,11,14,17-icosapentaenoate modifies the biochemical properties of rat very low-density lipoprotein." European Journal of Pharmacology, 231:221-227 (1993).

(56) References Cited

OTHER PUBLICATIONS

Mizuguchi, K., et al., "Mechanism of the lipid-lowering effect of ethyl all-cis-5,8,11,14,17-icosapentaenoate." European Journal of Pharmacology, 231:121-127 (1993).

Mora, S., et al., "LDL particle subclasses, LDL particle size, and carotid atherosclerosis in the Multi-Ethnic Study of Atherosclerosis (MESA)." Atherosclerosis. 2007;192:211-217.

Mori TA, Woodman RJ. "The independent effects of eicosapentaenoic acid and docosahexaenoic acid on cardiovascular risk factors in humans," Curr Opin Clin Nutr Metab Care 2006; 9:95-104.

Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 2000; 71:1085-1094.

Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781, 2003.

Mori, T., et al., "Docosahexaenoic Acid but Not Eicosapentaenoic Acid Lowers Ambulatory Blood Pressure and Heart Rate in Humans" Hypertension, (Aug. 1999).

Morita, I., et al., "Effects of purified eicosapentaenoic acid on arachidonic acid metabolism in cultured murine aortic smooth muscle cells, vessel walls and platelets." Lipids 18:42-490 (1983).

Morrow et al., Release of Markedly Increased Quantities of Prostaglandin D2 In Vivo in Humans Following the Administration of Nicotinic Acid, Prostaglandins, Aug. 1989, vol. 38, No. 2., pp. 263-274.

Morton, R.E., "Specificity of lipid transfer protein for molecular species of cholesteryl ester." J Lipid Res. 1986;27:523-529.

Mosher LR et al., "Nicotinic Acid Side Effects and Toxicity: A review," Am J Psychiat. 1970; 126: 1290-1296.

Mostad, I.L, et al., "Effects of n-3 fatty acids in subjects with type 2 diabetes: reduction of insulin sensitivity and time-dependent alteration from carbohydrate to fat oxidation." Am J Clin Nutr 84:540-50 (2006).

Mozaffarian, "JELIS, fish oil, and cardiac events," The Lancet, vol. 369, Mar. 31, 2007, pp. 1062-1063.

Mozaffarian, D., "Fish and n-3 fatty acids for the prevention of fatal coronary heart disease and sudden cardiac death." Am J Clin Nutr, 87:1991S-6S (2008).

Mozaffarian, D., et al., "Dietary fish and ω-3 fatty acid consumption and heart rate variability in US adults." Circulation, 117:1130-1137 (2008).

Naba, H., et al., "Improving effect of ethyl eicosapentanoate on statin-induced rhabdomyolysis in Eisai hyperbilirubinemic rats." Biochemical and Biophysical Research Communications, 340:215-220 (2006).

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (1998).

Nakamura, H., et al., "Evaluation of ethyl icosapentate in the treatment of hypercholesterolemia in kidney transplant recipients." Transplantation Proceedings, 30:3047-3048 (1998).

Nakamura, N., et al., "Joint effects of HMG-CoA reductase inhibitors and eicosapentaenoic acids on serum lipid profile and plasma fatty acid concentrations in patients with hyperlipidemia", International Journal of Clinical and Laboratory Research, Springer, Berlin, DE LNKD-DOI: 10.1007/S005990050057, vol. 29, No. 1, Mar. 1, 1999, pp. 22-25.

Nambi, V., et al., "Combination therapy with statins and omega-3 fatty acids." Am J Cardiol 98:34i-38i (2006).

Nasa, et al., "Long-Term Supplementation With Eicosapentaenoic Acid Salvages Cardiomyocytes From Hypoxia/Reoxygenation-Induced Injury in Rats Fed With Fish-Oil-Deprived Diet," Jpn. J. Pharmacol. 77, 137-146 (1998).

Nattel, S., et al., "Atrial remodeling and atrial fibrillation: Mechanisms and implications." Circ Arrhythmia Electrophysiol, 1:62-73 (2008).

Negre-Salvayre, A., et al., "Advanced lipid peroxidation end products in oxidative damage to proteins. Potential role in diseases and therapeutic prospects for the inhibitors." British Journal of Pharmacology 153:6-20 (2008).

Nelson, G. J., et al., "The Effect of Dietary Docosahexaenoic Acid on Plasma Lipoproteins, and Tissue Fatty Acids Composition in Humans", Lipids, AOCS Press, 32(11):1137-1146, 1997.

Nemets, B., "Addition of Omega-3 Fatty Acid to Maintenance Medication Treatment for Recurrent Unipolar Depressive Disorder" Am J Psychiatry, 159(3):477-479 (Mar. 2002).

Nenseter, MS et al., "Effect of dietary supplementation with n-3 polyunsaturated fatty acids on physical properties and metabolism of low density lipoprotein in humans," Arterioscler. Thromb. Vasc. Biol. 1992; 12;369-379.

Nestel, et al., "The n-3 fatty acids eicosapentaenoic acid and docosahexaenoic acid increase systemic arterial compliance in humans," Am J Clin Nutr 2002; 76:326-30.

Nestel, P.J., "Effects of N-3 fatty acids on lipid metabolism." Ann Rev Nutr. 1990;10:149-167.

Nishikawa M. et al., "Effects of Eicosapentaenoic acid (EPA) on prostacyclin production in diabetics. GC/MS analysis of PG12 and PG13 levels" Methods Find Exp Clin Pharmacol. 19(6):429-33 (Jul.-Aug. 1997).

Nobukata, H., et al., "Age-related changes in coagulation, fibrinolysis, and platelet aggregation in male WBN/Kob rats." Thrombosis Research 98: 507-516 (2000).

Nobukata, H., et al., "Long-term administration of highly purified eicosapentaenoic acid ethyl ester prevents diabetes and abnormalities of blood coagulation in male WBN/Kob rats." Metabolism, 49(12): 912-919 (2000).

Nobukata, H., et al., "Long-term administration of highly purified eicosapentaenoic acid ethyl ester improves the dysfunction of vascular endothelial and smooth muscle cells in male WBN/Kob rats." Metabolism, 49(12): 1588-1591 (2000).

Nourooz-Zadeh, J., et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (2005).

Nozaki S. et al., "Effects of purified Eicosapentaenoic acid ethyl ester on plasma lipoproteins in primary hypercholesterolemia" Int J Vitam Nutr Res. 62(3):256-60 (1992).

O'Donnell, C.J., et al., "Leukocyte telomere length and carotid artery intimal medial thickness—the Framingham heart study." Arteriosclerosis, Thrombosis, and Vascular Biology.28:1165-1171 (2008).

Obata, et al., (1999) Eicosapentaenoic acid inhibits prostaglandin $D_2$ generation by inhibiting cyclo-oxygenase in cultured human mast cells. Clin. & Experimental Allergy 29: 1129-1135.

Oh, Robert C et al., Management of Hypertriglyceridemia, American Family Physician, May 1, 2007, LNKD-PUBMED: 17508532, vol. 75, No. 9, pp. 1365-1371.

Okuda, Y., et al., (1997) Eicosapentaenoic acid enhances nitric oxide production by cultured human endothelial cells. Biochem. Biophys. Res. Commun. 232: 487-491 (1997).

Okuda, Y., et al., "Long-term effects of eicosapentaenoic acid on diabetic peripheral neuropathy and serum lipids in patients with type II diabetes mellitus." Journal of Diabetes and Its Complications 10:280-287 (1996).

Okumura, T., et al., "Eicosapentaenoic acid improves endothelial function in hypertriglyceridemic subjects despite increased lipid oxidizability." Am J Med Sci 324(5):247-253 (2002).

Oliw, E.H., et al., "Biosynthesis of prostaglandins from 17(18)epoxy-eicosatetraenoic acid, a cytochrome P-450 metabolite of eicosapentaenoic acid." Biochimica el Biophysica Acta, 1126 (1992) 261-268.

Ona, V.O., et al., NATURE, vol. 399, "Inhibition of caspase-1 slows disease progression in a mouse model of Huntington's disease," pp. 263-267, May 20, 1999.

Ozawa A, Nakamura E, Jinbo H. Fujita T, Hirai A, Terano T, Hamazaki T et al. "Measurement of higher lipids in the fractions of

(56) References Cited

OTHER PUBLICATIONS human red blood cell membranes, blood platelets and plasma, using thin layer chromatography and gas chromatography," Bunseki Kagaku 1982; 32:174-8.

Park, Y., et al., "Omega-3 fatty acid supplementation accelerates chylomicron triglyceride clearance." J. Lipid Res. 44:455-463 (2003).

Pedersen, T., et al., "Randomised trial of cholesterol lowering in 4444 patients with coronary heart disease: the Scandinavian Simvastation Survival Study (4S)", The Lancet, No. 19, 1994, vol. 344, 8934, p. 1383-1389.

Peet, M., et al., "A Dose-Ranging Study of the Effects of Ethyl-Eicosapentaenoate in Patients with Ongoing Depression Despite Apparently Adequate Treatment with Standard Drugs", Arch Gen Psychiatry, 59:913-919, (Oct. 2002).

Peet, M., et al., Phospholipid Spectrum Disorder in Psychiatry pp. 1-19, 1999.

Piccini, Monica, et al., Genomics, vol. 47, "FACL4, a new gene encoding long-chain acyl-CoA synthetase 4, is deleted in a family with Alport syndrome, elliptocytosis, and mental retardation," pp. 350-358, 1998.

Pike, N., "Flushing out the role of GPR109A (HM74a) in the clinical efficacy of nicotinic acid," The Journal of Clinical Investigation, vol. 115, No. 12, Dec. 2005, pp. 3400-3403.

Pownall, H.J., et al., "Correlation of serum triglyceride and its reduction by ω-3 fatty acids with lipid transfer activity and the neutral lipid compositions of high-density and low-density lipoproteins." Atherosclerosis 143:285-297 (1999).

Press Release from Mochida Pharmaceutical Col., Ltd.: Conclusion of Distributorship Agreement Concerning Switch-OTC Drug for Hyperlipidemia Treatment, Epadel, published Apr. 30, 2009.

Press Release: Amarin Corporation Says Huntington's Disease Drug Failed in Trials, http://www.fiercebiotech.com/node/6607/print (Apr. 24, 2007) Printed on Aug. 22, 2008.

Product brochure: "PLUSEPA® "Super Critically" Different from Other Omega-3 Fish Oil Supplements for Depression and ADHD," by Minami Nutrition (Apr. 2009, pp. 1-6).

Puri, B., et al., "Eicosapentaenoic Acid in Treatment-Resistant Depression Associated with Symptom Remission, Structural Brain Changes and Reduced Neuronal Phospholipid Turnover," Int J Clinical Practice 2001; 55:560-563.

Puri, B., et al., Archives of General Psychiatry, No. 55, "Sustained remission of positive and negative symptoms of schizophrenia following treatment with eicosapentaenoic acid," pp. 188-189, 1998.

Puri, B.K., et al., "Ethyl-EPA in Huntington Disease: A Double-Blind, Randomized, Placebo-Controlled Trial", Neurology 65:286-292, (2005).

Qi, K., et al., "Omega-3 fatty acid containing diets decrease plasma triglyceride concentrations in mice by reducing endogenous triglyceride synthesis and enhancing the blood clearance of triglyceride-rich particles." Clinical Nutrition 27(8):424-430 (2008).

Raitt, M.H., et al., "Fish oil supplementation and risk of ventricular tachycardia and ventricular fibrillation in patients with implantable defibrillators—a randomized controlled trial." JAMA. 293(23):2884-2891 (2005).

Rambjor, Gro S., et al., "Eicosapentaenoic Acid is Primarily Responsible for Hypotrigylceridemic Effect of Fish Oil in Humans", Fatty Acids and Lipids from Cell Biology to Human Disease: Proceedings of the $2^{nd}$ international Congress of the ISSFAL (International Society for the Study of Fatty Acids and Lipids, AOCS Press, 31:S-45-S-49, 1996.

Reiffel, J.A., et al., "Antiarrhythmic effects of omega-3 fatty acids." Am J Cardiol 98:50i-60i (2006).

Riediger, N.D., et al., "A systemic review of the roles of n-3 fatty acids in health and disease." J Am Diet Assoc. 109:668-679. (2009).

Rise, P., et al., "Effects of simvastatin on the metabolism of polyunsaturated fatty acids and on glycerolipid, cholesterol, and de novo lipid synthesis in THP-1 cells." J. Lipid Res. 38:1299-1307 (1997).

Roach, P.D., et al., "The effects of dietary fish oil on hepatic high density and low density lipoprotein receptor activities in the rat." FEBS Lett. 1987;222: 159-162.

Robinson, J.G., et al., "Meta-analysis of the relationship between non-high-density lipoprotein cholesterol reduction and coronary heart risk." J Am Coll Cardiol. 2009;53: 316-322.

Roche, H.M., et al., "Effect of long-chain n-3 polyunsaturated fatty acids on fasting and postprandial triacylglycerol metabolism." Am J Clin Nutr 71:232S-7S (2000).

Roche, H.M., et al., "Long-chain n-3 polyunsaturated fatty acids and triacylglycerol metabolism in the postprandial state." Lipids 34: S259-S265 (1999).

Rogers, P. J., "No effect of n-3 long-chain polyunsaturated fatty acid (EPA and DHA) supplementation on depressed mood and cognitive function: a randomised controlled trial" British Journal of Nutrition, 99:421-431, (2008).

Rodriguez, Y., et al., "Long-chain ω6 polyunsaturated fatty acids in erythrocyte phospholipids are associated with insulin resistance in non-obese type 2 diabetics." Clinica Chimica Acta 354:195-199 (2005).

Rubins, H.B., et al., (1995). Distribution of lipids in 8,500 men with coronary artery disease: Department of Veterans Affairs HDL Intervention Trial Study Group. Am. J. Cardiol. 75: 1196-1201.

Rubins, H.B., et al., (1999). Gemfibrozil for the prevention of coronary heart disease in men with low levels of high-density lipoprotein cholesterol. Veterans Affairs HDL-C intervention trial study group. N. Eng. J. Med. 341: 410-418.

Ruiz-Narváez, E.A., et al., "Abdominal obesity and hyperglycemia mask the effect of a common APOC3 haplotype on the risk of myocardial infarction." Am J Clin Nutr 87:1932-8 (2008).

Rustan, A.C., et al., "Eicosapentaenoic acid inhibits cholesterol esterification in cultured parenchymal cells and isolated microsomes from rat liver." J. Bio. Chem. 263(17):8126-32 (1988).

Rustan, A.C., et al., "Eicosapentaenoic acid reduces hepatic synthesis and secretion of triacylglycerol by decreasing the activity of acyl-coenzyme A:1,2-diacylglycerol acyltransferase." J. Lipid Res. 29:1417-1426 (1988).

Rustan, A.C., et al., "Postprandial decrease in plasma unesterified fatty acids during n-3 fatty acid feeding is not caused by accumulation of fatty acids in adipose tissue." Biochimica et Biophysica Acta 1390.245-25 (1998).

Ryan, A.M., et al., "Enteral nutrition enriched with eicosapentaenoic acid (EPA) preserves lean body mass following esophageal cancer surgery: results of a double-blinded randomized controlled trial." Ann Surg 249:355-363 (2009).

Ryan, A.S., et al., "Clinical overview of algal-docosahexaenoic acid: effects on triglyceride levels and other cardiovascular risk factors." Am J Ther. 2009;16:183-192.

Sacks, Frank M., "The apolipoprotein story," Atherosclerosis Supplements 7 (2006) 23-27.

Saito et al., Effects of EPA on coronary artery disease in hypercholesterolemic patients with multiple risk factors: Sub-analysis of primary prevention cases from the Japan EPA Lipid Intervention Study (JELIS), (Atherosclerosis (2008) 200:135-140).

Saito, J., et al., "Mechanisms of enhanced production of PGI2 in cultured rat vascular smooth muscle cells enriched with eicosapentaenoic acid." Atherosclerosis 131: 219-228 (1997).

Samuels, A., et al., Office Practice of Neurology, Chapter 122, Huntington's Disease, pp. 654-655, 1996.

Sanders, et al., "Influence of an algal triacylglycerol containing docosahexaenoic acid (22:6n-3) and docosapentaenoic acid (22:5n-6) on cardiovascular risk factors in healthy men and women," British Journal of Nutrition (2006), 95, 525-531.

Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (2006).

Sanders, T.A., et al., "Triglyceride-lowering effect of marine polyunsaturates in patients with hypertriglyceridemia." Arterioscler. Thromb. Vasc. Biol. 5:459-465 (1985).

Sanders, T.A.,et al., "Influence of n-3 fatty acids on blood lipids in normal subjects" Journal of Internal Medicine. 225:99-104,1989.

(56) References Cited

OTHER PUBLICATIONS

Sasaki, Y.F., et al., "Bio-anticlastogenic effects of unsaturated fatty acids included in fish oil—docosahexaenoic acid, docosapentaenoic acid, and eicosapentaenoic acid—in cultured Chinese hamster cells." Mutation Research, 320: 9-22 (1994).

Sato, M., et al., "General Pharmacological Studies on 5 8 11 14 17 Eicosapentaenoic Acid Ethyl Ester EPA-E", Folia Pharmacol JPN, (1989) 94 (1), 35-48.

Satoh, N., et al., "Purified eicosapentaenoic acid reduces small dense LDL, remnant lipoprotein particles, and C-reactive protein in metabolic syndrome." Diabetes Care, 30(1): 144-146 (2007).

Schaefer, E.J., et al., "Effects of eicosapentaenoic acid, docosahexaenoic acid, and olive oil on cardiovascular disease risk factors [abstract 20007]." Circulation. 2010;122:A20007.

Schectman, G & Hiatt, J., (1996). Drug therapy for hypercholesterolemia in patients with cardiovascular disease: factors limiting achievement of lipid goals. Am. J. Med. 100: 197-204.

Schectman, G., et al., "Dietary fish oil decreases low-density-lipoprotein clearance in nonhuman primates." Am J Clin Nutr. 1996;64:215-221.

Schectman, G., et al., "Heterogeneity of Low Density Lipoprotein Responses to Fish-Oil Supplementation in Hypertriglyceridemic Subjects." Arterioscler. Thromb. Vasc. Biol. 9:345-354 (1989).

Schmidt, E.B., et al., "Lipoprotein-associated phospholipase A2 concentrations in plasma are associated with the extent of coronary artery disease and correlate to adipose tissue levels of marine n-3 fatty acids." Atherosclerosis 196: 420-424 (2008).

Schmitz, G., et al., "The opposing effects of n-3 and n-6 fatty acids." Progress in Lipid Research, 47:147-155 (2008).

Schwarz, S., et al., "Lycopene inhibits disease progression in patients with benign prostate hyperplasia." J. Nutr. 138: 49-53 (2008).

Serhan, C.N., et al., "Resolvins: A family of bioactive products of omega-3 fatty acid transformation circuits initiated by aspirin treatment that counter proinflammation signals." J. Exp. Med. 196:1025-1037 (2002).

Shah, S., et al., "Eicosapentaenoic Acid (EPA) as an Adjunct in the Treatment of Schizophrenia", Schizophrenia Research, vol. 29, No. 1/02, Jan. 1998.

Shan, Z., et al., "A combination study of spin-trapping, LC/ESR and LC/MS on carbon-centred radicals formed from lipoxygenase-catalysed peroxidation of eicosapentaenoic acid." Free Radical Research, 43(1):13-27 (2009).

Shimizu, H., et al., "Long-term effect of eicosapentaenoic acid ethyl (EPA-E) on albuminuria of non-insulin dependent diabetic patients." Diabetes Research and Clinical Practice 28: 35-40 (1995).

Shinozaki K. et al., "The long-term effect of Eicosapentaenoic acid on serum levels of lipoprotein (a) and lipids in patients with vasciular disease" J Atheroscler Thromb. 2(2):207-9 (1996).

Sierra, S., et al., "Dietary eicosapentaenoic acid and docosahexaenoic acid equally incorporate as decosahexaenoic acid but differ in inflammatory effects." Nutrition 24: 245-254 (2008).

Silvers, K. M., et al., "Randomised double-blind placebo-controlled trial of fish oil in the treatment of depression," Prostagandins, Leukotrienes and Essential Fatty Acids. 72:211-218 (2005).

Simoens, C.M., et al., "Inclusion of 10% fish oil in mixed medium-chain triacylglycerol—longchain triacylglycerol emulsions increases plasma triacylglycerol clearance and induces rapid eicosapentaenoic acid (20:5n-3) incorporation into blood cell phospholipids." Am J Clin Nutr 88: 282-8 (2008).

Simon, J.A., et al., "Serum Fatty Acids and the Risk of Coronary Heart Disease", American Journal of Epidemiology, 142(5):469-476, 1995.

Singer, Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (2005) Germany.

Singh, R.B., et al., "Randomized, double-blind, placebo-controlled trial of fish oil and mustard oil in patients with suspected acute myocardial infarction: the Indian experiment of infarct survival—4." Cardiovascular Drugs and Therapy 11:485-491 (1997).

Sirtori, C.R., et al., "One-year treatment with ethyl esters of n-3 fatty acids in patients with hypertriglyceridemia and glucose intolerance—Reduced triglyceridemia, total cholesterol and increased HDL-C." Atherosclerosis 137: 419-427 (1998).

Skinner JS, Cooper A, & Feder GS and on behalf of the Guideline Development Group. "Secondary prevention for patients following a myocardial infarction; summary of Nice guidance," Heart 2007; 93:862-864.

Smith et al., Pharmacokinetics and Pharmacodynamics of Epoetin Delta in Two Studies in Health Volunteers and Two Studies in Patients with Chronic Kidney Disease, Clinical Therapeutics/vol. 29, No. 7, 2007, pp. 1368-1380.

Sohma, R., et al., "Protective effect of n-3 polyunsaturated fatty acid on primary culture of rat hepatocytes without glycemic alterations." Journal of Gastroenterology and Hepatology 22: 1965-1970 (2007).

Spector, A.A., "Arachidonic acid cytochrome P450 epoxygenase pathway." Journal of Lipid Research, 50: S52-S56 (2009) (published online on Oct. 23, 2008.).

Spector, A.A., et al., "Epoxyeicosatrienoic acids (EETs): metabolism and biochemical function." Progress in Lipid Research 43: 55-90 (2004).

Springer, T.A., "Traffic signals for lymphocyte recirculation and leukocyte emigration: the multistep paradigm." Cell, 76: 301-314 (1994).

Squires et al., Low-Dose, Time-Release Nicotinic Acid: Effects in Selected Patients With Low Concentrations of High-Density Lipoprotein Cholesterol, May Clin Proc 67:855-860, 1992.

Srinivas, et al., "Controlled release of lysozyme from succinylated gelatin microspheres," J. Biomater. Sci., Polymer Ed., vol. 12(2):137-148 (2001).

Stalenhoef, A.F.H., et al., "The effect of concentrated n-3 fatty acids versus gemfibrozil on plasma lipoproteins, low density lipoprotein heterogeneity and oxidizability in patients with hypertrygliceridemia." Atherosclerosis 153: 129-138 (2000).

Stark, K.D. & Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-773 (2004).

Stark, K.D., "The percentage of n-3 highly unsaturated fatty acids in total HUFA as a biomarker for omega-3 fatty acid status in tissues." Lipids 43:45-53 (2008).

Stark, K.D., et al., "Effect of a fish-oil concentrate on serum lipids in postmenopausal women receiving and not receiving hormone replacement therapy in a placebo-controlled, double-blind trial." Am J Clin Nutr 72:389-94 (2000).

Stoll, A.L., et al., Arch. Gen. Psychiatry, vol. 56, "Omega 3 Fatty Acids in Bipolar Disorder", pp. 407-412, May 1999.

Su, K. P., et al. "Omega-3 Fatty Acids in Major Depressive Disorder A Preliminary Double-Blind, Placebo-Controlled Trial" European Neuropsychopharmacology, 13:267-271 (2003).

Sugiyama, E., et al., "Eicosapentaenoic acid lowers plasma and liver cholesterol levels in the presence of peroxisome proliferators-activated receptor alpha." Life Sciences, 83:19-28 (2008).

Superko et al., "Lipid Management to Reduce Cardiovascular Risk: A New Strategy is Required," Circulation 2008, 117:560-568.

Surette, M.E., et al., "Dependence on dietary cholesterol for n-3 polyunsaturated fatty acidinduced changes in plasma cholesterol in the Syrian hamster." J Lipid Res. 1992;33:263-271.

Surette, M.E., et al., "Evidence for mechanisms of the hypotriglyceridemic effect of n-3 polyunsaturated fatty, acids." Biochimica et Biophysic Acta, 1126: 199-205 (1992).

Tamura, et al., "Study of the Clinical Usefulness of Ethyl Icosapentate (MND-21) in Long-Term Treatment of Hyperlipaemic Patients." J Clin Thera & Medicines 1991; 7:1817-1834.

Tanaka, K.T., et al., "Reduction in the recurrence of stroke by eicosapentaenoic acid for hypercholesterolemic patients—Subanalysis of the JELIS trial." Stroke, 39(7):2052-8 (2008).

Tatarczyk, et al., "Analysis of long-chain ω-3 fatty acid content in fish-oil supplements," Wien Klin Wochenschr (2007) 119/13-14: 417-422.

Taylor et al., Arterial Biology for the Investigation of the Treatment Effects of Reducing Cholesterol (ARBITER) 2: A Double-Blind,

(56) References Cited

OTHER PUBLICATIONS

Placebo-Controlled Study of Extended-Release Niacin on Atherosclerosis Progression in Secondary Prevention Patients Treated With Statins, Circulation 2004;110;3512-3517.
Tedgui, A., et al., "Anti-inflammatory mechanisms in the vascular wall." Circ. Res. 88:877-887 (2001).
Terano, et al., "Effect of Oral Administration of Highly Purified Eicosapentaenoic Acid on Platelet Function, Blood Vicosity and Red Cell Deformability in Healthy Human Subjects," Atherosclerosis, 46 (1983) 321-331.
Theilla, M., et al., "A diet enriched in eicosapentanoic acid, gamma-linolenic acid and antioxidants in the prevention of new pressure ulcer formation in critically ill patients with acute lung injury: A randomized, prospective, controlled study." Clinical Nutrition 26: 752-757 (2007).
Thies, F., et al., "Association of n-3 polyunsaturated fatty acids with stability of atherosclerotic plaques: a randomised controlled trial." Lancet 361: 477-85 (2003).
Thies, F., et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (2001).
Tirosh et al., "Changes in Triglyceride Levels and Risk for Coronary Heart Disease in Young Men," 2007 American College of Physicians, pp. 377-385.
Torrejon, C. et al., "n-3 Fatty acids and cardiovascular disease: Actions and molecular mechanisms," Prostaglandins Leukotrienes & Essent. Fatty Acids (2007), doi:10.1016/j.plefa.2007.10.014.
TREND-HD Investigators, Randomized controlled trial of ethyl-eicosapentaenoic acid in Huntington disease: the TREND-HD study, Arch Neurol. 2008, vol. 65(12): 1582-9.
Tsuruta K., et al., "Effects of purified eicosapentaenoate ethyl ester on fibriolytic capacity in patients with stable coronary artery disease and lower extremity ischaemia" Coron Artery Dis. 7(11):837-42 (Nov. 1996).
Tungsiripat, et al., "Dyslipidemia in HIV patients," Cleveland Clinic Journal of Medicine, v. 72, No. 12, Dec. 2005.
Ullian, M.E., "Fatty acid inhibition of angiotensin II-stimulated inositol phosphates in smooth muscle cells." Am J Physiol Heart Circ Physiol (Nov. 1996).
Urakaze, M., et al., "Infusion of emulsified trieicosapentaenoylglycerol into rabbits. The effects on platelet aggregation, polymorphonuclear leukocyte adhesion, and fatty acid composition in plasma and platelet phosphollpids", Thromb. Res. (1986) 44(5), pp. 673-682.
US Food and Drug Administration and Dept of Health and Human Services. Substances affirmed as generally recognized as safe: Menhaden Oil. Fed Register 1997; 62:30751-30757.
Vaddadi, K. S., et al., "A Randomised, Placebo-Controlled, Double-Blind Study of Treatment of Huntington's Disease with Unsaturated Fatty Acids" Clinical Neuroscience and Neuropathology, 13(1):29-33 (Jan. 2002).
Van der Steeg, W.A., et al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (2008).
Vasudevan et al., "Effective Use of Combination of Lipid Therapy", Curr. Atheroscl. Rep., vol. 8, pp. 76-84 (2006).
Vedin, I., et al., "Effects of docosahexaenoic acid-rich n-3 fatty acid supplementation on cytokine release from blood mononuclear leukocytes: the OmegAD study." Am J Clin Nutr 87:1616-22 (2008).
Vidgren, H.M., et al., "Incorporation of n-3 fatty acids into plasma lipid fractions, and erythrocyte membranes and platelets during dietary supplementation with fish, fish oil, and docosahexaenoic acid-rich oil among healthy young men." Lipids 32: 697-705 (1997).
Volcik, K.A., et al., "Peroxisome proliferator-activated receptor αgenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (2008).

Von Schacky, C., "A review of omega-3 ethyl esters for cardiovascular prevention and treatment of increased blood triglyceride levels." Vascular Health and Risk Management 2(3): 251-262 (2006).
Von Schacky, C., et al., "The Effect of Dietary ω-3 Fatty Acids on Cornoray Atherosclerosis: A Randomized, Double-Blind, Placebo-Controlled Trial", American College of Physicians—American Society of Internal Medicine, 130(7):554-562, 1999.
Wada, M., et al., "Enzymes and receptors of prostaglandin pathways with arachidonic acid-derived versus eicosapentaenoic acid-derived substrates and products." J. Biol. Chem. 282(31): 22254-22266 (2007).
Walldius, G., et al., "Editorial: Rationale for using apolipoprotein B and apolipoprotein A-I as indicators of cardiac risk and as targets for lipid-lowering therapy." European Heart Journal 26, 210-212 (2005).
Wander, R.C., et al., "Influence of long.chain polyunsaturated fatty acids on oxidation of low density lipoprotein." Prostaglandins, Leukotrienes and Essential Fatty Acids 59(2):143-151 (1998).
Wang, C., et al., "n-3 Fatty acids from fish or fish-oil supplements, but not α-linolenic acid, benefit cardiovascular disease outcomes in primary- and secondary-prevention studies: a systematic review." Am J Clin Nutr 84:5-17 (2006).
Wang, L., et al., "Triglyceride-rich lipoprotein lipolysis releases neutral and oxidized FFAs that induce endothelial cell inflammation." J. Lipid Res. 50:204-213 (2009).
Warren, S.T., Science, vol. 271, "The Expanding World of Trinucleotide Repeats", pp. 1374-1375, Mar. 8, 1996.
Watanabe, I., et al., "Usefulness of EPA-E (eicosapentaenoic acid ethyl ester) in preventing neointimal formation after vascular injury", Kokyu to Junkan (1994), 42(7), pp. 673-677.
Weaver, K.L., et al., "Effect of Dietary Fatty Acids on Inflammatory Gene Expression in Healthy Humans." J. Biol. Chem., 284(23): 15400-15407 (2009) (published online Apr. 9, 2009.).
Weber, P., "Triglyceride-lowering effect of n-3 long chain polyunsaturated fatty acid: eicosapentaenoic acid vs. docosahexaenoic acid." Lipids 34: S269 (1999).
Westerveld H.T. et al., "Effects of low-dose EPA-E on glycemic control, lipid profile, lipoprotein(a), platelet aggretation, viscosity, and platelet and vessel wall interaction in NIDDM" Diabetes Care 16(5):683-8 (May 1993).
Westphal, S., et al., "Postprandial chylomicrons and VLDLs in severe hypertriacylglycerolemia are lowered more effectively than are chylomicron remnants after treatment with n23 fatty acids." Am J Clin Nutr 71:914-20 (2000).
Whelan, J., et al., "Evidence that dietary arachidonic acid increases circulating triglycerides." Lipids 30, 425-429 (1995).
Wierzbicki, A.S., "Editorial: Newer, lower, better? Lipid drugs and cardiovascular disease—the continuing story." Int J Clin Pract, 61(7):1064-1067 (2007).
Wierzbicki, A.S., "Editorial: Raising HDL-C: back to the future?" Int J Clin Pract, 61(7): 1069-1071 (2007).
Willumsen, N. et al., Biochimica et Biophysica Acta. vol. 1369, "On the effect of 2-deuterium- and 2-methyl-eicosapentaenoic acid derivatives on triglycerides, peroxisomal beta-oxidation and platelet aggregation in rats," pp. 193-203, 1998.
Willumsen, N., et al., "Eicosapentaenoic acid, but not docosahexaenoic acid, increased, mitochondrial fatty acid oxidation and upregulates 2,3-dienoyl-CoA reductase gene expression in rats." Lipids, 31:579-592 (1996).
Wilson Omega 3 fish oil: EPA versus DHA (Dietivity.com, 2006, 1-16).
Wilt, V.M. & Gumm, J.G. (1997). "Isolated" low high-density lipoprotein cholesterol. Ann. Pharmacol. 31: 89-97.
Wink et al., Effect of very-low-dose niacin on high-density lipoprotein in patients undergoing long-term statin therapy, Am Heart J 2002;143:514-8.
Wojenski, C.M., et al., "Eicosapentaenoic acid ethyl ester as an antithrombotic agent: comparison to an extract of fish oil." Biochimica et Biophysica Acta. 1081:33-38 (1991).
Wong, S.H., et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (1989).

(56) References Cited

OTHER PUBLICATIONS

Woodman, R. J., et al., "Effects of Purified Eicoaspentaenoic and Docosahexaenoic Acids on Glycemic Control, Blood Pressure, and Serum Lipids in Type 2 Diabetic Patients with Treated Hypertension" The American Journal of Clinical Nutrition: Official Journal of the American Society for Clinical Nutrition, Inc. 76(5):1007-1015 (Nov. 1, 2002).

Woodman, R.J., et al., "Effects of purified eicosapentaenoic acid and docosahexaenoic acid on platelet, fibrinolytic and vascular function in hypertensive type 2 diabetic patients." Atherosclerosis 166: 85-93 (2003).

Wu, W.H., et al., "Effects of docosahexaenoic acid supplementation on blood lipids, estrogen metabolism, and in vivo oxidative stress in postmenopausal vegetarian women." Eur J Clin Nutr. 2006;60:386-392.

Xiao, Y.F., et al., "Inhibitory effect of n-3 fish oil fatty acids on cardiac $Na^+/Ca^{2+}$ exchange currents in HEK293t cells." Biochemical and Biophysical Research Communications 321: 116-123 (2004).

Xiao, Y-F., et al., "Blocking effects of polyunsaturated fatty acids on $Na^+$ channels of neonatal rat ventricular myocytes." Proc. Natl. Acad. Sci. 92: 11000-11004 (1995).

Xiao, Y-F., et al., "Fatty acids suppress voltage-gated $Na^+$ currents in HEK293t cells transfected with the a-subunit of the human cardiac $Na^+$channel." Proc. Natl. Acad. Sci. 95: 2680-2685 (1998).

Xydakis, A M et al., "Combination therapy for combined dyslipidemia," American Journal of Cardiology, Nov. 20, 2002 US, vol. 90, No. 10 Suppl. 2, p. 21 K-29K.

Yamamoto, H. et al., Improvement of coronary vasomotion with Eicosapentaenoic acid does not inhibit acetylcholine-induced coronary vasospasm in patients with variant angina: Jpn Cir J. 59(9):608-16 (Sep. 1995).

Yamamoto, K., et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (2008).

Yamashita, Atsushi, et al., J. Biochem., vol. 122, No. 1, "Acyltransferases and Transacylases Involved in Fatty Acid Remoding of Phospholipids and Metabolism of Bioactive Lipids in Mammalian Cells", pp. 1-16, 1997.

Yamashita, N., et al., "Inhibition of natural killer cell activity of human lymphocytes by eicosapentaenoic acid." Biochem. Biophys. Res. Comm. 138(3): 1058-1067 (1986).

Yamazaki, et. al., "Dissolution tests by RDC method for soft gelatin capsules containing ethyl icosapentate,", Pharm. Tech. Japan, vol. 15, No. 4, pp. 595-603 (1999). Abstract.

Yamazaki, K., et al., "Changes in fatty acid composition in rat blood and organs after infusion of eicosapentaenoic acid ethyl ester", Biochim. Biophys. Acta (1992), 1128(1), 35-43.

Yang, S.P., et al., "Eicosapentaenoic acid attenuates vascular endothelial growth factor-induced proliferation via inhibiting Flk-1 receptor expression in bovine carotid artery endothelial cells." J. Cell. Physio. 176:342-349 (1998).

Yano T, Mizuguchi K, Takasugi K, Tanaka Y, Sato M. "Effects of ethyl all-cis-5,8,11,14,17-icosapentaenoate on low density lipoprotein in rabbits," Yakugaku Zasshi 1995; 115:843-51.

Yano, T., et al., "Effects of ethyl-all-cis-5,8,11,14,17-icosapentaenoate (EPA-E), pravastatin and their combination on serum lipids and intimal thickening of cuff-sheathed carotid artery in rabbits." Life Sciences, 61(20):2007-2015 (1997).

Yerram, N.R., et al., "Eicosapentaenoic acid metabolism in brain microvessel endothelium: effect on prostaglandin formation." J. Lipid Res.30:1747-1757 (1989).

Yokoyama et al., "Effects of eicosapentaenoic acid on major coronary events in hypercholesterolaemic patients (JELIS): a randomized open-label, blinded endpoint analysis", Lancet, vol. 369, pp. 1090-1098 (2007).

Yoshimura, T., et al., Effects of highly purified eicosapentaenoic acid on plasma beta thromboglobulin level and vascular reactivity to angiotensin II, Artery (1987) 14(5) pp. 295-303.

Zaima, N., et al., "*Trans* geometric isomers of EPA decrease LXRa-induced cellular triacylglycerol via suppression of SREBP-1c and PGC-1β." J. Lipid Res. 47: 2712-2717 (2006).

Zanarini, et al., "Omega-3 Fatty Acid Treatment of Women with Borderline Personality Disorder: A Double-Blind, Placebo-Controlled Pilot Study," Am J Psychiatry 2003; 160:167-169.

Zhang, M., et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (2006).

Zhang, Y.W., et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential FattyAcids 67(4):253-261 (2002).

Zhang, Y.W., et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (1999).

Zhao, G. et al., "Dietary α-linolenic acid inhibits proinflammatory cytokine production by peripheral blood mononuclear cells in hypercholesterolemic subjects." Am J Clin Nutr 85:385-91 (2007).

Zhao, G., et al., "Dietary β-linolenic acid reduces inflammatory and lipid cardiovascular risk factors in hypercholesterolemic men and women." J. Nutr. 134: 2991-2997 (2004).

Ziegler, D., et al., "Treatment of symptomatic diabetic polyneuropathy with the antioxidant α-lipoic acid: A 7-month multicenter randomized controlled trial (ALADIN III Study)." Diabetes Care 22:1296-1301 (1999).

Zuijdgeest-van Leeuwen, et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, Feb. 2000, pp. 89-100.

Zuijdgeest-van Leeuwen, S.D., et al., "Incorporation and washout of orally administered n-3 fatty acid ethyl esters in different plasma lipid fractions." British Journal of Nutrition 82:481-488 (1999).

Zuijdgeest-van Leeuwen, SD, et al., "Eicosapentaenoic acid inhibits lipolysis in weight-losing cancer patients as well as in healthy volunteers," Eur J Gastroenterol & Hepatol 1998; 10(12):A67.

U.S. Appl. No. 12/815,569.
U.S. Appl. No. 12/888,994.
U.S. Appl. No. 12/951,620.
U.S. Appl. No. 13/040,977.
U.S. Appl. No. 13/061,865.
U.S. Appl. No. 13/124,628.
U.S. Appl. No. 13/198,221.
U.S. Appl. No. 13/266,085.
U.S. Appl. No. 13/266,374.
U.S. Appl. No. 13/272,520.
U.S. Appl. No. 13/349,157.
U.S. Appl. No. 13/359,114.
U.S. Appl. No. 13/403,694.
U.S. Appl. No. 13/403,699.
U.S. Appl. No. 13/404,666.
U.S. Appl. No. 13/404,686.
U.S. Appl. No. 13/417,899.
U.S. Appl. No. 13/418,591.
U.S. Appl. No. 13/439,392.
U.S. Appl. No. 13/458,496.
U.S. Appl. No. 13/482,720.
U.S. Appl. No. 13/540,319.
U.S. Appl. No. 13/608,744.
U.S. Appl. No. 13/610,217.
U.S. Appl. No. 13/614,111.
U.S. Appl. No. 13/614,129.
U.S. Appl. No. 13/614,146.

Final Agenda for the Oct. 16, 2013 Meeting of the Endocrinologic and Metabolic Drugs Advisory Committee.

Draft Agenda for the Oct. 16, 2013 Meeting of the Endocrinologic and Metabolic Drugs Advisory Committee.

(56) References Cited

OTHER PUBLICATIONS

Final Meeting Roster for the Oct. 16, 2013 Meeting of the Endocrinologic and Metabolic Drugs Advisory Committee.
Draft Meeting Roster for the Oct. 16, 2013 Meeting of the Endocrinologic and Metabolic Drugs Advisory Committee.
Committee Roster for the Oct. 16, 2013 Meeting of the Endocrinologic and Metabolic Drugs Advisory Committee.
Final Questions for the Oct. 16, 2013 Meeting of the Endocrinologic and Metabolic Drugs Advisory Committee.
Draft Questions for the Oct. 16, 2013 Meeting of the Endocrinologic and Metabolic Drugs Advisory Committee.
Webcast Information for the Oct. 16, 2013 Meeting of the Endocrinologic and Metabolic Drugs Advisory Committee.
Slides for the Oct. 16, 2013 Meeting of the Endocrinologic and Metabolic Drugs Advisory Committee.
Transcript from Oct. 16, 2013 Meeting of the Endocrinologic and Metabolic Drugs Advisory Committee.

METHODS OF TREATING MIXED DYSLIPIDEMIA

CROSS-REFERENCE TO RELATED APPLICATION(S)

This application is a continuation of U.S. patent application Ser. No. 13/417,899 filed on Mar. 12, 2012, which is a continuation of U.S. patent application Ser. No. 13/255,085 filed on Jan. 30, 2012, which is a National Stage Entry of Application No. PCT/US10/32948 filed on Apr. 29, 2010, which claims priority from U.S. Provisional Patent Application No. 61/173,759 filed on Apr. 29, 2009, all of which are incorporated herein in their entirety.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke.

SUMMARY

In one embodiment, the present invention provides a pharmaceutical composition comprising EPA and optionally one or more additional cardiovascular agents. In another embodiment, the EPA comprises eicosapentaenoic acid ethyl ester. In another embodiment, the composition contains substantially no amount of docosahexaenoic acid or derivative thereof (e.g. ethyl-DHA), if any.

In other embodiments, the present invention provides methods of treating and/or preventing a cardiovascular-related disease comprising administering to a subject in need thereof a pharmaceutical composition or composition(s) comprising EPA and optionally one or more additional cardiovascular agents.

In any of the foregoing embodiments, the EPA and additional cardiovascular agent(s) can be co-formulated as a single dosage unit or can be formulated as two to a plurality of dosage units for coordinated, combination or concomitant administration.

These and other embodiments of the present invention will be disclosed in further detail herein below.

DETAILED DESCRIPTION

Figure 1:
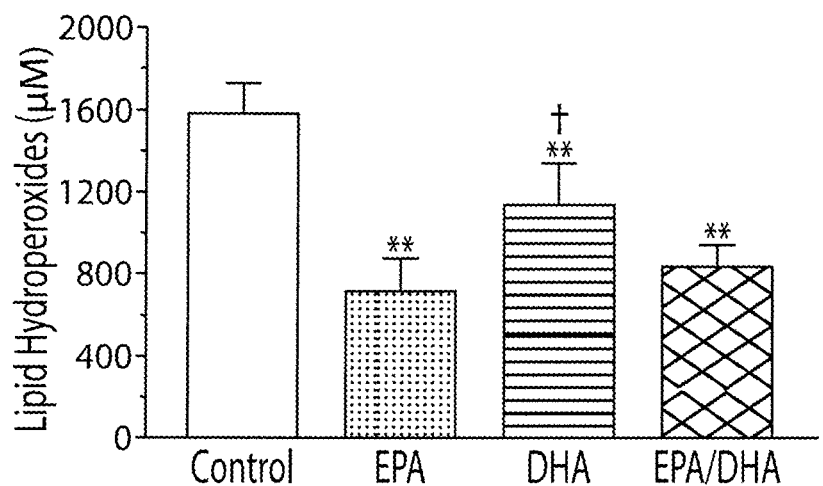
FIG. 1 shows effects of EPA, DHA and Combination Treatment on membrane lipid peroxidation at cholesterol-to-phospholipid ratio of 1.0.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." In this manner, slight variations from a stated value can be used to achieve substantially the same results as the stated value. Also, the disclosure of ranges is intended as a continuous range including every value between the minimum and maximum values recited as well as any ranges that can be formed by such values. Also disclosed herein are any and all ratios (and ranges of any such ratios) that can be formed by dividing a recited numeric value into any other recited numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present invention.

Eicosapentaenoic Acid

In one embodiment, compositions of the invention comprise EPA as an active ingredient. The term "EPA" as used herein refers to eicosapentaenoic acid (e.g. eicosa-5,8,11,14,17-pentaenoic acid) and/or a pharmaceutically acceptable ester, derivative, conjugate or salt thereof, or mixtures of any of the foregoing. The term "pharmaceutically acceptable" in the present context means that the substance in question does not produce unacceptable toxicity to the subject or interaction with other components of the composition.

In one embodiment, the EPA comprises all-cis eicosa-5,8,11,14,17-pentaenoic acid. In another embodiment, the EPA is in the form of an eicosapentaenoic acid ester (also referred to herein as E-EPA or ethyl-EPA). In another embodiment, the EPA comprises a $C_1$-$C_5$ alkyl ester of EPA. In another embodiment, the EPA comprises, eicosapentaenoic acid methyl ester, eicosapentaenoic acid propyl ester, or eicosapentaenoic acid butyl ester. In still another embodiment, the EPA comprises all-cis eicosa-5,8,11,14,17-pentaenoic acid ethyl ester.

In another embodiment, the EPA comprises lithium EPA, mono, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree.

In one embodiment, EPA present in a composition of the invention comprises ultra-pure EPA. The term "ultra-pure" as used herein with respect to EPA refers to a composition comprising at least 96% by weight EPA (as the term "EPA" is defined and exemplified herein). Ultra-pure EPA can comprise even higher purity EPA, for example at least 97% by weight EPA or at least 98% by weight EPA, wherein the EPA is any form of EPA as set forth herein. Ultra-pure EPA can further be defined (e.g. impurity profile) by any of the description of EPA provided herein.

In another embodiment, the EPA comprises an EPA-Fatty Acid conjugate wherein EPA is conjugated to another molecule of EPA or to another fatty acid. In one embodiment, the EPA-Fatty Acid conjugate comprises a diester formed between EPA and EPA or between EPA a second fatty acid as shown in structures (I) and (II). In one embodiment, $R^1$ is a fatty acid acyl group derived from EPA and $R^2$ is selected from H, a fatty acid acyl of 12 to 30 carbon atoms with two or more cis or trans double bonds and fatty alcohol groups of 12 to 30 carbon atoms, the same or different than $R^1$. $R^1$ and $R^2$ may both be derived from EPA (EPA-EPA) or one may be derived from EPA and the second from a different fatty acid (EPA-Fatty acid), for example gamma-linolenic acid, dihomo-gammalinolenic acid, arachidonic acid, adrenic acid, stearidonic acid, docosapentaenoic acid n-3, etc.). $R^3$ is generally either hydrogen, fully hydrocarbon, or containing heteroatoms, and in one embodiment is a $C_1$-$C_4$ alkyl group.

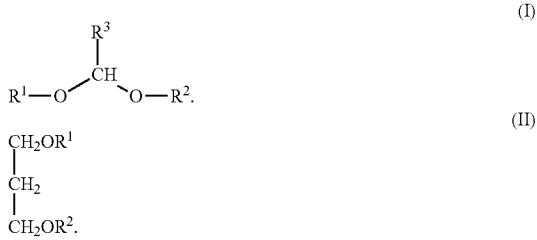

Synthesis of a diester conjugate can be accomplished according to methods well known in the art, including for example, using metals, metal-chlorides, or organic acids as catalysts; using fatty acid chlorides such as EPA-chloride, γ-linolenic acid chloride (GLAchloride), dihomo-γ-linolenic acid chloride (DGLA-chloride), linoleic acid chloride (LA-chloride), arachidonic acid chloride (AA-chloride), conjugated linoleic acid chloride (cLA-chloride), ALA-chloride, STA-chloride, ETA-chloride, DPA-chloride, etc.; and the use of immobilized enzymes as catalysts.

In another embodiment, a composition of the present invention includes a mixture of EPA-Fatty Acid diesters. In a related embodiment, compositions of the present invention include less than 20% EPA-DHA conjugate, less than 15% EPA-DHA conjugate, less than 10% EPA-DHA conjugate, less than 9% EPA-DHA conjugate, less than 8% EPADHA conjugate, less than 7% EPA-DHA conjugate, less than 6% EPA-DHA conjugate, less than 5% EPA-DHA conjugate, less than 4% EPA-DHA conjugate, less than 3% EPA-DHA conjugate, less than 2% EPA-DHA conjugate, less than 1% EPA-DHA conjugate, less than 0.5% EPA-DHA conjugate, or less than 0.1% EPA-DHA conjugate, by weight.

In another embodiment, a composition of the present invention includes at least 96% EPA-Fatty acid conjugate (e.g. EPA-EPA), at least 97% EPA-Fatty acid conjugate, at least 98% EPA-Fatty acid conjugate, or at least 99% EPA-Fatty acid conjugate. In another embodiment, a composition of the present invention contains no more than 10%, no more than 9%, no more than 8%, no more than 7%, no more than 6%, no more than 5%, no more than 4%, no more than 3%, no more than 2%, no more than 1%, or no more than 0.6%, no more than 0.5%, no more than 0.4%, no more than 0.3%, no more than 0.2, or no more than 0.1% of any EPA-Fatty Acid conjugate other than EPA-EPA diester.

In another embodiment, EPA is present in a composition of the invention in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In one embodiment, a composition of the invention contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight of total fatty acids, docosahexaenoic acid or derivative thereof such as ethyl-DHA (E-DHA), if any. In another embodiment, a composition of the invention contains substantially no docosahexaenoic acid or derivative thereof such as E-DHA. In still another embodiment, a composition of the invention contains no docosahexaenoic acid or E-DHA.

In another embodiment, EPA represents at least about 60%, at least about 70%, at least about 80%, at least about 90%, at least about 95%, at least about 97%, at least about 98%, at least about 99%, or 100%, by weight, of all fatty acids present in a composition of the invention.

In another embodiment, a composition of the invention contains less than 30%, less than 20%, less than 10%, less than 9%, less than 8%, less than 7%, less than 6%, less than 5%, less than 4%, less than 3%, less than 2%, less than 1%, less than 0.5% or less than 0.25%, by weight of the total composition or by weight of the total fatty acid content, of any fatty acid other than EPA, or derivative thereof. Illustrative examples of a "fatty acid other than EPA" include linolenic acid (LA) or derivative thereof such as ethyl-linolenic acid, arachidonic acid (AA) or derivative thereof such as ethyl-AA, docosahexaenoic acid (DHA) or derivative thereof such as ethyl-DHA, alpha-linolenic acid (ALA) or derivative thereof such as ethyl-ALA, stearadonic acid (STA) or derivative thereof such as ethyl-SA, eicosatrienoic acid (ETA) or derivative thereof such as ethyl-ETA and/or docosapentaenoic acid (DPA) or derivative thereof such as ethyl-DPA.

In another embodiment, a composition of the invention has one or more of the following features: (a) eicosapentaenoic acid ethyl ester represents at least 96%, at least 97%, or at least 98%, by weight, of total fatty acids present in the composition; (b) the composition contains not more than 4%, not more than 3%, or not more than 2%, by weight, of total fatty acids other than eicosapentaenoic acid ethyl ester; (c) the composition contains not more than 0.6%, 0.5%, or 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (f) the composition contains not more than 20 ppm, 15 ppm or 10 ppm heavy metals, (g) the composition contains not more than 5 ppm, 4 ppm, 3 ppm, or 2 ppm arsenic, and/or (h) the composition has a peroxide value not more than 5, 4, 3, or 2 Meq/kg.

In another embodiment, a composition useful in accordance with the invention comprises, consists essentially of or consists of at least 95% ethyl eicosapentaenoate (EPA-E), about 0.2% to about 0.5% ethyl octadecatetraenoate (ODTA-E), about 0.05% to about 0.25% ethyl nonaecapentaenoate (NDPA-E), about 0.2% to about 0.45% ethyl arachidonate (AA-E), about 0.3% to about 0.5% ethyl eicosatetraenoate (ETA-E), and about 0.05% to about 0.32% ethyl heneicosapentaenoate (HPA-E), each by weight of total fatty acids present in the composition. In another embodiment, the composition is present in a capsule shell. In still another embodiment, the capsule shell contains no chemically modified gelatin.

In another embodiment, compositions useful in accordance with the invention comprise, consist essentially of, or consist of at least 95%, 96% or 97%, ethyl eicosapentaenoate, about 0.2% to about 0.5% ethyl octadecatetraenoate, about 0.05% to about 0.25% ethyl nonaecapentaenoate, about 0.2% to about 0.45% ethyl arachidonate, about 0.3% to about 0.5% ethyl eicosatetraenoate, and about 0.05% to about 0.32% ethyl heneicosapentaenoate, each by weight of all fatty acids present in the composition. Optionally, the composition contains not more than about 0.06%, about 0.05%, or about 0.04%, by weight of total fatty acids present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, about 500 mg to about 1 g of the composition is provided in a capsule shell. In another embodiment, the capsule shell contains no chemically modified gelatin.

In another embodiment, compositions useful in accordance with the invention comprise, consist essentially of, or consist of at least 96% ethyl eicosapentaenoate, about 0.22% to about 0.4% ethyl octadecatetraenoate, about 0.075% to about 0.20% ethyl nonaecapentaenoate, about 0.25% to about 0.40% ethyl arachidonate, about 0.3% to about 0.4% ethyl eicosatetraenoate and about 0.075% to about 0.25% ethyl heneicosapentaenoate, each by weight of total fatty acids present in the composition. Optionally, the composition contains not more than about 0.06%, about 0.05%, or about 0.04%, by weight of total fatty acids present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In one embodiment, the dosage form is a gel- or liquid-containing capsule and is packaged in blister packages of about 1 to about 20 capsules per sheet.

In another embodiment, compositions useful in accordance with the invention comprise, consist essentially of or consist of at least 96%, 97% or 98%, by weight, ethyl eicosapentaenoate, about 0.25% to about 0.38% by weight ethyl octadecatetraenoate, about 0.10% to about 0.15% by weight ethyl nonaecapentaenoate, about 0.25% to about 0.35% by weight ethyl arachidonate, about 0.31% to about 0.38% by weight ethyl eicosatetraenoate, and about 0.08% to about 0.20% ethyl heneicosapentaenoate, each by weight of all fatty acids present in the composition. Optionally, the composition contains not more than about 0.06%, about 0.05%, or about 0.04%, by weight of all fatty acids present, DHA or derivative thereof such as ethyl-DHA. In one embodiment the composition contains substantially no or no amount of DHA or derivative thereof such as ethyl-DHA. The composition further optionally comprises one or more antioxidants (e.g. tocopherol) in an amount of not more than about 0.5% or not more than 0.05%. In another embodiment, the composition comprises about 0.05% to about 0.4%, for example about 0.2% by weight tocopherol. In another embodiment, the invention provides a dosage form comprising about 500 mg to about 1 g of the foregoing composition in a capsule shell. In another embodiment, the capsule shell contains no chemically modified gelatin.

Cardiovascular Agents

In one embodiment, a composition (or co-administration regimen) of the invention comprises one or more additional cardiovascular agents. The one or more additional cardiovascular agents can be co-formulated with EPA or can be co-administered with EPA. The interchangeable terms "cardiovascular agent" or "cardiovascular drug" herein refer to a drug or agent that is capable of treating, preventing, or reducing the risk of developing a cardiovascular disease or disorder, or a risk factor or symptom thereof, in a subject. Cardiovascular agents herein can include, without limitation, cholesterol and triglyceride modulating agents, agents that treat coronary artery disease, agents that treat hypertension or pulmonary arterial hypertension, agents that treat arterial fibrillation or arrhythmia, agents that treat stroke, agents that treat myocardial ischemia and/or agents that treat thrombosis.

Non-limiting examples of classes from which cardiovascular agents suitable for use in accordance with the present invention can be selected include: Acyl-coenzyme A: cholesterol acyltransferase (ACAT) inhibitors including selective inhibitors of ACAT-1, ACAT-2 as well as dual inhibitors of ACAT-1 and ACAT-2, alpha-adrenergic blocking drugs (alpha-blockers), alpha/beta blockers, angiotensin-converting enzyme (ACE) inhibitors, aldosterone antagonists, angiotensin II receptor antagonists, anti-arrhythmics, anticoagulants, antiplatelet agents, apolipoprotein A-1 (apoA-1) mimetics, beta-blockers, bile acid sequestrants, calcium-channel blockers, ApoB cholesteryl ester transfer protein (CETP) inhibitors, cholesterol absorption inhibitors, diuretics, dyslipidemia agents, endothelin receptor antagonists, fibrates, 3-hydroxy-3-methyl-glutaryl-coenzyme A (HMG-CoA) reductase inhibitors, LCAT activators, LDL receptor inducers, lipase inhibitors, lipoprotein-associated phospholipase A2 (Lp-PLA2) inhibitors, microsomal triglyceride transfer protein (MTP) inhibitors, platelet aggregation inhibitors, PPAR agonists and activators including PPARγ agonists, PPARα agonists and PPAR dual α/γ agonists, PCSK9 antisense or RNAi, squalene epoxidase inhibitors, squalene synthetase inhibitors, thrombolytics, and thyroid receptor beta activators.

ACAT Inhibitors.

Acyl-CoA cholesteryl acyl transferase ("ACAT") is an acyltransferase enzyme. In bile acid biosynthesis, ACAT catalyzes the intracellular formation of cholesterol esters from cholesterol. ACAT promotes accumulation of cholesterol esters in vascular tissues. Agents that inhibit ACAT, therefore, are useful in preventing or treating atherosclerosis.

Non-limiting examples of suitable ACAT inhibitors include CI-1011 (Avasimibe, Pfizer), CS-505 (Pactimibe sulfate, Sankyo Pharma), or combinations thereof.

One or more ACAT inhibitors, if desired, are typically present in a composition of the invention (or co-administered with EPA according to other embodiments of the invention) in an amount of about 1 mg to about 1000 mg, for example about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 266 mg, about 275 mg, about 300 mg, about 324 mg, about 325 mg, about 330 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg.

ACE Inhibitors.

Angiotensin I converting enzyme ("ACE") converts angiontensin I to angiotensin II and inhibits bradykinin. Because increased angiotensin II and decreased bradykinin levels both promote a variety of cardiovascular diseases and disorders, agents that inhibit ACE are useful in preventing or treating cardiovascular-related diseases such as hypertension, heart failure, diabetic neuropathy, and type 2 diabetes. Non-limiting examples of suitable ACE inhibitors include captopril, enalapril, enaliprilat, trandolapril, moexipril, ramipril, quinapril, perindopril, lisinopril, benazepril, fosinopril, or combinations thereof.

One or more ACE inhibitors, if desired, are typically present in a composition of the invention (or co-administered with EPA according to other embodiments of the invention) in an amount of about 0.5 mg to about 50 mg, for example about 0.5 mg, about 0.75 mg, about 1 mg, about 1.25 mg, about 2 mg, about 2.5 mg, about 3 mg, about 4 mg, about 5 mg, about 6 mg, about 7 mg, about 7.5 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

Aldosterone Antagonists.

Aldosterone is a steroidal hormone that contributes to hypertension by inhibiting kidney function. Agents that compete with aldosterone for mineralo-corticoid receptors are therefore useful in preventing or treating hypertension. Non-limiting examples of suitable aldosterone agents include eplerenone and aldactone, or combinations thereof.

Aldosterone antagonists, if desired, are typically present in a composition of the invention (or co-administered with EPA according to other embodiments of the invention) in an amount of about 5 mg to about 100 mg, for example about 5 mg, about 10 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95, or about 100 mg.

Alpha Blockers.

Alpha blockers, also called adrenergic alpha-antagonists, compete with adrenaline binding at α-adrenoreceptors. Adrenaline binding at such receptors leads to vasoconstriction and therefore hypertension. Agents that compete with adrenaline or block α-adrenoreceptors are therefore useful in preventing or treating hypertension. Non-limiting examples of suitable alpha blockers include doxazosin, methyldopa, clonidine, prazosin, terazosin, or combinations thereof.

Alpha blockers, if desired, are typically present in a composition of the invention (or co-administered with EPA according to other embodiments of the invention) in an amount of about 0.02 mg to about 0.5 mg, for example about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 2.5 mg, about 0.3 mg, about 3.5 mg, about 0.4 mg, about 4.5 mg, or about 0.5 mg; in an amount of about 0.5 mg to about 15 mg, for example about 0.5 mg, about 0.75 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, or about 15 mg; or in an amount of about 100 mg to about 500 mg, for example about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg.

Alpha/Beta Blockers.

One or more alpha/beta blockers, if desired, are typically present in a composition of the invention (or co-administered with EPA according to other embodiments of the invention) in an amount of about 1 mg to about 25 mg, for example about 1 mg, about 2 mg, about 3 mg, about 3.125 mg, about 4 mg, about 5 mg, about 6 mg, about 6.25 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24, or about 25 mg. A non-limiting example of an alpha/beta blocker is carvedilol.

Angiotensin II Receptor Antagonists.

Angiotensin II receptor antagonists, alternately called angiotensin receptor blockers, ARBs, $AT_1$-receptor antagonists, or sartans, are useful in treating hypertension, congestive heart failure, and various other diseases and disorders. Non-limiting examples of angiotensin II receptor antagonists include candesartan, irbesartan, olmesartan, losartan, valsartan, telmisartan, eprosartan, or combinations thereof.

One or more angiotensin II receptor antagonists, if desired, are typically present in a composition of the invention (or co-administered with EPA according to other embodiments of the invention) in an amount of about 1 mg to about 100 mg, for example about 1 mg, about 2 mg, about 3 mg, about 4 mg, about 5 mg, about 6 mg, about 7 mg, about 8 mg, about 9 mg, about 10 mg, about 12 mg, about 15 mg, about 16 mg, about 20 mg, about 24 mg, about 25 mg, about 28 mg, about 30 mg, about 32 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg; in an amount of about 40 mg to about 320 mg, for example, about 40 mg, about 60 mg, about 80 mg, about 100 mg, about 120 mg, about 140 mg, about 160 mg, about 180 mg, about 200 mg, about 220 mg, about 240 mg, about 260 mg, about 280 mg, about 300 mg, about 320 mg; in an amount of about 200 mg to about 800 mg, for example about 200 mg, about 250 mg, about 300 mg, about 350 mg, about 400 mg, about 450 mg, about 500 mg, about 550 mg, about 600 mg, about 650 mg, about 700 mg, about 750 mg, or about 800 mg.

Anti-Arrhythmic Agents.

Anti-arrhythmic drugs act to correct an irregular heartbeat and/or slow a heart that is beating too rapidly. Non-limiting examples of suitable anti-arrhythmic agents include adenosine, amiodarone, digoxin, disopyramide, flecamide, lidocaine, mexiletine, procainamide, quinidine gluconate, propafenone hydrochloride, tocamide, or combinations thereof.

One or more anti-arrhythmics, if desired, are typically present in a composition of the invention (or co-administered with EPA according to other embodiments of the invention) in an amount of about 0.1 mg to about 1500 mg, about 1 mg to about 1200 mg, or about 5 mg to about 1000 mg, for example about 0.1 mg, about 0.5 mg, about 0.75 mg, about 1 mg, about 5 mg, about 6 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 266 mg, about 275 mg, about 300 mg, about 324 mg, about 325 mg, about 330 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, or about 1500 mg.

In an another embodiment, one or more anti-arrhythmics can be present in an amount of about 1 mg per mL to about 500 mg per mL, for example about 1 mg per mL, about 2 mg per mL, about 3 mg per mL, about 4 mg per mL, about 5 mg per mL, about 6 mg per mL, about 10 mg per mL, about 25 mg per mL, about 50 mg per mL, about 75 mg per mL, about 80 mg per mL, about 100 mg per mL, about 125 mg per mL, about 150 mg per mL, about 175 mg per mL, about 200 mg per mL, about 225 mg per mL, about 250 mg per mL, about 275 mg per mL, about 300 mg per mL, about 325 mg per mL, about 350 mg per mL, about 375 mg per mL, about 400 mg per mL, about 425 mg per mL, about 450 mg per mL, about 475 mg per mL, or about 500 mg per mL.

In another embodiment, an anti-arrhythmics is present in an amount of about 0.01% to about 5%, for example about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% by weight of the total composition.

Antiplatelet Agents.

Antiplatelet agents inhibit platelet aggregation and therefore combat thrombus development. Non-limiting examples of antiplatelet agents include adeparin, aspirin, clopidogrel, danaparoid, deltaparin, denaparoid, ticlopidine, cilostazol, abciximab, eptifibatide, tirofiban, defibrotide, enoxaparin, dipyridamole, tinzaparin, or combinations thereof.

One or more antiplatelet agents, if desired, are typically present in a composition of the invention (or co-administered with EPA according to other embodiments of the invention) in an amount of about 10 mg to about 100 mg, for example about 10 mg, about 12.5 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg; in an amount of about 50 mg to about 300 mg, for example about 50 mg, about 75 mg, about 100 mg, about 125 mg, about 150 mg, about 175 mg, about 200 mg, about 225 mg, about 250 mg, about 275 mg, or about 300 mg.

In another embodiment, one or more antiplatelet agents are present in an amount of about 25 µg per mL to about 50 µg per mL, for example about 25 µg per mL, about 30 µg per mL, about 35 µg per mL, about 40 µg per mL, about 45 µg per mL, or about 50 µg per mL; or in an amount of about 1 mg per mL to about 2 mg per mL, for example about 1 mg per mL, about 1.25 mg per mL, about 1.50 mg per mL, about 1.75, or about 2 mg per mL.

apoA-1 Mimetics.

Apolipoprotein A-1 ("apoA-1") is the primary protein component of serum HDL cholesterol. Non-limiting examples of apoA-1 mimetics include ETC-216, ETC-588-liposome, ETC-642, trimeric apoA-1, CSL-111, APP018, reverse D-4F, or combinations thereof.

One or more apoA-1 mimetics, if desired, are typically present in a composition of the invention (or co-administered with EPA according to other embodiments of the invention) in an amount of about 0.1 mg to about 1500 mg, about 1 mg to about 1200 mg, or about 5 mg to about 1000 mg, for example about 0.1 mg, about 0.5 mg, about 0.75 mg, about 1 mg, about 5 mg, about 6 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 266 mg, about 275 mg, about 300 mg, about 324 mg, about 325 mg, about 330 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, or about 1500 mg.

Beta Blockers.

Beta blockers block responses to the beta nerve receptor which tends to slow heart rate and lower blood pressure. Non-limiting examples of suitable beta blockers include acebutolol, atenolol, metoprolol, nadolol, nebivolol, pindolol, propranolol, or combinations thereof.

One or more beta blockers, if desired, are typically present in a composition of the invention (or co-administered with EPA according to other embodiments of the invention) in an amount of about 1 mg to about 1000 mg, about 1 mg to about 750 mg, or about 1 mg to about 500 mg, for example about 1 mg, about 2 mg, about 2.5 mg, about 3 mg, about 4 mg, about 5 mg, about 10 mg, about 20 mg, about 25 mg, about 30 mg, about 40 mg, about 50 mg, about 60 mg, about 70 mg, about 80 mg, about 90 mg, about 100 mg, about 120 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg.

Bile Acid Sequestrants.

Bile acid sequestrants interrupt the enterohepatic circulation of bile acids by binding bile acid components in the gastrointestinal tract, rendering them unabsorbable thereafter. Bile acid sequestrants are thus useful in preventing or treating hyperlipidemia, among other diseases and disorders. Non-limiting examples of bile acid sequestrants include colesevelam Hcl, colestipol, locholest and cholestyramine or combinations thereof.

One or more bile acid sequestrants, if desired, are typically present in a composition of the invention (or co-administered with EPA according to other embodiments of the invention) in an amount of about 4 mg to about 32 mg, for example about 4 mg, about 8 mg, about 12 mg, about 16 mg, about 24 mg, about 32 mg; or in an amount of about 300 mg to about 4000 mg, for example about 300 mg, about 325 mg, about 350 mg, about 400 mg, about 450 mg, about 500 mg, about 550 mg, about 600 mg, about 625 mg, about 650 mg, about 700 mg, about 750 mg, about 800 mg, about 900 mg, about 1000 mg, about 1250 mg, about 1500 mg, about 1750 mg, about 2000 mg, about 2250 mg, about 2500 mg, about 2750 mg, about 3000 mg, about 3250 mg, about 3500 mg, about 3750, or about 4000 mg.

Calcium Channel Blockers.

Calcium channel blockers are useful in preventing or treating hypertension by their vasodilating action. Non-limiting examples of calcium channel blockers include nicardipine, diltiazem, clevidipine butyrate, isradipine, nimodipine, nisoldipine, verapamil, and amlodipine besylate, or combinations thereof. Non-limiting examples of combination calcium channel blockers include amlodipine, olmesartan, valsartan, or combinations thereof One or more calcium channel blockers, if desired, are typically present in a composition of the invention (or co-administered with EPA according to other embodiments of the invention) in an amount of about 1 mg to about 10 mg, for example about 1 mg, about 2 mg, about 2.5 mg, about 3 mg, about 4 mg, about 5 mg, about 6 mg, about 7 mg, about 8 mg, about 9 mg, or about 10 mg; in an amount of about 5 mg to about 34 mg, for example about 5 mg, about 6 mg, about 7 mg, about 8 mg, about 8.5 mg, about 9 mg, about 10 mg, about 15 mg, about 17.5 mg, about 20 mg, about 22.5 mg, about 25 mg, about 25.5 mg, about 27.5 mg, about 30 mg, about 32.5, or about 34 mg; in an amount of about 10 mg to about 60 mg, for example about 10 mg, about 15 mg, about 20 mg, about 25 mg, about 30 mg, about 35 mg, about 40 mg, about 45 mg, about 50 mg, about 55 mg, or about 60 mg; in an amount of about 20 mg to about 120 mg, for example about 20 mg, about 30 mg, about 40 mg, about 50 mg, about 60 mg, about 70 mg, about 80 mg, about 90 mg, about 100 mg, about 110, or about 120 mg; in an amount of about 60 mg to about 420 mg, for example about 60 mg, about 70 mg, about 80 mg, about 90 mg, about 100 mg, about 110 mg, about 120 mg, about 140 mg, about 160 mg, about 180 mg, about 200 mg, about 220 mg, about 240 mg, about 260 mg, about 280 mg, about 300 mg, about 320 mg, about 340 mg, about 360 mg, about 380 mg, about 400, or about 420 mg.

In another embodiment, one or more calcium channel blockers is present in an amount of about 0.05 mg per mL to about 2.5 mg per mL, for example about 0.05 mg per mL, about 0.1 mg per mL, about 0.2 mg per mL, about 0.3 mg per mL, about 0.4 mg per mL, about 0.5 mg per mL, about 0.6 mg per mL, about 0.7 mg per mL, about 0.8 mg per mL, about 0.9 mg per mL, about 1.0 mg per mL, about 1.25 mg per mL, about 1.5 mg per mL, about 1.75 mg per mL, about 2.0 mg per mL, about 2.25 mg per mL, or about 2.5 mg per mL.

CETP Inhibitors.

Cholesteryl ester transfer protein ("CETP") plays an important role in transferring cholesteryl esters and triglycerides. Inhibition of CETP, also called plasma lipid transfer protein, is therefore useful in preventing or treating atherosclerosis and other cardiovascular diseases and disorders. Non-limiting examples of CETP inhibitors include torcetrapib, anacetrapib, JTT-705, BAY-60-5521, PF-3185043, and CP-800569, or combinations thereof.

One or more CETP inhibitors, if desired, are present in a composition of the invention (or co-administered with EPA according to other embodiments of the invention) in an amount sufficient to provide the subject with a dose of about 25 mg per kg body weight ("mg per kg") to about 100 mg per kg, for example about 25 mg per kg, about 30 mg per kg, about 35 mg per kg, about 40 mg per kg, about 45 mg per kg, about 50 mg per kg, about 55 mg per kg, about 60 mg per kg, about 65 mg per kg, about 70 mg per kg, about 75 mg per kg, about 80 mg per kg, about 85 mg per kg, about 90 mg per kg, about 95 mg per kg, or about 100 mg per kg.

In another embodiment, one or more CETP inhibitors, if desired, are present in a composition of the invention (or co-administered with EPA according to other embodiments of the invention) in an amount of about 100 mg to about 10 g, about 500 mg to about 9 g, or about 750 mg to about 5 g.

Cholesterol Absorption Inhibitors.

Cholesterol absorption inhibitors reduce the cholesterol content of chylomicrons and chylomicron remnants by preventing the uptake of micellar cholesterol from the small intestine. As a result, less cholesterol is delivered to the liver and thereby reduces LDL. Non-limiting examples of cholesterol absorption inhibitors include ezetimibe and simvastatin, or combinations thereof.

One or more cholesterol absorption inhibitors, if desired, are typically present in a composition of the invention (or co-administered with EPA according to other embodiments of the invention) in an amount of about 1 mg to about 10 mg, for example about 1 mg, about 2 mg, about 3 mg, about 4 mg, about 5 mg, about 6 mg, about 7 mg, about 8 mg, about 9 mg, or about 10 mg; or in an amount of about 10 to about 80 mg, for example about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, or about 80 mg.

Diuretics.

Diuretics increase urination rates forcing diuresis. Some diuretics also provide antihypertensive effects. Non-limiting examples of diuretics include hydrochlorothiazide, torsemide, ethacrynic acid, furosemide, triamterene, indapamide, chlorothiazide sodium, aliskiren, or combinations thereof.

One or more diuretics, if desired, are typically present in a composition of the invention (or co-administered with EPA according to other embodiments of the invention) in an amount of: (a) about 0.25 mg to about 2.5 mg, for example about 0.25 mg, about 0.5 mg, about 0.75 mg, about 1 mg, about 1.25 mg, about 1.5 mg, about 1.75 mg, about 2 mg, about 2.25 mg, or about 2.5 mg; (b) in an amount of about 5 mg to about 25 mg, for example about 5 mg, about 10 mg, about 12.5 mg, about 15 mg, about 17.5 mg, about 20 mg, about 22.5 mg, or about 25 mg; (c) in an amount of about 2 mg to about 100 mg, for example about 2 mg, about 3 mg, about 4 mg, about 5 mg, about 7.5 mg, about 10 mg, about 12.5 mg, about 15 mg, about 17.5 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg; (d) about 10 mg to about 50 mg, for example about 10 mg, about 12.5 mg, about 15 mg, about 17.5 mg, about 20 mg, about 22.5 mg, about 25 mg, about 30 mg, about 35 mg, about 40 mg, about 45 mg, or about 50 mg; in an amount of about 5 mg to about 60 mg, for example about 5 mg, about 10 mg, about 15 mg, about 20 mg, about 25 mg, about 30 mg, about 35 mg, about 40 mg, about 45 mg, about 50 mg, about 55 mg, (e) or about 60 mg; in an amount of about 25 mg to about 100 mg, for example about 25 mg, about 30 mg, about 35 mg, about 40 mg, about 45 mg, about 50 mg, about 60 mg, about 70 mg, about 80 mg, about 90 mg, or about 100 mg; in an amount of about 75 mg to about 300 mg, for example about 75 mg, about 100 mg, about 125 mg, about 150 mg, about 175 mg, about 200 mg, about 225 mg, about 250 mg, about 275 mg, or about 300 mg; (f) about 0.1 g to about 0.5 g, for example about 0.1 g, about 0.2 g, about 0.3 g, about 0.4 g, or about 0.5 g; or (g) in an amount of about 1 mg per mL to about 10 mg per mL, for example about 1 mg per mL, about 2 mg per mL, about 3 mg per mL, about 4 mg per mL, about 5 mg per mL, about 6 mg per mL, about 7 mg per mL, about 8 mg per mL, about 9 mg per mL, or about 10 mg per mL.

Dyslipidemia Agents.

Dyslipidemia is a class of diseases that includes hyperlipidemia. Fredrickson's Type I dyslipidemia (sometimes referred to as Buerger-Gruetz syndrome, primary hyperlipoproteinaemia, or familial hyperchylomicronemia) is characterized by elevated cholesterol levels, subjects with Fredrickson's Type IIa dyslipidemia (also known as familial hypercholesterolemia) exhibit elevated LDL levels. Those with Fredrickson's Type IIb dyslipidemia (familial combined hyperlipoproteinemia (FCH) or secondary combined hyperlipoproteinemia) show increased LDL and VLDL levels. Fredrickson's Type III dyslipidemia (sometimes called beta disease or dysbetalipoproteinemia) features elevated intermediate density lipoproteins ("IDL"), while Fredrickson's Type IV dyslipidemics (sometimes called "pure hypertriglyceridemics") have elevated VLDL levels. Subjects with Fredrickson's Type V dyslipidemia have increased VLDL and chylomicron levels.

Non-limiting examples of dyslipidemia agents include Angptl4 antibody, APA-01 (Phosphagenics), CRD-5 (ImaSight), NCX6560 (NicOx), PCSK9 RNAi (Alnylam), recombinant apoA-1 (SemBioSys Genetics), anti-oxLDL (Genentech), APL180 (Novartis), APP018 (D4F) (Novartis), CER-002 (Cerenis Therapeutics), CP-800,569 (Pfizer), GSK256073 (GlaxoSmithKline), MB07811 (Metabasis), PF-3,185,043 (Pfizer), R7232 (Roche), rilapladib (GlaxoSmithKline), RVX-208 (Resverlogix), Sobetirome (QRX-431 (QuatRx)), anacetrapib (Merk), CSL111 (CSL Limited), darapladib (GlaxoSmithKline), eprotirome (Karo Bio), GFT505 (Genfit), MAHDLO1 (Marzal Plant Pharma), MBX-8025 (Metabolex), PLX204 (Wyeth/Plexxikon), aleglitezar (Roche), dalcetrapib (Roche), SLx4090 (Surface Logix), verespladib (Anthera Pharmaceuticals), AEGR-733 (Aegerion), ABT-335 (Abbott Laboratories), AVE5530 (Sanofi-Aventis), LCP-AtorFen (LifeCycle Pharma), TRIA-662 (Cortria), fenofibrate, choline fenofibrate, ezetimibe, colsevelam, laropiprant, or combinations of any of the foregoing.

One or more dyslipidemia agents, if desired, are typically present in a composition of the invention (or co-administered with EPA according to other embodiments of the invention) in an amount of about 1 mg to about 1000 mg, for example about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 43 mg, about 45 mg, about 48 mg, about 50 mg, about 54 mg, about 55 mg, about 60 mg, about 65 mg, about 67 mg, about 70 mg, about 75 mg, about 80 mg, about 85 mg, about 87 mg, about 90 mg, about 95 mg, about 100 mg, about 105 mg, about 107 mg, about 110 mg, about 115 mg, about 120 mg, about 125 mg, about 130 mg, about 134 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 250 mg, about 275 mg, about 300 mg, about 325 mg, about 350 mg, about 375 mg, about 400 mg, about 425 mg, about 450 mg, about 500 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg.

Endothelin Receptor Antagonists.

Binding of endothelin-1 at endothelin-A (ETA) or endothelin-B (ETB) receptors causes pulmonary vasoconstriction. Endothelin receptor antagonists compete with endothelin-1 binding, thereby attenuating pulmonary vasoconstriction. Endothelin receptor antagonists, therefore, are useful in treating pulmonary hypertension. Non-limiting examples of endothelin receptor antagonists include ambrisentan, bosentan, volibris, thelin, or combinations thereof.

One or more endothelin receptor antagonists, if desired, are typically present in a composition of the invention (or co-administered with EPA according to other embodiments of the invention) in an amount of about 1 mg to about 10 mg, for example about 1 mg, about 2 mg, about 3 mg, about 4 mg, about 5 mg, about 6 mg, about 7 mg, about 8 mg, about 9 mg, or about 10 mg; in an amount of about 50 mg to about 250 mg, for example about 50 mg, about 75 mg, about 100 mg, about 125 mg, about 150 mg, about 175 mg, about 200 mg, about 225 mg, or about 250 mg.

HMG-CoA Reductase Inhibitors.

HMG-CoA reductase (also known as HMGR) converts HMG-CoA (3-hydroxy-3-methyl-glutaryl-coenzyme A) to mevalonic acid (3,5-dihydroxy-3-methyl-pentanoic acid) along the metabolic pathway that produces cholesterol. HMG-CoA reductase inhibitors, also called statins, inhibit HMG-CoA reductase and thereby reduce cholesterol production. As a result, HMG-CoA reductase inhibitors are useful in treating a variety of cardiovascular diseases and disorders including, for example, hypercholesterolemia, hyperlipidemia, mixed dyslipidemia, hypertriglyceridemia, atherosclerosis, Non-limiting examples of HMG-CoA reductase inhibitors include lovastatin, lovastatin+niacin, mevastatin, pitavastatin, pravastatin, rosuvastatin, fluvastatin, atorvastatin, atorvastatin+amlodipine besylate, simvastatin, simvastatin+niacin, ezetimibe, and pravastatin, among others.

One or more HMG-CoA reductase inhibitors, if desired, are typically present in a composition of the invention (or co-administered with EPA according to other embodiments of the invention) in an amount of about 1 mg to about 1000 mg, for example about 1 mg, about 2 mg, about 3 mg, about 4 mg, about 5 mg, about 6 mg, about 7 mg, about 8 mg, about 9 mg, or about 10 mg; about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg.

LCAT Activators.

Lecithin-cholesterol acyltransferase ("LCAT") converts cholesterol into cholesteryl ester. In subjects with deficient levels of LCAT, unesterified cholesterol accumulates in body tissues. This can lead to elevated serum levels of HDL and eventually atherosclerosis. LCAT activators are therefore useful in reducing serum HDL levels and treating or preventing atherosclerosis. Non-limiting examples of LCAT activators include LCAT enzyme, recombinant LCAT, genetic therapy agents that include a nucleic acid sequence coding for expression of LCAT, estrogens, estrogen analogs, and combinations thereof for example as disclosed in U.S. Pat. No. 6,635,614 incorporated by reference herein in its entirety.

One or more LCAT activators, if desired, are typically present in a composition of the invention (or co-administered with EPA according to other embodiments of the invention) in an amount sufficient to raise the serum LCAT level of the subject to a desired level. Subjects with abnormally low LCAT serum levels may be administered an amount of a composition of the invention comprising EPA and LCAT enzyme, estrogen, estrogen analogs, or combinations thereof sufficient to raise the subject's serum LCAT level to normal levels, typically about 5 µg per mL or greater. In another embodiment, subjects with about normal LCAT serum levels may be treated with a composition of the invention comprising EPA and LCAT enzyme, estrogen, estrogen analogs, or combinations thereof in an amount sufficient to raise the LCAT serum level to about 6 µg per mL or more, about 7 µg per mL or more, about 8 µg per mL or more, about 9 µg per mL or more, or about 10 µg per mL or more.

LDL Receptor Inducers.

LDL receptors are cell surface proteins. Along with adaptin, LDL receptors bind free LDL cholesterol to form clathrin-coated vesicles, reducing serum LDL levels. Thus, agents that induce LDL receptors further reduce serum LDL levels and are useful in preventing or treating atherosclerosis. A non-limiting example of LDL receptor is lactacystin.

One or more LDL receptor inducers, if desired, are typically present in a composition of the invention (or co-administered with EPA according to other embodiments of the invention) in an amount of about 1 mg to about 1000 mg, for example about 1 mg, about 2 mg, about 3 mg, about 4 mg, about 5 mg, about 6 mg, about 7 mg, about 8 mg, about 9 mg, or about 10 mg about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg.

Lp-PLA2 Inhibitors.

Compositions of the invention may comprise one or more lipoprotein associated phospholipase A2 (Lp-PLA2) inhibitors. Lp-PLA2 hydrolyzes oxidized phospholipids in LDL cholesterols. High levels of Lp-PLA2 seem to trigger a cascade of inflammatory events in atherosclerosis and an increased risk of stroke. Lp-PLA2 inhibitors, therefore, are useful in slowing or preventing development of atherosclerosis. Non-limiting examples of Lp-PLA2 inhibitors include rilapladib, darapladib, and combinations thereof.

One or more Lp-PLA2 inhibitors, if desired, are typically present in a composition of the invention (or co-administered with EPA according to other embodiments of the invention) in an amount of about 1 mg to about 1000 mg, for example about 1 mg, about 2 mg, about 3 mg, about 4 mg, about 5 mg, about 6 mg, about 7 mg, about 8 mg, about 9 mg, or about 10 mg; about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, or about 1000 mg.

5-Lipoxygenase Inhibitors.

5-lipoxygenase inhibitors are useful in accordance with various embodiments of the invention. Non-limiting examples of 5-lipixygenase inhibitors include VIA-2291, MK-886, CMI 977, ABT-761, ZD2138, lonapalene, zileuton, 5-LO inhibitor 6, L-739,010, CGS 22745, SC 45662, and combinations thereof.

Additional 5-lipoxygenase inhibitors suitable for use in accordance with embodiments of the instant invention are disclosed in the following U.S. patents and patent applications, each of which is hereby incorporated by reference herein in its entirety: U.S. 20050101659, U.S. Pat. No. 7,026,344, U.S. Pat. No. 7,329,682, U.S. 20040198768, U.S. 20090054519, U.S. Pat. No. 5,112,848, U.S. Pat. No. 5,086,052, U.S. Pat. No. 482,828, U.S. Pat. No. 5,208,364, U.S. Pat. No. 4,970,210, U.S. Pat. No. 4,794,114, U.S. Pat. No. 4,686,231, U.S. Pat. No. 5,134,150, U.S. Pat. No. 5,639,782, U.S. Pat. No. 6,239,170, U.S. 20060106014, U.S. Pat. No. 5,229,386, U.S. Pat. No. 4,673,684, U.S. Pat. No. 6,136,839, U.S. Pat. No. 6,090,547, U.S. Pat. No. 6,355,434, U.S. 20090042849, U.S. Pat. No. 4,731,382, U.S. Pat. No. 4,877,881, U.S. Pat. No. 5,130,485, U.S. Pat. No. 5,665,752, U.S. Pat. No. 5,723,481, U.S. Pat. No. 5,102,897, U.S. Pat. No. 5,234,939, U.S. Pat. No. 5,143,928, U.S. Pat. No. 5,217,971, U.S. Pat. No. 4,889,941, U.S. Pat. No. 5,234,937, U.S. Pat. No. 5,283,361, U.S. Pat. No. 5,232,939, U.S. Pat. No. 5,086,064, U.S. Pat. No. 5,208,251, U.S. Pat. No. 5,290,800, U.S. Pat. No. 5,006,549, U.S. Pat. No. 5,494,927, U.S. 20040198800, U.S. Pat. No. 4,719,218, U.S. Pat. No. 4,847,270, U.S. Pat. No. 6,121,323, U.S. 20080226758, U.S. 20070218146, U.S. Pat. No. 4,728,656, U.S. Pat. No. 4,835,189, U.S. Pat. No. 5,763,673, U.S. Pat. No. 4,835,190, U.S. Pat. No. 5,162,365, U.S. Pat. No. 5,985,937, U.S. Pat. No. 6,455,541, U.S. Pat. No. 5,534,524, U.S. 20070134341, U.S. 20050267145, U.S. Pat. No. 4,694,018, U.S. Pat. No. 5,260,294, U.S. Pat. No. 5,792,776, U.S. Pat. No. 5,530,141, U.S. Pat. No. 5,780,503, U.S. Pat. No. 5,093,356, U.S. Pat. No. 5,348,957, U.S. Pat. No. 5,384,318, U.S. Pat. No. 568,822, U.S. 20010009918, U.S. 20070219206, U.S. 20070225285, U.S. 20050267211, U.S. 20030162193, U.S. 20070173508, U.S. 20070066577, U.S. Pat. No. 5,036,067, U.S.

20030082108, U.S. 20090018170, U.S. 20070105866, U.S. 20070237848, U.S. 20070244185, U.S. 20080227807, U.S. Pat. No. 4,728,735, U.S. Pat. No. 4,803,279, U.S. Pat. No. 4,962,119, U.S. Pat. No. 5,314,898, U.S. 20070123522, U.S. 20070123522, U.S. 20070244128, U.S. 20070093524, U.S. Pat. No. 4,602,023, U.S. Pat. No. 4,943,587, U.S. Pat. No. 6,025,384, U.S. 20090118373, U.S. Pat. No. 5,112,868, U.S. Pat. No. 5,254,553, U.S. Pat. No. 5,312,821, U.S. Pat. No. 5,635,514, U.S. Pat. No. 7,405,302, U.S. Pat. No. 4,624,964, U.S. Pat. No. 4,786,755, U.S. Pat. No. 4,933,351, U.S. Pat. No. 5,059,609, U.S. Pat. No. 5,442,111, U.S. Pat. No. 5,066,668, U.S. Pat. No. 5,292,900, U.S. Pat. No. 5,998,451, U.S. Pat. No. 4,851,586, U.S. Pat. No. 5,314,900, U.S. Pat. No. 5,447,943, U.S. Pat. No. 6,221,880, U.S. Pat. No. 6,262,077, U.S. Pat. No. 6,376,528, U.S. Pat. No. 6,569,895, U.S. Pat. No. 4,663,347, U.S. Pat. No. 4,975,457, U.S. Pat. No. 4,978,679, U.S. Pat. No. 5,703,093, U.S. Pat. No. 5,811,432, U.S. Pat. No. 4,822,803, U.S. Pat. No. 5,356,921, U.S. Pat. No. 5,750,565, U.S. Pat. No. 4,751,310, U.S. Pat. No. 4,816,486, U.S. Pat. No. 5,288,751, U.S. Pat. No. 5,298,512, U.S. Pat. No. 5,909,734, U.S. Pat. No. 4,745,127, U.S. Pat. No. 5,215,986, U.S. Pat. No. 5,270,319, U.S. Pat. No. 5,476,944, U.S. Pat. No. 4,939,169, U.S. Pat. No. 6,166,031, U.S. Pat. No. 6,696,477, U.S. Pat. No. 6,756,399, U.S. Pat. No. 4,931,444, U.S. Pat. No. 5,066,658, U.S. Pat. No. 5,248,685, U.S. Pat. No. 5,240,929, U.S. Pat. No. 4,861,798, U.S. Pat. No. 4,933,329, U.S. Pat. No. 5,008,390, U.S. Pat. No. 5,814,648, U.S. Pat. No. 6,939,674, U.S. Pat. No. 5,696,141, U.S. Pat. No. 5,434,151, U.S. 20030216481, U.S. 20030232763, U.S. 20060177528, U.S. 20030235620, U.S. 20020177723, U.S. Pat. No. 5,036,105, U.S. Pat. No. 5,504,097, U.S. Pat. No. 5,741,809, U.S. Pat. No. 5,459,154, U.S. Pat. No. 5,463,083, U.S. Pat. No. 6,420,392, U.S. Pat. No. 5,358,938, U.S. Pat. No. 5,326,907, U.S. Pat. No. 6,294,574, U.S. Pat. No. 5,648,486, U.S. Pat. No. 5,856,323, U.S. Pat. No. 7,387,797, U.S. Pat. No. 4,801,611, U.S. Pat. No. 5,530,114, U.S. Pat. No. 7,514,469, U.S. 20010025040, U.S. 20020143033, U.S. Pat. No. 5,665,749, U.S. 20010009917, U.S. 20070049621, U.S. 20080280826, U.S. Pat. No. 5,393,923, U.S. Pat. No. 5,114,958, U.S. Pat. No. 5,376,670, U.S. Pat. No. 6,217,875, U.S. Pat. No. 5,155,122, U.S. Pat. No. 5,288,896, U.S. Pat. No. 6,436,924, U.S. Pat. No. 5,256,680, U.S. Pat. No. 7,132,441, U.S. Pat. No. 5,145,860, U.S. Pat. No. 5,354,768, U.S. Pat. No. 5,698,576, U.S. Pat. No. 7,371,874, U.S. Pat. No. 5,068,251, U.S. Pat. No. 5,130,483, U.S. Pat. No. 6,177,415, U.S. Pat. No. 5,541,218, U.S. 20070264361, U.S. Pat. No. 5,284,949, U.S. Pat. No. 4,672,075, U.S. Pat. No. 5,212,189, U.S. Pat. No. 5,302,597, U.S. 20080107757, U.S. Pat. No. 6,620,813, U.S. Pat. No. 5,250,565, U.S. Pat. No. 624,012, U.S. Pat. No. 4,732,901, U.S. Pat. No. 5,196,431, U.S. Pat. No. 5,340,815, U.S. Pat. No. 5,504,108, U.S. Pat. No. 5,220,025, U.S. Pat. No. 5,252,562, U.S. Pat. No. 5,420,131, U.S. Pat. No. 5,037,837, U.S. Pat. No. 5,081,126, U.S. Pat. No. 5,105,020, U.S. Pat. No. 5,187,175, U.S. Pat. No. 5,342,838, U.S. Pat. No. 4,755,525, U.S. Pat. No. 5,248,682, U.S. Pat. No. 4,963,576, U.S. Pat. No. 5,514,703, U.S. Pat. No. 6,194,585, U.S. Pat. No. 6,194,585, U.S. Pat. No. 6,291,534, U.S. Pat. No. 4,695,586, U.S. Pat. No. 4,971,979, U.S. Pat. No. 6,653,311, U.S. Pat. No. 4,755,524, U.S. Pat. No. 5,147,893, U.S. Pat. No. 4,711,903, U.S. 20040077691, U.S. Pat. No. 4,695,585, U.S. 2005009084, U.S. Pat. No. 5,516,789, U.S. Pat. No. 5,512,594, U.S. 20070202206, U.S. Pat. No. 6,261,607, U.S. Pat. No. 5,350,754, U.S. Pat. No. 6,344,563, U.S. 20040235807, U.S. Pat. No. 5,064,851, U.S. Pat. No. 5,254,581, U.S. Pat. No. 5,288,742, U.S. Pat. No. 5,403,859, U.S. Pat. No. 5,407,945, U.S. 20030008914, U.S. Pat. No. 5,254,731, U.S. Pat. No. 5,318,970, U.S. Pat. No. 5,519,022, U.S. Pat. No. 6,174,883, U.S. Pat. No. 6,262,073, U.S. 20040170974, U.S. 20070231345, U.S. Pat. No. 4,985,435, U.S. Pat. No. 5,126,365, U.S. Pat. No. 5,234,950, U.S. Pat. No. 5,321,025, U.S. Pat. No. 5,484,805, U.S. Pat. No. 5,221,677, U.S. Pat. No. 5,280,047, U.S. Pat. No. 5,300,655, and U.S. Pat. No. 5,359,063.

One or more 5-lipoxygenase inhibitors, if desired, are typically present in a composition of the invention (or co-administered with EPA according to other embodiments of the invention) in an amount of about 0.01 mg to about 2500 mg, about 0.1 mg to about 1500 mg, about 1 mg to about 1200 mg, or about 5 mg to about 1000 mg, for example about 0.1 mg, about 0.5, about 0.75 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

Microsomal Triglyceride Transfer Protein Inhibitors.

Microsomal triglyceride transfer protein ("MTTP" or "MTP") is a heterodimeric protein involved in lipoprotein assembly. MTP inhibitors are thus useful in slowing or preventing the production of lipoproteins and therefore cardiovascular diseases and disorders. Non-limiting examples of MTP inhibitors include SLx-4090, AEGR-733, implitapide, BMS-200150, CP-346086, JTT-130, dirlotapide, and combinations thereof.

Additional MTP inhibitors suitable for use in accordance with embodiments of the instant invention are disclosed in the following U.S. patents and patent applications, each of which is hereby incorporated by reference herein in its entirety: U.S. 20030166590, U.S. Pat. No. 6,492,365, U.S. 20040132779, U.S. 20040132745, U.S. 20050181376, U.S. 20030086912, U.S. Pat. No. 6,767,739, U.S. 20080249130, U.S. 20020028943, U.S. Pat. No. 5,883,099, U.S. Pat. No. 5,739,135, U.S. Pat. No. 5,712,279, U.S. Pat. No. 6,034,098, U.S. Pat. No. 5,827,875, U.S. Pat. No. 6,066,650, U.S. Pat. No. 5,885,983, U.S. 20060166999, U.S. 20070027183, U.S. 20020045271, U.S. Pat. No. 6,288,234, U.S. 20030109700, U.S. 20040014748, U.S. Pat. No. 6,878,707, U.S. Pat. No. 6,218,524, U.S. Pat. No. 5,595,872, U.S. 20080253985, U.S. 20080103122, U.S. 20050234073, U.S. 20050090426, U.S. 20040044008, U.S. 20090042835, U.S. 20040058908, U.S. 20060270655, U.S. Pat. No. 6,369,075, U.S. 20080241869, U.S. 20070093468, U.S. 20090054393, U.S. 20020132806, U.S. 20070088089, U.S. 20040033506, U.S. 20080161279, U.S. 20020161233, U.S. 20020042516, U.S. 20070093527, U.S. Pat. No. 6,713,489, U.S. 20060211020, U.S. Pat. No. 6,617,325, U.S. Pat. No. 6,147,214 and U.S. 20020032238.

In one embodiment, one or more MTP inhibitors, if desired, are typically present in a composition of the invention (or co-administered with EPA according to other embodiments of the invention) in an amount sufficient to provide the subject with a dose of about 1 μg per kg of body weight (μg per kg) to about 100 μg per kg, for example about 25 μg per kg, about 30 μg per kg, about 35 μg per kg, about 40 μg per kg, about 45 μg per kg, about 50 μg per kg, about 55 μg per kg, about 60 μg per kg, about 65 μg per kg, about 70 μg per kg, about 75 μg per kg, about 80 μg per kg, about 85 μg per kg, about 90 μg per kg, about 95 μg per kg, or about 100 μg per kg. In another embodiment, one or more MTP inhibitors, if desired, are present in a composition of the invention (or co-administered with EPA according to other embodiments of the invention) in an amount of about 30 μg to about 20 mg, about 50 μg to about 15 mg, or about 70 μg to about 10 mg.

In another embodiment, one or more MTP inhibitors, if desired, are present in a composition of the invention (or co-administered with EPA according to other embodiments of the invention) in an amount of about 0.01 mg to about 2500 mg, about 0.1 mg to about 1500 mg, about 1 mg to about 1200 mg, or about 5 mg to about 1000 mg, for example about 0.1 mg, about 0.5, about 0.75 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

PPAR Agonists and Activators.

Peroxisome proliferator-activated receptors ("PPARs") are nuclear receptor proteins regulating the expression of genes by acting as transcription factors in combination with the retinoid X receptor ("RXR"). Agents that inhibit or activate PPARs are therefore useful in modifying the expression of certain genes including, for example, genes associated with metabolic disorders such as hypercholesterolemia. Non-limiting examples of PPAR agonists and activators include fenofibrate, bezafibrate, ciprofibrate, clofibrate, gemfibrozil, CER-002, rosiglitazone, GW501516, RWJ 800025, KD-3010, and combinations thereof.

One or more PPAR agonists and/or activators, if desired, are typically present in a composition of the invention (or co-administered with EPA according to other embodiments of the invention) in an amount of about 0.5 mg to about 4 mg, for example about 0.5 mg, about 0.75 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, or about 4 mg; or in an amount of about 20 mg to about 120 mg, for example about 20 mg, about 30 mg, about 40 mg, about 50 mg, about 60 mg, about 70 mg, about 80 mg, about 90 mg, about 100 mg, about 110 mg, or about 120 mg.

sPLA2 Inhibitors.

sPLA2 inhibitors are suitable for use in accordance with various embodiments of the present invention. Non-limiting examples of sPLA2 inhibitors include LY 333013, varespladib, WA8242A, WA8242A2, WA8242B, A-0001, A-0002 and combinations thereof.

Additional sPLA2 inhibitors suitable for use in accordance with embodiments of the instant invention are disclosed in the following U.S. patents and patent applications, each of which is hereby incorporated by reference herein in its entirety: U.S. Pat. No. 6,974,831, U.S. Pat. No. 6,916,840, U.S. Pat. No. 6,992,100, U.S. Pat. No. 6,872,743, U.S.20040063967, U.S.20040063941, U.S.20040092543, U.S.20040077704, U.S. Pat. No. 6,433,001, U.S.20030153770, U.S.20030191175, U.S. Pat. No. 6,706,752, U.S. Pat. No. 6,730,694, U.S.20040059130, U.S. Pat. No. 7,026,348, U.S. Pat. No. 6,608,099, U.S. Pat. No. 6,340,699, U.S. Pat. No. 6,252,084, U.S. Pat. No. 6,635,670, U.S. Pat. No. 6,939,890, U.S. Pat. No. 6,930,123, U.S. Pat. No. 6,713,505, U.S. Pat. No. 6,274,578, U.S. Pat. No. 6,451,839, U.S.20040029948, U.S.20090062369, U.S.20030236232, U.S. Pat. No. 7,160,909, U.S. Pat. No. 6,384,041, U.S. Pat. No. 6,175,021, U.S. Pat. No. 6,214,876, U.S.20090131396, U.S. Pat. No. 6,353,128, U.S. Pat. No. 6,407,104, U.S. Pat. No. 6,274,616, U.S.20030087944, U.S. Pat. No. 5,916,922, U.S.20040198801, U.S.20080249027, U.S. Pat. No. 7,026,318, U.S. Pat. No. 6,933,313, U.S.20040087796, U.S. Pat. No. 6,391,908, U.S.20030181454, U.S. Pat. No. 6,831,095, U.S. Pat. No. 6,177,426, U.S.20060116379, U.S. Pat. No. 6,472,389, U.S. Pat. No. 6,797,708, U.S.20090118503, U.S.20070249008, U.S. Pat. No. 7,087,637, U.S. Pat. No. 5,919,810, U.S. Pat. No. 6,828,344, U.S. Pat. No. 6,916,841, U.S. Pat. No. 5,654,326, U.S. Pat. No. 5,641,800, U.S. Pat. No. 5,733,923, U.S. Pat. No. 6,534,535, U.S.20050026988, U.S. Pat. No. 6,166,062, U.S. Pat. No. 5,684,034, U.S. Pat. No. 7,253,194, U.S.20080045444, U.S.20040033995, U.S.20060235009, U.S.20090088427, U.S. Pat. No. 7,196,103, U.S.20080317809, U.S.20090092595, U.S.20070037253, U.S. Pat. No. 7,098,237, U.S. Pat. No. 6,140,327, U.S. Pat. No. 5,972,972, U.S.20040248898, U.S. Pat. No. 6,967,200, U.S.20030092767, U.S.20040106669, U.S.20040077651, U.S.20050158401, U.S. Pat. No. 6,514,984, U.S.20040102442, U.S. Pat. No. 6,610,728, U.S.20030119860, U.S. Pat. No. 6,436,983, U.S. Pat. No. 6,703,385, U.S. Pat. No. 6,576,654, U.S. Pat. No. 7,101,875, U.S. Pat. No. 6,635,771, U.S. Pat. No. 6,756,376, U.S. Pat. No. 6,984,735, U.S. Pat. No. 6,448,284, U.S. Pat. No. 6,787,545, U.S. Pat. No. 6,265,591, U.S. Pat. No. 6,713,645, U.S. Pat. No. 6,673,781, U.S. Pat. No. 6,214,855, U.S. Pat. No. 6,008,231, U.S. Pat. No. 6,344,467, U.S. Pat. No. 6,177,440, U.S. Pat. No. 6,426,344, U.S. Pat. No. 7,105,514, U.S. Pat. No. 6,214,991, U.S.20020169108, U.S.20060025348, U.S.20030008816, U.S.20090029917, U.S. Pat. No. 6,900, 208, U.S. Pat. No. 6,380,397, U.S. Pat. No. 7,205,329, U.S. Pat. No. 5,919,943, U.S. Pat. No. 7,126,010, U.S. Pat. No. 7,109,231, U.S. Pat. No. 6,555,568, U.S. Pat. No. 6,872,557, U.S. Pat. No. 7,030,112, U.S. Pat. No. 7,041,695, U.S. Pat. No. 7,220,756, U.S. Pat. No. 7,396,838, U.S. Pat. No. 6,407,261, U.S. Pat. No. 6,028,116, U.S. Pat. No. 5,965,619, U.S. Pat. No. 6,063,818, U.S. Pat. No. 5,998,477, U.S. Pat. No. 6,121,321, U.S. Pat. No. 6,958,348, U.S. Pat. No. 7,528,112, U.S. Pat. No. 6,903,104, U.S. Pat. No. 6,745,133, U.S. Pat. No. 6,861,436, U.S. Pat. No. 5,650,374, U.S. Pat. No. 6,569,539, U.S. Pat. No. 6,432,987, U.S. Pat. No. 5,762,413, U.S. Pat. No. 7,176,281, U.S. Pat. No. 7,317,009, U.S. Pat. No. 7,153,854, U.S.20020110523, U.S. Pat. No. 6,776,986, U.S. Pat. No. 5,948,779, U.S. Pat. No. 7,449,615, U.S. Pat. No. 7,531,568, U.S. Pat. No. 7,476,746, U.S. Pat. No. 7,491,831, U.S. Pat. No. 6,231,189, U.S. Pat. No. 6,987,105, U.S. Pat. No. 7,300,932, U.S. Pat. No. 6,962,784, U.S. Pat. No. 6,248,553, U.S. Pat. No. 6,255,063, U.S.20070053912, U.S. Pat. No. 6,974,831, U.S.20040063941, U.S.20040077704, U.S.20040248898, U.S.20040063967, U.S. Pat. No. 6,992,100, U.S.20040092543, U.S. Pat. No. 6,916,840, U.S. Pat. No. 6,433,001, U.S.20070249008, U.S.20090092595, U.S. Pat. No. 6,872,743, U.S.20070037253.

One or more sPLA2 inhibitors, if desired, are typically present in a composition of the invention (or co-administered with EPA according to other embodiments of the invention) in an amount of about 0.01 mg to about 2500 mg, about 0.1 mg to about 1500 mg, about 1 mg to about 1200 mg, or about 5 mg to about 1000 mg, for example about 0.1 mg, about 0.5, about 0.75 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg or about 2500 mg.

Squalene Epoxidase Inhibitors.

Squalene epoxidase, also called squalene monooxygenase, catalyzes the oxidation of squalene in the cholesterol biosynthesis pathway. Thus, agents that inhibit squalene epoxidase are useful in preventing or slowing the cholesterol production. Non-limiting examples of squalene epoxidase inhibitors include terbinafine, naftifine, amorolfine, butenafine, FR194738, NB-598, resveratrol (trans-3,4',5-trihydroxystilbene), epigallocatechin-3-O-gallate, S-allylcysteine, selenocysteine, alliin, diallyl trisulfide, diallyl disulfide, and combinations thereof.

One or more squalene epoxidase inhibitors, if desired, are typically present in a composition of the invention (or co-administered with EPA according to other embodiments of the invention) in an amount of about 100 mg to 250 mg, for example about 100 mg, about 125 mg, about 150 mg, about 175 mg, about 200 mg, about 225 mg, or about 250 mg; or in an amount of about 0.5% to about 5%, by weight of the composition, for example about 0.5%, about 0.75%, about 1%, about 1.25%, about 1.5%, about 1.75%, about 2%, about 2.25%, about 2.5%, about 2.75%, about 3%, about 3.25%, about 3.5%, about 3.75%, about 4%, about 4.25%, about 4.5%, about 4.75%, or about 5%, by weight.

Thrombolytic Agents.

Thrombolytic agents dissolve blood clots. Thrombolytic agents are therefore useful in treating cardiovascular diseases and disorders including, for example, deep vein thrombosis, pulmonary embolism, ischemic complications, unstable angina, myocardial infarction, and venous thromboembolism, among others. Non-limiting examples of thrombolytic agents include fondoparinux, dalteparin, enoxaparin, apixaban, PD-348292, and combinations thereof.

One or more thrombolytic agents, if desired, are typically present in a composition of the invention (or co-administered with EPA according to other embodiments of the invention) in an amount sufficient to provide a dosage of about 0.5 mg per kg of body weight ("mg per kg") to about 40 mg per kg, for example about 0.5 mg per kg, about 1 mg per kg, about 2 mg per kg, about 3 mg per kg, about 4 mg per kg, about 5 mg per kg, about 6 mg per kg, about 7 mg per kg, about 8 mg per kg, about 9 mg per kg, about 10 mg per kg, about 11 mg per kg, about 12 mg per kg, about 13 mg per kg, about 14 mg per kg, about 15 mg per kg, about 16 mg per kg, about 17 mg per kg, about 18 mg per kg, about 19 mg per kg, about 20 mg per kg, about 21 mg per kg, about 22 mg per kg, about 23 mg per kg, about 24 mg per kg, about 25 mg per kg, about 26 mg per kg, about 27 mg per kg, about 28 mg per kg, about 29 mg per kg, about 30 mg per kg, about 31 mg per kg, about 32 mg per kg, about 33 mg per kg, about 34 mg per kg, about 35 mg per kg, about 36 mg per kg, about 37 mg per kg, about 38 mg per kg, about 39 mg per kg, or about 40 mg per kg, or in a total amount of about 30 mg to about 3.5 g.

In another embodiment, one or more thrombolytic agents are present in a composition of the invention (or co-administered with EPA according to other embodiments of the invention) in an amount of about 0.5 mg to about 2.5 mg, for example 0.5 mg, about 0.75 mg, about 1 mg, about 1.25 mg, about 1.5 mg, about 1.75 mg, about 2 mg, about 2.25 mg, or about 2.5 mg; or in an amount sufficient to provide about 60 international units per kg of body weight ("IU per kg") to about 240 IU per kg, for example 60 IU per kg, about 70 IU per kg, about 80 IU per kg, about 90 IU per kg, about 100 IU per kg, about 110 IU per kg, about 120 IU per kg, about 130 IU per kg, about 140 IU per kg, about 150 IU per kg, about 160 IU per kg, about 170 IU per kg, about 180 IU per kg, about 190 IU per kg, about 200 IU per kg, about 210 IU per kg, about 220 IU per kg, about 230 IU per kg, or about 240 IU per kg.

Other Cardiovascular Agents.

Other cardiovascular agents are also useful in preventing, inhibiting, or treating cardiovascular diseases or disorders. Non-limiting examples of other cardiovascular agents include gemfibrozil, niaspan, orlistat, GFT14, AZD-2479, ETC-1001, and combinations thereof.

One or more of these other cardiovascular agents, if desired, can be present in a composition of the invention (or may be co-administered with EPA according to other embodiments of the invention) in an amount corresponding to the recommended or suggested dosage for the particular cardiovascular agent(s). In a related embodiment, the cardiovascular agent(s) may be present in a composition of the invention (or may be co-administered with EPA according to other embodiments of the invention) in an amount less than the recommended or suggested dosage for the particular cardiovascular agent(s). For example, a composition of the invention may comprise EPA and one or more of these other cardiovascular agents in an amount of about 5 mg to about 1500 mg for example about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 266 mg, about 275 mg, about 300 mg, about 324 mg, about 325 mg, about 330 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, or about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, or about 1500 mg.

Headings used to describe cardiovascular agents herein are not to be construed as limiting in any manner. Many cardiocascular agents can have multiple modes of action and can be described under one or more headings.

Salts and Other Derivatives

Salts, hydrates, solvate, esters, amides, enantiomers, isomers, tautomers, polymorphs, prodrugs, and derivatives of any of the foregoing drugs may be used in accordance with the invention and may be prepared using standard procedures known to those skilled in the art of synthetic organic chemistry. See, e.g., March, Advanced Organic Chemistry: Reactions, Mechanisms and Structure, 4th Ed. (New York: Wiley-Interscience, 1992); Leonard et al., Advanced Practical Organic Chemistry (1992); Howarth et al., Core Organic Chemistry (1998); and Weisermel et al., Industrial Organic Chemistry (2002).

"Pharmaceutically acceptable salts," or "salts," include the salt of a drug prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta-hydroxybutyric, galactaric and galacturonic acids.

In one embodiment, acid addition salts are prepared from the free base forms using conventional methodology involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

In another embodiment, base addition salts are prepared from the free acid forms using conventional methodology involving reaction of the free acid with a suitable base.

In other embodiments, an acid addition salt is reconverted to the free base by treatment with a suitable base. In a further embodiment, the acid addition salts are halide salts, which are prepared using hydrochloric or hydrobromic acids. In still other embodiments, the basic salts are alkali metal salts, e.g., sodium salt. In other embodiments, a base addition salt is reconverted to the free acid by treatment with a suitable acid.

In one embodiment, EPA and one or more cardiovascular agent(s) are present in a composition of the invention, or are co-administered in a weight ratio of EPA:cardiovascular agent of about 1:1000 to about 1000:1, about 1:500 to about 500:1, about 1:100 to about 100:1, about 1:50 to about 50:1, about 1:25 to about 25:1, about 1:10 to about 10:1, about 1:5 to about 5:1, about 1:4 to about 4:1 about 1:3 to about 3:1, about 1:2 to about 2:1 or about 1:1.

Antiretroviral Therapy

In one embodiment, the present invention provides a method of treating a cardiovascular-related disease as defined herein, for example dyslipidemia or hyperlipidemia, in an HIV positive subject. In another embodiment, the method comprises co-administration, or concomitant administration, of a composition or compositions as disclosed herein with one or more HIV-1 protease inhibitors. Non-limiting examples of HIV-1 protease inhibitors include amprenavir, fosamprenavir, indinavir, lopinavir, nelfinavir, ritonavir and saquinavir.

One or more HIV-1 protease inhibitors, if desired, are typically present in a composition of the invention (or co-administered with EPA according to other embodiments of the invention) in an amount of about 100 mg to about 2500 mg, for example about 125 mg, about 150 mg, about 175 mg, about 200 mg, about 225 mg, about 250 mg, about 300 mg, about 350 mg, about 400 mg, about 450 mg, about 500 mg, about 550 mg, about 600 mg, about 625 mg, about 650 mg, about 700 mg, about 800 mg, about 900 mg, about 1000 mg, about 1100 mg, about 1200 mg, about 1250 mg, about 1300 mg, about 1400 mg, about 1500 mg, about 1600 mg, about 1700 mg, about 1800 mg, about 1825 mg, about 1900 mg, about 2000 mg, about 2100 mg, about 2200 mg, about 2300 mg, about 2400 mg, or about 2500 mg; in an amount of about 200 mg to about 1000 mg, for example about 200 mg, about 300 mg, about 400 mg, about 500 mg, about 600 mg, about 700 mg, about 800 mg, about 900 mg, or about 1000 mg; in an amount of about 50 mg to about 400 mg, for example about 50 mg, about 100 mg, about 150 mg, about 200 mg, about 250 mg, about 300 mg, about 350 mg, or about 400 mg; in an amount of about 200 mg to about 1066 mg, for example about 200 mg, about 250 mg, about 300 mg, about 350 mg, about 400 mg, about 450 mg, about 500 mg, about 533 mg, about 550 mg, about 600 mg, about 650 mg, about 700 mg, about 750 mg, about 800 mg, about 850 mg, about 900 mg, about 950 mg, about 1000 mg, or about 1066 mg; in an amount of about 50 mg to about 1200 mg, for example about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, or about 1200 mg; or in an amount of about 15 mg per kg body weight to about 40 mg per kg body weight, for example about 15 mg per kg, about 20 mg per kg, about 25 mg per kg, about 30 mg per kg, about 35 mg per kg, about mg per kg, or about 40 mg per kg.

Dosage Forms

In one embodiment, compositions of the invention are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration.

In some embodiments, compositions of the invention are in the form of solid dosage forms. Non-limiting examples of suitable solid dosage forms include tablets (e.g. suspension tablets, bite suspension tablets, rapid dispersion tablets, chewable tablets, melt tablets, effervescent tablets, bilayer tablets, etc), caplets, capsules (e.g. a soft or a hard gelatin capsule filled with solid and/or liquids), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

EPA and/or any other desired cardiovascular agent(s) can be co-formulated in the same dosage unit, or can be individually formulated in separate dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, a composition of the invention comprises one or more cardiovascular agents dispersed or suspended in EPA, wherein the dispersion or suspension is present in a capsule (for example gelatin or HPMC capsule), sachet, or other dosage form or carrier as described herein. In another embodiment, the dispersion or suspension is substantially uniform. In still another embodiment, where co-administration of two or more dosage units is desired, the EPA is present in a first dosage unit, for example a suspension in a capsule, and the cardiovascular agent is present in second dosage unit, for example a tablet. Optionally, any desired additional cardiovascular agent can be present in a third composition.

In another embodiment, composition(s) of the invention can be in the form of liquid dosage forms or dose units to be imbibed directly or they can be mixed with food or beverage prior to ingestion. Non-limiting examples of suitable liquid dosage forms include solutions, suspension, elixirs, syrups, liquid aerosol formulations, etc.

In one embodiment, compositions of the invention, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

In another embodiment, the invention provides a pharmaceutical composition comprising EPA and a cardiovascular agent (fill) encapsulated in a capsule shell, wherein the fill has a baseline peroxide value not greater than about 10 Meq/kg, about 9 Meq/kg, about 8 Meq/kg, about 7 Meq/kg, about 6 Meq/kg, about 5 Meq/kg, about 4 Meq/kg, about 3 Meq/kg or about 2 Meq/kg, wherein upon storage of the composition at 23° C. and 50% RH for a period about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23 or about 24 months, the ultra-pure EPA has a second peroxide value not greater than about 25 Meq/kg, about 24 Meq/kg, about 23 Meq/kg, about 22 Meq/kg, about 21 Meq/kg, about 20 Meq/kg, about 19 Meq/kg, about 18 Meq/kg, about 17 Meq/kg, about 16 Meq/kg, about 15 Meq/kg, about 14 Meq/kg, about 13 Meq/kg, about 12 Meq/kg, about 11 Meq/kg, about 10 Meq/kg, about 9 Meq/kg, about 8 Meq/kg, about 7 Meq/kg, about 6 Meq/kg, about 5 Meq/kg, about 4 Meq/kg, about 3 Meq/kg or about 2 Meq/kg.

Upon storage, some pharmaceutical compositions degrade over time. Degradation products can alter a composition's efficacy, for example by delivering less active ingredient to a subject than recommended. Degradation products for new drugs above certain thresholds should be reported to the Food & Drug Administration (FDA) in accordance with current Guidance Documents. Degradation products above a certain threshold amount should be identified. A degradation product is "identified" when its structural characterization has been achieved. Degradation products above a certain amount should be qualified. A degradation product is "qualified" when its biological safety is acquired and evaluated.

In one embodiment, compositions of the invention with a maximum daily dose of less than or equal to 1 gram, upon storage under light, heat, humidity, acid/base hydrolytic, and/or oxidative conditions, contain less than about 0.1% of any degradation product not reported to the Food and Drug Administration (FDA). In another embodiment, compositions of the invention with a maximum daily dose of greater than 1 gram, upon storage under light, heat, humidity, acid/base hydrolytic, and/or oxidative conditions, contain less than about 0.05% of any degradation product not reported to the FDA.

In one embodiment, compositions of the invention with a maximum daily dose of less than 1 mg, upon storage under light, heat, humidity, acid/base hydrolytic, and/or oxidative conditions, contain less than about 1% of any unidentified degradation product. In another embodiment, compositions of the invention with a maximum daily dose of less than 1 mg, upon storage under light, heat, humidity, acid/base hydrolytic, and/or oxidative conditions, contain less than about 5 µg of any unidentified degradation product.

In one embodiment, compositions of the invention with a maximum daily dose of 1 mg to 10 mg, upon storage under light, heat, humidity, acid/base hydrolytic, and/or oxidative conditions, contain less than about 0.5% of any unidentified degradation product. In another embodiment, compositions of the invention with a maximum daily dose of 1 mg to 10 mg, upon storage under light, heat, humidity, acid/base hydrolytic, and/or oxidative conditions, contain less than about 20 µg of any unidentified degradation product.

In one embodiment, compositions of the invention with a maximum daily dose of 10 mg to 2 g, upon storage under light, heat, humidity, acid/base hydrolytic, and/or oxidative conditions, contain less than about 0.2% of any unidentified degradation product. In another embodiment, compositions of the invention with a maximum daily dose of 10 mg to 2 g, upon storage under light, heat, humidity, acid/base hydrolytic, and/or oxidative conditions, contain less than about 2 mg of any unidentified degradation product.

In one embodiment, compositions of the invention with a maximum daily dose of greater than 2 g, upon storage under light, heat, humidity, acid/base hydrolytic, and/or oxidative conditions, contain less than about 0.1% of any unidentified degradation product.

In one embodiment, compositions of the invention with a maximum daily dose of less than 10 mg, upon storage under light, heat, humidity, acid/base hydrolytic, and/or oxidative conditions, contain less than about 1% of any unqualified degradation product. In another embodiment, compositions of the invention with a maximum daily dose of less than 10 mg, upon storage under light, heat, humidity, acid/base hydrolytic, and/or oxidative conditions, contain less than about 50 µg of any unqualified degradation product.

In one embodiment, compositions of the invention with a maximum daily dose of 10 mg to 100 mg, upon storage under light, heat, humidity, acid/base hydrolytic, and/or oxidative conditions, contain less than about 0.5% of any unqualified degradation product. In another embodiment, compositions of the invention with a maximum daily dose of 10 mg to 100 mg, upon storage under light, heat, humidity, acid/base hydrolytic, and/or oxidative conditions, contain less than about 200 µg of any unqualified degradation product.

In one embodiment, compositions of the invention with a maximum daily dose of 100 mg to 2 g, upon storage under light, heat, humidity, acid/base hydrolytic, and/or oxidative conditions, contain less than about 0.2% of any unqualified degradation product. In another embodiment, compositions of the invention with a maximum daily dose of 100 mg to 2 g, upon storage under light, heat, humidity, acid/base hydrolytic, and/or oxidative conditions, contain less than about 3 mg of any unqualified degradation product.

In one embodiment, compositions of the invention with a maximum daily dose of greater than 2 g, upon storage under light, heat, humidity, acid/base hydrolytic, and/or oxidative conditions, contain less than about 0.15% of any unqualified degradation product.

In some embodiments, compositions of the invention comprise a stabilizing agent that suppresses, prevents, hinders, or otherwise attenuates the decomposition of the active ingredient(s) during storage. For example, oxidative decomposition of EPA in compositions of the invention may be prevented or attenuated by the presence of antioxidants. Non-limiting examples of suitable antioxidants include tocopherol, lecithin, citric acid and/or ascorbic acid. One or more antioxidants, if desired, are typically present in a composition in an amount of about 0.01% to about 0.1%, by weight, or about 0.025% to about 0.05%, by weight.

Excipients

Compositions of the invention optionally comprise one or more pharmaceutically acceptable excipients. The term "pharmaceutically acceptable excipient" herein means any substance, not itself a therapeutic agent, used as a carrier or vehicle for delivery of a therapeutic agent to a subject or added to a pharmaceutical composition to improve its handling or storage properties or to permit or facilitate formation of a unit dose of the composition, and that does not produce unacceptable toxicity or interaction with other components in the composition.

Compositions of the invention optionally comprise one or more pharmaceutically acceptable diluents as excipients. Suitable diluents illustratively include, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of a- and amorphous cellulose (e.g., Rexcel™) and powdered cellulose; calcium carbonate; glycine; bentonite; polyvinylpyrrolidone; and the like. Such diluents, if present, constitute in total about 5% to about 99%, about 10% to about 85%, or about 20% to about 80%, of the total weight of the composition.

Compositions of the invention optionally comprise one or more pharmaceutically acceptable disintegrants as excipients. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, xanthan, locust bean, karaya, pectin and tragacanth gums. Such disintegrants, if present, typically comprise in total about 0.2% to about 30%, about 0.2% to about 10%, or about 0.2% to about 5%, of the total weight of the composition.

Compositions of the invention optionally comprise one or more antioxidants. Illustrative antioxidants include sodium ascorbate and vitamin E (tocopherol). One or more antioxidants, if present, are typically present in a composition of the invention in an amount of about 0.001% to about 5%, about 0.005% to about 2.5%, or about 0.01% to about 1%, by weight.

Compositions of the invention optionally comprise one or more pharmaceutically acceptable binding agents or adhesives as excipients. Such binding agents and adhesives can impart sufficient cohesion to a powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, about 0.75% to about 15%, or about 1% to about 10%, of the total weight of the composition.

Compositions of the invention optionally comprise one or more pharmaceutically acceptable wetting agents as excipients. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, about 0.4% to about 10%, or about 0.5% to about 5%, of the total weight of the composition.

Compositions of the invention optionally comprise one or more pharmaceutically acceptable lubricants (including anti-adherents and/or glidants) as excipients. Suitable lubricants include, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, about 0.2% to about 8%, or about 0.25% to about 5%, of the total weight of the composition.

Suitable anti-adherents include talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, constitutes about 0.1% to about 10%, about 0.25% to about 5%, or about 0.5% to about 2%, of the total weight of the composition. Glidants can be used to promote powder flow of a solid formulation. Suitable glidants include colloidal silicon dioxide, starch, talc, tribasic calcium phosphate, powdered cellulose and magnesium trisilicate.

Compositions of the present invention optionally comprise one or more flavoring agents, sweetening agents, and/or colorants. Flavoring agents useful in the present invention include, without limitation, acacia syrup, alitame, anise, apple, aspartame, banana, Bavarian cream, berry, black currant, butter, butter pecan, butterscotch, calcium citrate, camphor, caramel, cherry, cherry cream, chocolate, cinnamon, citrus, citrus punch, citrus cream, cocoa, coffee, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, MagnaSweet®, maltol, mannitol, maple, menthol, mint, mint cream, mixed berry, nut, orange, peanut butter, pear, peppermint, peppermint cream, Prosweet® Powder, raspberry, root beer, rum, saccharin, safrole, sorbitol, spearmint, spearmint cream, strawberry, strawberry cream, stevia, sucralose, sucrose, Swiss cream, tagatose, tangerine, thaumatin, tutti fruitti, vanilla, walnut, watermelon, wild cherry, wintergreen, xylitol, and combinations thereof, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, etc.

Sweetening agents that can be used in the present invention include, for example, acesulfame potassium (acesulfame K), alitame, aspartame, cyclamate, cylamate, dextrose, isomalt, MagnaSweet®, maltitol, mannitol, neohesperidine DC, neotame, Prosweet® Powder, saccharin, sorbitol, stevia, sucralose, sucrose, tagatose, thaumatin, xylitol, and the like.

Flavoring agents, sweetening agents, and/or colorants can be present in compositions of the invention in any suitable amount, for example about 0.01% to about 10%, about 0.1% to about 8%, or about 1% to about 5%, by weight.

Compositions of the invention optionally comprise a suspending agent. Non-limiting illustrative examples of suitable suspending agents include silicon dioxide, bentonite, hydrated aluminum silicate (e.g. kaolin) and mixtures thereof. One or more suspending agents are optionally present in compositions of the invention in a total amount of about 0.01% to about 3.0%, about 0.1% to about 2.0%, or about 0.25% to about 1.0%, by weight.

The foregoing excipients can have multiple roles as is known in the art. For example, starch can serve as a filler as well as a disintegrant. The classification of excipients above is not to be construed as limiting in any manner. Excipients categorized in any manner may also operate under various different categories of excipients as will be readily appreciated by one of ordinary skill in the art.

Therapeutic Methods

In various embodiments, compositions of the invention are useful for treatment and/or prevention of a cardiovascular-related disease. The term "cardiovascular-related disease" herein refers to any disease or disorder of the heart or blood vessels (i.e. arteries and veins) or any symptom thereof, or any disease or condition that causes or contributes to a cardiovascular disease." Non-limiting examples of cardiovascular-related diseases and disorders include acute cardiac ischemic events, acute myocardial infarction, angina, angina pectoris, arrhythmia, atrial fibrulation, atherosclerosis, arterial fibrillation, cardiac insufficiency, cardiovascular disease, chronic heart failure, chronic stable angina, congestive heart failure, coronary artery disease, coronary heart disease, deep vein thrombosis, diabetes, diabetes mellitus, diabetic neuropathy, diastolic dysfunction in subjects with diabetes mellitus, edema, essential hypertension, eventual pulmonary embolism, fatty liver disease, heart disease, heart failure, homozygous familial hypercholesterolemia (HoFH), homozygous familial sitosterolemia, hypercholesterolemia, hyperlipidemia, hyperlipidemia in HIV positive subjects, hypertension, hypertriglyceridemia, ischemic complications in unstable angina and myocardial infarction, low blood pressure, metabolic syndrome, mixed dyslipidemia, moderate to mild heart failure, myocardial infarction, obesity management, paroxysmal atrial/arterial fibrillation/fibrulation/flutter, paroxysmal supraventricular tachycardias (PSVT), particularly severe or rapid onset edema, platelet aggregation, primary hypercholesterolemia, primary hyperlipidemia, pulmonary arterial hypertension, pulmonary hypertension, recurrent hemodynamically unstable ventricular tachycardia (VT), recurrent ventricular arrhythmias, recurrent ventricular fibrillation (VF), ruptured aneurysm, sitisterolemia, stroke, supraventricular tachycardia, symptomatic atrial fibrillation/flutter, tachycardia, type-II diabetes, vascular disease, venous thromboembolism, ventricular arrhythmias, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In some embodiments, compositions of the present invention can be co-administered or administered concomitantly with one or more additional cardiovascular agents. The terms "co-administered," "concomitant administration," and "administered concomitantly" are used interchangeably herein and each refer to, for example, administration of two or more agents (e.g., EPA or a derivative thereof and a cardiovascular agent) at the same time, in the same dosage unit, one immediately after the other, within five minutes of each other, within ten minutes of each other, within fifteen minutes of each other, within thirty minutes of each other, within one hour of each other, within two hours of each other, within four hours of each other, within six hours of each other, within twelve hours of each other, within one day of each other, within one week of each other, within two weeks of each other, within one month of each other, within two months of each other, within six months of each other, within one year of each other, etc.

In one embodiment, the present invention provides a method of treating a cardiovascular-related disease comprising administering to a subject in need thereof a composition or compositions comprising EPA and one or more additional cardiovascular agents (either as a single dosage unit or as multiple dosage units), wherein one or more lipid parameters are improved by comparison with lipid parameters achieved by the additive effects of the individual treatments.

In a related embodiment, upon treatment in accordance with the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits one or more of the following outcomes:

a) reduced triglyceride levels compared to baseline or a placebo arm;
b) reduced Apo B levels compared to baseline or a placebo arm;
c) increased HDL-C levels compared to baseline or a placebo arm;
d) no increase in LDL-C levels compared to baseline or a placebo arm;
e) a reduction in LDL-C levels compared to baseline or a placebo arm;
f) a reduction in non-HDL-C levels compared to baseline or a placebo arm;
g) a reduction in vLDL levels compared to baseline or a placebo arm;
h) an increase in apo A-I levels compared to baseline or a placebo arm;
i) an increase in apo A-I/apo B ratio compared to baseline or a placebo arm;
j) a reduction in lipoprotein A levels compared to baseline or a placebo arm;
k) an increase in LDL particle number compared to baseline or a placebo arm;
l) a reduction in LDL size compared to baseline or a placebo arm;
m) a reduction in remnant-like particle cholesterol compared to baseline or a placebo arm;
n) a reduction in oxidized LDL compared to baseline or a placebo arm;
o) no change or a reduction in fasting plasma glucose (FPG) compared to baseline or a placebo arm;
p) a reduction in hemoglobin $A_{1c}$ (Hb$A_{1c}$) compared to baseline or a placebo arm;
q) a reduction in homeostasis model insulin resistance compared to baseline or a placebo arm;
r) a reduction in lipoprotein associated phospholipase A2 compared to baseline or a placebo arm;
s) a reduction in intracellular adhesion molecule-1 compared to baseline or a placebo arm;
t) a reduction in interleukin-6 compared to baseline or a placebo arm;
u) a reduction in plasminogen activator inhibitor-1 compared to baseline or a placebo arm;
v) a reduction in high sensitivity C-reactive protein (hsCRP) compared to baseline or a placebo arm;
w) an increase in serum phospholipid EPA compared to baseline or a placebo arm;
x) an increase in red blood cell membrane EPA compared to baseline or a placebo arm; and/or
y) a reduction or increase in one or more of serum phospholipid and/or red blood cell content of docosahexaenoic acid (DHA), docosapentaenoic acid (DPA), arachidonic acid (AA), palmitic acid (PA), staeridonic acid (SA) or oleic acid (OA) compared to baseline or a placebo arm.

In one embodiment, methods of the present invention comprise measuring baseline levels of one or more markers set forth in (a)-(y) above prior to dosing the subject or subject group. In another embodiment, the methods comprise administering a composition as disclosed herein to the subject after baseline levels of one or more markers set forth in (a)-(y) are determined, and subsequently taking an additional measurement of said one or more markers.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more, any 24 or more, or all 25 of outcomes (a)-(y) described immediately above.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 10 weeks, about 1 to about 5 weeks, about 1 to about 2 weeks or about 1 week, the subject or subject group exhibits one or more of the following outcomes:

a) a reduction in triglyceride level of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

b) a less than 30% increase, less than 20% increase, less than 10% increase, less than 5% increase or no increase in non-HDL-C levels or a reduction in non-HDLG levels of at least about 1%, at least about 3%, at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

c) substantially no change, no change or an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

d) a less than 60% increase, less than 50% increase, less than 40% increase, less than 30% increase, less than 20% increase, less than 15% increase or no increase in LDL-C levels or a reduction in LDL-C levels of at least about 5%, at least about 10%, at least about 15%, at least about 20%, at least about 25%, at least about 30%, at least about 35%, at least about 40%, at least about 45%, at least about 50%, at least about 55%, at least about 55% or at least about 75% (actual % change or median % change) as compared to baseline or a placebo arm;

e) a decrease in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) as compared to baseline or a placebo arm;

f) a reduction in vLDL levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

g) an increase in apo A-I levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

h) an increase in apo A-I/apo B ratio of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

i) a reduction in lipoprotein(a) levels of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

j) a reduction in mean LDL particle number of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

k) an increase in mean LDL particle size of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

l) a reduction in remnant-like particle cholesterol of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

m) a reduction in oxidized LDL of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

n) substantially no change, no change or a reduction in fasting plasma glucose (FPG) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

o) substantially no change, no change or a reduction in hemoglobin $A_{1c}$ ($HbA_{1c}$) of at least about 5%, at least about 10%, at least about 15%, at least about 20%, at least about 25%, at least about 30%, at least about 35%, at least about 40%, at least about 45%, or at least about 50% (actual % change or median % change) compared to baseline or a placebo arm;

p) a reduction in homeostasis model index insulin resistance of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

q) a reduction in lipoprotein associated phospholipase A2 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

r) a reduction in intracellular adhesion molecule-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

s) a reduction in interleukin-6 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

t) a reduction in plasminogen activator inhibitor-1 of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

u) a reduction in high sensitivity C-reactive protein (hsCRP) of at least about 5%, at least about 10%, at least about 15%, at least about 20%, at least about 25%, at least about 30%, at least about 35%, at least about 40%, at least about 45%, at least about 50%, or at least about 100% (actual % change or median % change) compared to baseline or a placebo arm;

v) an increase in serum plasma and/or RBC EPA of at least about 5%, at least about 10%, at least about 15%, at least about 20%, at least about 25%, at least about 30%, at least about 35%, at least about 40%, at least about 45%, at least about 50%, at least about 100%, at least about 200% or at least about 400% (actual % change or median % change) compared to baseline or a placebo arm;

w) an increase in serum phospholipid and/or red blood cell membrane EPA of at least about 5%, at least about 10%, at least about 15%, at least about 20%, at least about 25%, at least about 30%, at least about 35%, at least about 40%, at least about 45%, r at least about 50%, at least about 100%, at least about 200%, or at least about 400% (actual % change or median % change) compared to baseline or a placebo arm;

x) a reduction or increase in one or more of serum phospholipid and/or red blood cell DHA, DPA, AA, PA and/or OA of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or a placebo arm; and/or y) (y) a reduction in total cholesterol of at least about 5%, at least about 10%, at least about 15%, at least about 20%, at least about 25%, at least about 30%, at least about 35%, at least about 40%, at least about 45%, at least about 50%, at least about 55% or at least about 75% (actual % change or median % change) compared to baseline or a placebo arm.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In another embodiment, upon treatment with a composition of the present invention, for example over a period of about 1 to about 200 weeks, about 1 to about 100 weeks, about 1 to about 80 weeks, about 1 to about 50 weeks, about 1 to about 40 weeks, about 1 to about 20 weeks, about 1 to about 15 weeks, about 1 to about 12 weeks, about 1 to about 10 weeks, about 1 to about 5 weeks, about 1 to about 2 weeks or about 1 week, the subject or subject group exhibits any 2 or more of, any 3 or more of, any 4 or more of, any 5 or more of, any 6 or more of, any 7 or more of, any 8 or more of, any 9 or more of, any 10 or more of, any 11 or more of, any 12 or more of, any 13 or more of, any 14 or more of, any 15 or more of, any 16 or more of, any 17 or more of, any 18 or more of, any 19 or more of, any 20 or more of, any 21 or more of, any 22 or more of, any 23 or more of, any 24 or more of, or all 25 of outcomes (a)-(y) described immediately above.

Parameters (a)-(y) can be measured in accordance with any clinically acceptable methodology. For example, triglycerides, total cholesterol, HDL-C and fasting blood sugar can be sample from serum and analyzed using standard photometry techniques. VLDL-TG, LDL-C and VLDL-C can be calculated or determined using serum lipoprotein fractionation by preparative ultracentrifugation and subsequent quantitative analysis by refractometry or by analytic ultracentrifugal methodology. Apo A1, Apo B and hsCRP can be determined from serum using standard nephelometry techniques. Lipoprotein (a) can be determined from serum using standard turbidimetric immunoassay techniques. LDL particle number and particle size can be determined using nuclear magnetic resonance (NMR) spectrometry. Remnants lipoproteins and LDL-phospholipase A2 can be determined from EDTA plasma or serum and serum, respectively, using enzymatic immunoseparation techniques. Oxidized LDL, intercellular adhesion molecule-1 and interleukin-2 levels can be determined from serum using standard enzyme immunoassay techniques. These techniques are described in detail in standard textbooks, for example Tietz Fundamentals of Clinical Chemistry, 6th Ed. (Burtis, Ashwood and Borter Eds.), WB Saunders Company.

In a related embodiment, the reductions or increases of parameters (a)-(y) above are statistically significant.

In another embodiment, the present invention provides a method of blood lipid therapy comprising administering to a subject in need thereof 1 to a plurality of dosage units comprising a composition or compositions as disclosed herein. In another embodiment, the subject being treated has a baseline triglyceride level, prior to treatment with a composition of the present invention, greater than or equal to about 150 mg/dl, greater than or equal to about 175 mg/dl, greater than or equal to about 250 mg/dl, or greater than or equal to about 500 mg/dl, for example about 200 mg/dl to about 2000 mg/dl, about 300 to about 1800 mg/dl, or about 500 mg/dl to about 1500 mg/dl.

In one embodiment, methods of the present invention comprise measuring baseline levels of one or more markers set forth in (a)-(y) prior to dosing the subject or subject group. In another embodiment, the methods comprise administering a composition as disclosed herein to the subject after baseline levels of one or more markers set forth in (a)-(y) are determined, and subsequently taking a second measurement of the one or more markers as measured at baseline for comparison thereto.

In one embodiment, the present invention provides a method of treating or preventing primary hypercholesteremia and/or mixed dyslipidemia (Fredrickson Types IIa and IIb) in a subject in need thereof, comprising administering to the subject a composition or compositions comprising EPA and one or more additional cardiovascular agents (either as a single dosage unit or as multiple dosage units) as disclosed herein. In a related embodiment, the present invention provides a method of reducing triglyceride levels in a subject or subjects when treatment with a statin or niacin extended-release monotherapy is considered inadequate (Frederickson type IV hyperlipidemia). Statin or niacin extended-release monotherapy is considered inadequate when, for example, the subject's non-HDL-C level is not lowered or is not lowered to the degree desired, the subject's LDL-C level is not improved or is not improved to the degree desired, the subject's HDL-C level is not improved or is not improved to the degree desired, and/or the subject's triglyceride level is not improved or is not improved to the degree desired.

In another embodiment, the present invention provides a method of treating or preventing nonfatal myocardial infarction, comprising administering to the subject a composition or compositions comprising EPA and one or more additional cardiovascular agents (either as a single dosage unit or as multiple dosage units) as disclosed herein.

In another embodiment, the present invention provides a method of treating or preventing risk of recurrent nonfatal myocardial infarction in a subject with a history of myocardial infarction, comprising administering to the subject a composition or compositions comprising EPA and one or more additional cardiovascular agents (either as a single dosage unit or as multiple dosage units) as disclosed herein.

In another embodiment, the present invention provides a method of slowing progression of or promoting regression of atherosclerotic disease in a subject in need thereof, comprising administering to the subject a composition or compositions comprising EPA and one or more additional cardiovascular agents (either as a single dosage unit or as multiple dosage units) as disclosed herein.

In another embodiment, the present invention provides a method of treating obesity in a subject in need thereof, comprising administering to a subject in need thereof a composition or compositions comprising EPA and one or more additional cardiovascular agents (either as a single dosage unit or as multiple dosage units) as disclosed herein.

In another embodiment, the present invention provides a method of treating or preventing very high serum triglyceride levels (e.g. Types IV and V hyperlipidemia) in a subject in need thereof, comprising administering to the subject a composition or compositions comprising EPA and one or more additional cardiovascular agents (either as a single dosage unit or as multiple dosage units) as disclosed herein.

In another embodiment, the present invention provides a method of treating subjects having very high serum triglyceride levels (e.g. greater than 1000 mg/dl or greater than 2000 mg/dl) and that are at risk of developing pancreatitis, comprising administering to the subject a composition or compositions comprising EPA and one or more additional cardiovascular agents (either as a single dosage unit or as multiple dosage units) as disclosed herein.

In another embodiment, the present invention provides a method of preventing recurrence of stroke, comprising administering to a subject with a history of stroke a composition or compositions comprising EPA and one or more additional cardiovascular agents (either as a single dosage unit or as multiple dosage units) as disclosed herein.

In another embodiment, the present invention provides a method of preventing onset and/or recurrence of cardiovascular events in a subject who has escaped the unstable period after cardiovascular angioplasty, comprising administering to the subject a composition or compositions comprising EPA and one or more additional cardiovascular agents (either as a single dosage unit or as multiple dosage units) as disclosed herein.

In another embodiment, the present invention provides a method of reducing Apo-B and non-HDL cholesterol levels in a subject group with a baseline LDL-cholesterol level of at least 100 mg/dl, a baseline non-HDL-cholesterol level of at least 130 mg/dl and a baseline triglyceride level of at least 200 mg/dl, and reducing the Apo-B and the non-HDL-cholesterol level of the subject group by administering a composition or compositions comprising EPA and one or more additional cardiovascular agents (either as a single dosage unit or as multiple dosage units) as disclosed herein to members of the subject group.

In another embodiment, the invention provides a method of reducing Apo-B levels in a subject group, comprising measuring LDL-cholesterol, non-HDL-cholesterol, and triglyceride levels in subjects, providing a subject group with a baseline LDL-cholesterol level of at least 100 mg/dL, a baseline non-HDL-cholesterol level of at least 130 mg/dL, and a baseline triglyceride level of at least 200 mg/dL, and reducing the Apo-B levels of the subject group by administering to members of the subject group a composition or compositions comprising EPA and one or more additional cardiovascular agents (either as a single dosage unit or as multiple dosage units) as disclosed herein in an amount effective to reduce the Apo-B levels of the subject group in a statistically significant amount as compared to a control treatment, wherein an increase or statistically significant increase of LDL-cholesterol level is avoided.

In another embodiment, the invention provides a method of reducing Apo-B levels in a subject group, comprising providing a subject group with a baseline LDL-cholesterol level of at least 100 mg/dL, a baseline non-HDL-cholesterol level of at least 130 mg/dL, and a baseline triglyceride level of at least 200 mg/dL, reducing the Apo-B levels of the subject group by administering to members of the subject group a a composition or compositions comprising EPA and one or more additional cardiovascular agents (either as a single dosage unit or as multiple dosage units) as disclosed herein in an amount effective to reduce the Apo-B levels of the subject group in a statistically significant amount as compared to a control treatment, and determining the reduction in the Apo-B levels of the subject group.

In one embodiment, a composition of the invention is administered to a subject in an amount sufficient to provide a daily EPA dose of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, or about 2500 mg.

In the various embodiments of the invention described herein, the EPA and optional one or more additional cardiovascular agents can be administered as a co-formulated single dosage unit, or as individual dosage units. Where the EPA and optional one or more additional cardiovascular agents are co-administered as separate dosage units, each dosage unit can be administered to a subject at substantially the same or substantially different times. In one embodiment, where two or more individual dosage units are to be administered daily, each dosage unit can be administered to the subject within a period of about 24 hours, 18 hours, 12 hours, 10 hours, 8 hours, 6 hours, 4 hours, 2 hours, 1 hour, or 0.5 hours.

In another embodiment, the EPA and one or more optional cardiovascular agents can be administered sequentially. For example, EPA can be administered to a subject as a sole agent during an EPA loading period. The loading period can be, for example, 1 day, 2 days, 4 days, 6 days, 2 weeks, 3 weeks, 4 weeks, 5 weeks, 6 weeks, 7 weeks, 8 weeks, 9 weeks or 10 weeks. After any such loading period, one or more additional cardiovascular agents can be initiated together with current EPA administration or in place of EPA treatment.

In another embodiment, EPA is administered to a subject in the morning, for example from about 4 am to about 10 am, about 5 am to about 9 am, or about 6 am to about 8 am, and the optional one or more cardiovascular agents are administered to the subject in the afternoon or evening, for example from about 1 pm to about 11 pm, about 2 pm to about 10 pm, or about 3 pm to about 9 pm, or vice versa.

In another embodiment, the invention provides the use of EPA and one or more cardiovascular agents in the manufacture of a medicament for treatment or prevention of a cardiovascular-related disease such as hypertriglyceridemia, hypercholesterolemia, mixed dyslipidemia, coronary heart disease, vascular disease, stroke, atherosclerosis, arrhythmia, hypertension, myocardial infarction, and other cardiovascular events. In one embodiment, the composition contains not more than 10% DHA, if any. In another embodiment, the composition contains substantially no or no DHA.

In another embodiment, the invention provides a pharmaceutical composition comprising EPA and one or more cardiovascular agents for the treatment and/or prevention of a cardiovascular-related disease, wherein the composition contains not more than 10% DHA, if any. In a related embodiment, the composition contains substantially no DHA or no DHA.

In one embodiment, a subject being treated with a composition or regimen set forth herein is a diabetic or pre-diabetic subject.

In one embodiment, any of the methods disclosed herein are used in treatment or prevention of a subject or subjects that consume a traditional Western diet. In one embodiment, the methods of the invention include a step of identifying a subject as a Western diet consumer or prudent diet consumer and then treating the subject if the subject is deemed to consume a Western diet. The term "Western diet" herein refers generally to a typical diet consisting of, by percentage of total calories, about 45% to about 50% carbohydrate, about 35 to about 40% fat, and about 10% to about 15% protein. A Western diet may further be characterized by relatively high intakes of red and processed meats, sweets, refined grains, and desserts, for example where half or more or 70% or more calories come from these sources.

It is to be understood that a wide range of changes and modifications to the embodiments described above will be apparent to those skilled in the art and are contemplated. It is, therefore, intended that the foregoing detailed description be regarded as illustrative rather than limiting, and that it be understood that it is the following claims, including all equivalents, that are intended to define the spirit and scope of the invention.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

EXAMPLES

The following non-limiting examples are for illustrative purposes only and are not to be construed as limiting the invention in any manner.

Example 1

An experiment was conducted to test EPA, DHA, EPA+DHA with and without with atorvastatin in model membranes enriched with PUFAs and cholesterol at levels that reproduce disease or high CV-risk conditions (i.e. hypercholesterimia). As is shown below, EPA exhibits a potent antioxidant benefit in cholesterol-enriched membranes that was superior to that observed with DHA. Moreover, the combination of EPA and atorvastating provided even further antioxidant benefit by comparison to EPA alone.

EPA and DHA were tested individually at a fixed concentration of 10.0 uM or in combination at 5.65 µM and 4.35 µM (EPA and DHA, respectively), which is a mole ratio of 1.3:1. Separate and combined effects of these agents on lipid peroxide (LOON) formation were examined at cholesterol-to-phospholipid (C/P) mole ratios of 0.5:1, 1.0:1 and 1.5:1. Levels of lipid hydroperoxides were also measured for EPA, DPH and EPA/DPH in cholesterol-enriched membrane prepared in the absence and presence of atorvastatin.

1,2-Dilinoleoyl-3-sn-phosphatidylcholine (DLPC) was obtained from Avanti Polar Lipids (Alabaster, Ala.) and stored in chloroform (25 mg/ml) at −80° C. until use. Cholesterol obtained and stored in chloroform (10 mg/ml) at −20° C. CHOD-iodide color reagent (stock) was prepared according to a procedure modified from El-Saadani et al. (ElSaadani M, Esterbauer H, El-Sayed M, Goher M, Nassar A Y, Jurgens G. A spectrophotometric assay for lipid peroxides in serum lipoproteins using commercially available reagent. *J Lipid Res* 1989; 30:627-30) consisted of 0.2 M $K_2HPO_4$, 0.12 M KI, 0.15 mM $NaN_3$, 10 1 . . . EM ammonium molybdate, and 0.1 g/L benzalkonium chloride. Prior to experimental use, the CHOD reagent was activated by adding 24 µM ethylenediaminetetraacetic acid (EDTA), 20 µM butylated hydroxytoluene (BHT), and 0.2% Triton X-100. Atorvastatin was prepared in ethanol just prior to experimental use and added together with component lipids containing fixed amounts of EPA, DPH or EPA/DPH at equimolar levels. The compounds and lipids were added in combination during membrane sample preparation to ensure full incorporation into the lipid bilayers.

Membrane samples consisting of DLPC±cholesterol, with cholesterol-to-phospholipid (C/P) mole ratios ranging from 0.5 to 1.5, were prepared as follows. Component lipids (in chloroform) were transferred to 13×100 mm test tubes and shell-dried under a steady stream of nitrogen gas while vortex mixing. The lipid was co-dried with EPA, DPH or EPA/DPH prepared in the absence or presence of the atorvastatin at equimolar levels.

Residual solvent was removed by drying for a minimum of 3 h under vacuum. After desiccation, each membrane sample was resuspended in diffraction buffer (0.5 mM HEPES, 154 mM NaCl, pH 7.3) to yield a final phospholipid concentration of 1.0 mg/ml. Multilamellar vesicles (MLV) were formed by vortex mixing for 3 minutes at ambient temperature. Bangham A D, Standish M M, Watkins J C. Diffusion of univalent ions across the lamellae of swollen phospholipids. *J Mol Biol* 1965; 13:238-52. Immediately after initial MLV preparation, aliquots of each membrane sample will be taken for baseline (0 h) peroxidation analyses.

All lipid membrane samples were subjected to time-dependent autoxidation by incubating at 37° C. in an uncovered, shaking water bath. Small aliquots of each sample were removed at 24 h intervals and combined with 1.0 ml of active CHOD-iodide color reagent. To ensure spectrophotometric readings within the optimum absorbance range, sample volumes taken for measurement of lipid peroxide formation were adjusted for length of peroxidation and range between 100 and 10 μl. Test samples were immediately covered with foil and incubated at room temperature for >4 h in the absence of light. Absorbances were measured against a CHOD blank at 365 nm using a Beckman DU-640 spectrophotometer.

The CHOD colorimetric assay is based on the oxidation of iodide (I$^-$) by lipid hydroperoxides (LOOH) and proceeds according to the following reaction scheme:

$$LOOH + 2H^+ + 3I^- \rightarrow LOH + H_2O + I_3^-$$

The quantity of triiodide anion ($I_3^-$) liberated in this reaction is directly proportional to the amount of lipid hydroperoxides present in the membrane sample. The molar absorptivity value ($\epsilon$) of $I_3^-$ is $2.46 \times 10^4$ M$^{-1}$ cm$^{-1}$ at 365 nm.

Figure 2:
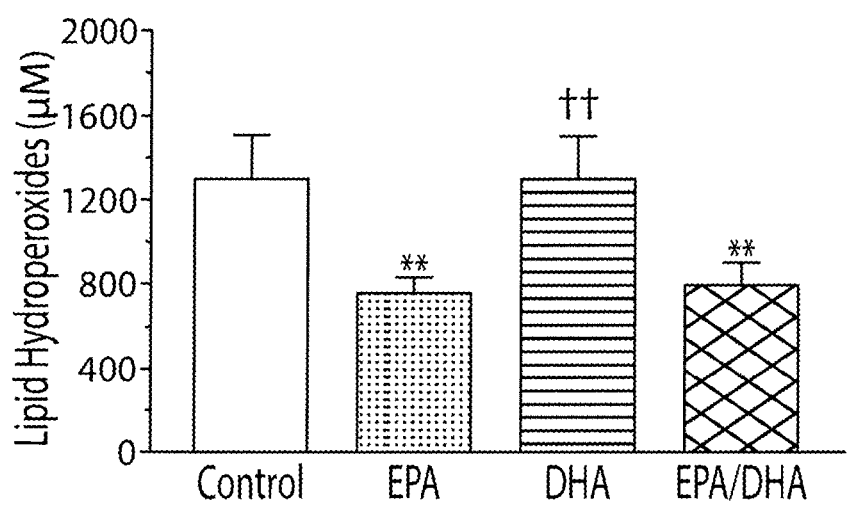
FIG. 2 shows effects of EPA, DHA and Combination Treatment on membrane lipid peroxidation at cholesterol-to-phospholipid ratio of 0.5.
Figure 3:
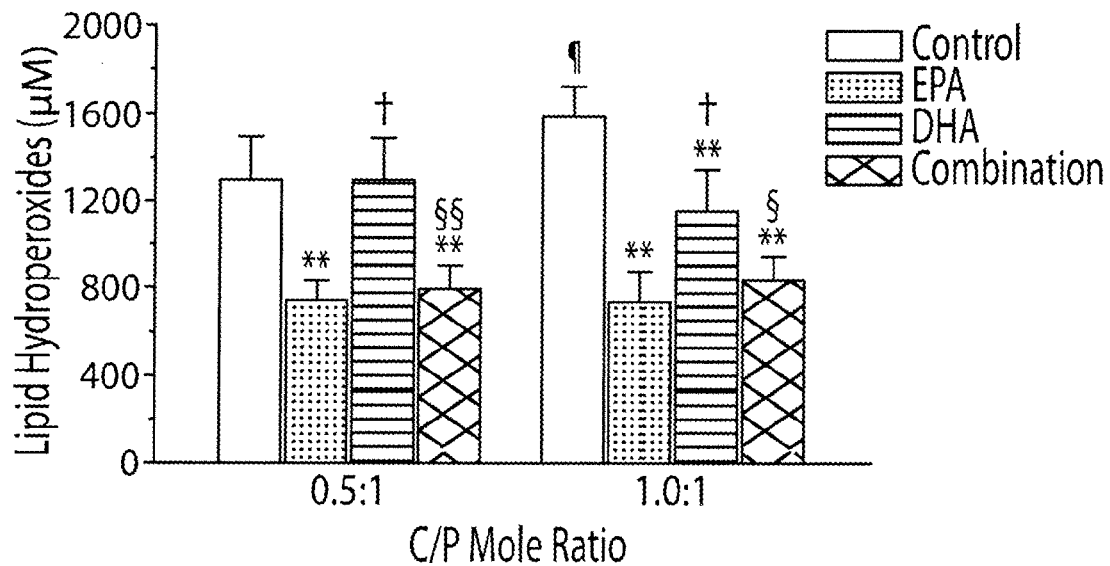
FIG. 3 shows cholesterol-dependent effects of EPA, DHA and Combination Treatment on membrane lipid peroxidation.
Figure 4:
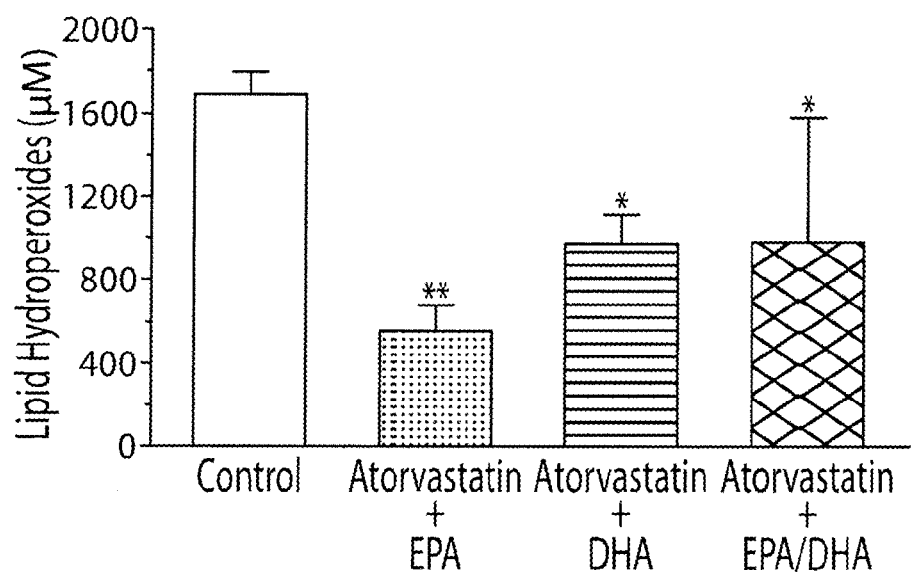
FIG. 4 EPA, DHA or EPA/DHA with atorvastatin (10:1 Mole Ratio) on lipid peroxide levels in cholesterol enriched membranes (1:1 cholesterol-to-phospholipid ratio).

Results are shown in FIGS. 1-4.

We claim:

1. A method of treating hypertriglyceridemia in a subject in need thereof comprising, administering to the subject daily a statin and about 4 g of ethyl eicosapentaenoate effective to reduce fasting triglycerides and LDL-C relative to subjects having hypertriglyceridemia who are receiving a statin without said ethyl eicosapentaenoate.

2. The method of claim 1 wherein said administering step reduces fasting triglycerides by at least 10% relative to subjects with hypertriglyceridemia who are are receiving a statin without said ethyl eicosapentaenoate.

3. The method of claim 1 wherein said administering step reduces fasting triglycerides by at least 15% relative to subjects with hypertriglyceridemia who are receiving a statin without said ethyl eicosapentaenoate.

4. The method of claim 1 wherein said administering step reduces fasting triglycerides by at least 20% relative to subjects with hypertriglyceridemia who are receiving a statin without said ethyl eicosapentaenoate.

5. The method of claim 1 wherein said administering step reduces fasting triglycerides by at least 25% and LDL-C by at least 5% relative to subjects with hypertriglyceridemia who are receiving a statin without said ethyl eicosapentaenoate.

6. The method of claim 1 wherein said administering step reduces fasting apolipoprotein B relative to subjects with hypertriglyceridemia who are receiving a statin without said ethyl eicosapentaenoate.

7. The method of claim 1 wherein said administering step reduces fasting apolipoprotein B by at least 5% relative to subjects with hypertriglyceridemia who are receiving a statin without said ethyl eicosapentaenoate.

8. The method of claim 1 wherein said administering step reduces fasting VLDL-C relative to subjects with hypertriglyceridemia who are receiving a statin without said ethyl eicosapentaenoate.

9. The method of claim 1 wherein said administering step reduces fasting VLDL-C by at least 15% relative to subjects with hypertriglyceridemia who are receiving a statin without said ethyl eicosapentaenoate.

10. The method of claim 1 wherein the statin is selected from lovastatin, mevastatin, pitavastatin, pravastatin, rosuvastatin, fluvastatin, atorvastatin and simvastatin.

11. The method of claim 1 wherein the ethyl eicosapentaenoate is administered to the subject in 1 to about 10 dosage units per day.

12. The method of claim 11 wherein the dosage units comprise capsules.

13. The method of claim 1 wherein the ethyl eicosapentaenoate is administered to the subject in 1 to about 4 dosage units per day.

14. The method of claim 13 wherein the dosage units comprise capsules.

\* \* \* \* \*